United States Patent
Barda et al.

(10) Patent No.: US 7,666,879 B2
(45) Date of Patent: Feb. 23, 2010

(54) IMIDAZO[1,2-A]PYRIDINE COMPOUNDS AS VEGF-R2 INHIBITORS

(75) Inventors: David Anthony Barda, Indianapolis, IN (US); Timothy Paul Burkholder, Carmel, IN (US); Joshua Ryan Clayton, Fishers, IN (US); Yan Hao, Zionsville, IN (US); James Robert Henry, Indianapolis, IN (US); John Monte Knobeloch, Indianapolis, IN (US); Johnathan Alexander McLean, Indianapolis, IN (US); David Mendel, Indianapolis, IN (US); Mark Edward Rempala, Indianapolis, IN (US); Zhao-Qing Wang, Indianapolis, IN (US); Yvonne Yee Mai Yip, Indianapolis, IN (US); Boyu Zhong, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 43 days.

(21) Appl. No.: 11/816,416

(22) PCT Filed: Feb. 23, 2006

(86) PCT No.: PCT/US2006/006283
§ 371 (c)(1),
(2), (4) Date: May 30, 2008

(87) PCT Pub. No.: WO2006/091671
PCT Pub. Date: Aug. 31, 2006

(65) Prior Publication Data
US 2009/0227622 A1    Sep. 10, 2009

Related U.S. Application Data

(60) Provisional application No. 60/655,981, filed on Feb. 24, 2005.

(51) Int. Cl.
*A01N 43/42* (2006.01)
*A61K 31/44* (2006.01)
*C07D 471/02* (2006.01)
*C07D 491/02* (2006.01)
*C07D 498/02* (2006.01)
*C07D 513/02* (2006.01)
*C07D 515/02* (2006.01)
*C07D 401/00* (2006.01)

(52) U.S. Cl. .................... 514/300; 546/121; 546/272.7; 546/273.1

(58) Field of Classification Search ................. 514/300; 546/121, 272.7, 273.1
See application file for complete search history.

(56) References Cited

U.S. PATENT DOCUMENTS 6,492,529 B1    12/2002   Kapadia et al.
7,125,888 B2 *  10/2006   Bilodeau et al. ............ 514/300

FOREIGN PATENT DOCUMENTS

| EP | 1 657 242 A1 | 5/2006 |
| WO | WO 99/16755 | 4/1999 |
| WO | WO 01/04115 | 1/2001 |
| WO | WO 03/005999 | 1/2003 |
| WO | WO 03/092595 | 11/2003 |
| WO | WO 2004/052315 | 6/2004 |

OTHER PUBLICATIONS

Pargellis, Christopher, Inhibition of p38 MAP Kinase by Utilizing a Novel Allosteric Binding Site, Nature Structural Biology, 2002, 9(4), p. 268-272.

Wu, Zhicai, Design and Synthesis of 3,7-diarylimidazopyridines as Inhibitors if the VEGF-receptor KDR, Bioorganic & Medicinal Chemistry Letters, 14, 2004, p. 909-912.

* cited by examiner

*Primary Examiner*—Sreeni Padmanabhan
*Assistant Examiner*—Sarah Pihonak
(74) *Attorney, Agent, or Firm*—Elizabeth A. McGraw; Tina M. Tucker

(57) ABSTRACT

The present invention provides compounds that are inhibitors of VEGF-R2 of the formula: (I) and methods of using these compounds.

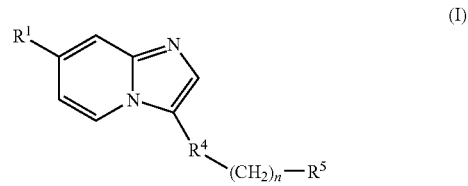

(I)

7 Claims, No Drawings

IMIDAZO[1,2-A]PYRIDINE COMPOUNDS AS VEGF-R2 INHIBITORS

This application is a United States national phase entry, pursuant to 35 U.S.C. 371, of PCT/US2006/006283, filed Feb. 23, 2006, which claims the benefit of U.S. provisional patent application Ser. No. 60/655,981 filed Feb. 24, 2005.

BACKGROUND OF THE INVENTION

Unwanted angiogenesis is a hallmark of several diseases, such as retinopathies, psoriasis, rheumatoid arthritis, age-related macular degeneration (AMD), and cancer (solid tumors). (Folkman, Nature Med., 1, 27-31 (1995)). Because tumors require a blood supply to survive, angiogenesis is a critical component contributing to the cancer disease process (E. Ruoslahti, Nature Rev. Cancer, 2, 83-90 (2002). The development of new agents for the inhibition of angiogenesis therefore represents a promising approach for cancer therapy (R. Kerbel and J. Folkman, Nature Rev. Cancer, 2, 727-739 (2002). Another possible benefit to inhibiting tumor angiogenesis is that this approach may lack the toxic side effects or drug resistance-inducing properties of conventional chemotherapy (Judah Folkman, *Endogenous Inhibitors of Angiogenesis*, The Harvey Lectures, Series 92, pages 65-82, Wiley-Liss Inc., (1998)).

One of the protein kinases which has been shown to be involved in the angiogenic process is a member of the growth factor receptor tyrosine kinase family called VEGF-R2 (vascular endothelial growth factor receptor 2, also known as KDR (kinase insert domain receptor)). VEGF-R2, which is expressed primarily on endothelial cells, binds the potent angiogenic growth factor VEGF and mediates the subsequent signal transduction through activation of its intracellular kinase activity. Thus, it is expected that direct inhibition of the kinase activity of VEGF-R2 will result in the reduction of angiogenesis even in the presence of exogenous VEGF (see Strawn et al., Cancer Research, 56, 3540-3545 (1996)), as has been shown with mutants of VEGF-R2 which fail to mediate signal transduction. (Millauer et al., Cancer Research, 56, 1615-1620 (1996)). The importance of VEGF-R2 as a target for cancer drug therapy was further indicated in recent studies (S. Rafii et al., Nature Rev. Cancer, 2, 826-835 (2002) and Y. Shaked et al., Cancer Cell, 7, 101-111 (2004)) which demonstrated that VEGF-R2 is expressed on bone marrow-derived circulating endothelial precursor cells that can also contribute to the angiogenesis and growth of tumors. Furthermore, VEGF-R2 appears to have no function in the adult beyond that of mediating the angiogenic activity of VEGF.

It has been proposed to treat angiogenesis by the use of compounds inhibiting the kinase activity of VEGF-R2. For example, WIPO International Publication No. WO 97/34876 discloses certain cinnoline derivatives that are inhibitors of VEGF-R2, which are taught to be useful for the treatment of disease states associated with abnormal angiogenesis and/or increased vascular permeability including diabetes (hyperglycemia), psoriasis, rheumatoid arthritis, Kaposi's sarcoma, haemangioma, acute and chronic nephropathies, atheroma, arterial restinosis, autoimmune diseases, acute inflammation, ocular diseases with retinal vessel proliferation, and cancer.

Further, WO 03/092595 provides certain imidazo[1,2-a]pyridinyl compounds that inhibit, regulate, and/or modulate tyrosine kinase signal transduction.

There is still a need, however, for effective inhibitors of protein kinases.

The present invention provides novel imidazo[1,2-a]pyridinyl compounds that inhibit VEGF-R2 and are therefore useful in the treatment of VEGF-R2 mediated or dependent diseases such as the treatment of various forms of cancer.

BRIEF SUMMARY OF THE INVENTION

The present invention provides compounds of Formula I:
A compound of Formula (I):

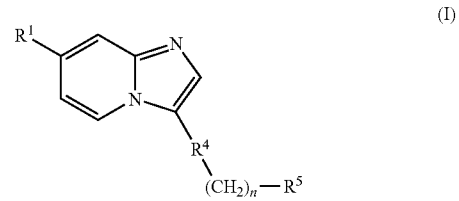

(I)

wherein:
$R^1$: is (a) 2-pyridonyl optionally substituted with —(CH$_2$)$_{1-4}$NR$^2$R$^3$; or
(b) phenyl, thienyl, thiazolyl, imidazolyl, pyrazolyl, triazolyl, oxazolyl, pyridinyl, N-oxo-pyridinyl, or pyrimidinyl, all of which are optionally substituted with —(CH$_2$)$_{0-4}$NR$^2$R$^3$, $C_1$-$C_6$ alkyl optionally substituted with amino, pyrrolidinyl, or morpholinyl, or 1-2 substituents independently selected from the group consisting of $C_1$-$C_4$ alkoxy, halo, ($C_1$-$C_6$ alkyl)sulfonyl, nitro, -sulfonyl(CH$_2$)$_{0-4}$NR$^2$R$^3$, and -carbonyl(CH$_2$)$_{0-4}$NR$^2$R$^3$;

$R^2$ is hydrogen or $C_1$-$C_6$ alkyl optionally substituted with hydroxy;

$R^3$ is hydrogen or $C_1$-$C_6$ alkyl optionally substituted with hydroxy, trifluoromethyl, or pyrrolidinyl; or $R^2$, $R^3$, and the nitrogen to which they are attached form piperidinyl, piperazinyl optionally substituted with $C_1$-$C_6$ alkyl, or morpholinyl;

$R^4$ is thiazolyl, pyridinyl, or phenyl optionally substituted with 1-3 substituents selected from the group consisting of halo, amino, methyl, trifluoromethyl, and nitro;

$R^5$ is C(O)NHR$^6$, OC(O)NHR$^6$, NHC(O)CH$_2$R$^6$, NHC(O)NHR$^6$ or C(S)NHR$^6$;

n is 0-4 for OC(O)NHR$^6$, NHC(O)CH$_2$R$^6$, NHC(O)NHR$^6$ and n is 1-4 for C(O)NHR$^6$ and C(S)NHR$^6$; and $R^6$ is (a) unsubstituted tetrahydrobenzothiazolyl; or
(b) phenyl, pyridinyl, pyrimidinyl, pyrazolyl, thiazolyl, isothiazolyl, thiadiazolyl, isoxazolyl, all of which are optionally substituted with 1-3 substituents independently selected from the group consisting of $C_1$-$C_6$ alkyl optionally substituted with hydroxy, dimethylamino, pyrrolidinyl, piperidinyl, or morpholinyl, $C_2$-$C_6$ alkenyl optionally substituted with dimethylaminocarbonyl, $C_1$-$C_6$ alkoxy, trifluoromethyl, difluoromethoxy, trifluoromethoxy, dimethylaminoethoxy, phenoxy, tolyl, halo, methylsulfonyl, dimethylamino, diethylamino, cyano, $C_3$-$C_6$ cycloalkyl optionally substituted with hydroxy, methoxy, methoxyethoxy, or methyl, 3,4-dimethylisoxazol-5-yl-aminosulfonyl, tetrahydropyranyl, tetrahydropyranylaminocarbonyl, $C_2$-$C_6$ alkylcarbonyl, morpholinylcarbonyl, and piperazinylcarbonyl; or pharmaceutically acceptable salts thereof.

The present invention further provides a method of inhibiting VEGF-R$^2$ in a mammal comprising administering to a mammal in need of such treatment a VEGF-R$^2$ inhibiting amount of a compound of Formula I or a pharmaceutically acceptable salt thereof.

The present invention further provides a method of blocking angiogenesis comprising administering to a mammal in need of such treatment a VEGF-R$^2$ inhibiting amount of a compound of Formula I or a pharmaceutically acceptable salt thereof.

The present invention further provides a method of treating susceptible neoplasms in a mammal comprising administering to a mammal in need of such treatment a VEGF-R2 inhibiting amount of a compound of Formula I or a pharmaceutically acceptable salt thereof.

The present invention also provides a method of treating a number of disease states including hyperglycemia, psoriasis rheumatoid arthritis, Kaposi's sarcoma, haemangioma, acute and chronic nephropathies, atheroma, arterial restinosis, autoimmune diseases, acute inflammation, and ocular diseases with retinal vessel proliferation in a mammal comprising administering to a mammal in need of such treatment a VEGF-R2 inhibiting amount of a compound of Formula I or a pharmaceutically acceptable salt thereof.

The present invention also provides a pharmaceutical formulation comprising a compound of Formula I or a pharmaceutically acceptable salt thereof and one or more pharmaceutically acceptable excipients.

This invention also provides the use of a compound of Formula I or a pharmaceutically acceptable salt thereof for the manufacture of a medicament for the inhibition of VEGF-R2.

The present invention also provides the use of a compound of Formula I or a pharmaceutically acceptable salt thereof for the manufacture of a medicament to block angiogenesis.

The present invention also provides the use of a compound of Formula I or a pharmaceutically acceptable salt thereof for the manufacture of a medicament for the treatment of susceptible neoplasms.

The present invention also provides the use of a compound of Formula I or a pharmaceutically acceptable salt thereof for the manufacture of a medicament for the treatment of a number of disease states selected from the group consisting of hyperglycemia, psoriasis, rheumatoid arthritis, Kaposi's sarcoma, haemangioma, acute and chronic nephropathies, atheroma, arterial restinosis, autoimmune diseases, acute inflammation, and ocular diseases with retinal vessel proliferation.

DETAILED DESCRIPTION OF THE INVENTION

The general chemical terms used in the formulae above have their usual meanings. For example, the term "$C_1$-$C_6$ alkyl" includes straight chain and branched alkyls and include methyl, ethyl, propyl, isopropyl, butyl, isobutyl, sec-butyl, tert-butyl, pentyl, isopentyl, and hexyl moieties. The term "$C_2$-$C_6$ alkenyl" includes straight chain and branched alkylene groups and include ethylenyl, propylenyl, isopropylenyl, butylenyl, isobutylenyl, sec-butylenyl, tert-butylenyl, pentylenyl, isopentylenyl, and hexylenyl moieties. The term "$C_3$-$C_6$ cycloalkyl" includes cyclopropyl, cyclobutyl, cyclopentyl, and cyclohexyl moieties. The term "$C_1$-$C_6$ alkoxy" includes methoxy, ethoxy, propoxy, isopropoxy, butoxy, isobutoxy, sec-butoxy, tert-butoxy, pentoxy, isopentoxy, and hexoxy. The term "halo" is taken to mean chloro, bromo, fluoro, or iodo. The term "($C_1$-$C_6$ alkyl)sulfonyl" is taken to mean a sulfonyl group substituted with a $C_1$-$C_6$ alkyl group.

The term "mammal" is taken to mean any of various warm-blooded vertebrate animals of the class Mammalia, most preferably humans, characterized by a covering of hair on the skin and, in the female, milk-producing mammary glands for nourishing the young.

The term "susceptible neoplasm" is defined to be a neoplasm that depends upon VEGF-R2 for its survival, growth, or metastasis.

While all of the compounds of Formula I are useful inhibitors of VEGF-R2, certain classes of compounds are preferred. The following paragraphs describe such preferred classes.

a) $R^1$ is pyridinyl;
b) $R^1$ is pyridin-2-yl;
c) $R^1$ is pyridin-4-yl;
d) $R^1$ is substituted pyridinyl;
e) $R^1$ is substituted pyridin-2-yl;
f) $R^1$ is substituted pyridin-4-yl;
g) $R^1$ is pyridinyl substituted with 2-morpholinylpropyl;
h) $R^1$ is thienyl;
i) $R^1$ is thien-2-yl;
j) $R^1$ is thien-3-yl;
k) $R^1$ is phenyl;
l) $R^1$ is methylsulfonylphenyl;
m) $R^4$ is phenyl;
n) $R^4$ is substituted phenyl;
o) $R^4$ is halophenyl;
p) $R^4$ is chlorophenyl;
q) $R^4$ is 2-chlorophenyl;
r) $R^4$ is fluorophenyl;
s) $R^4$ is 2-fluorophenyl;
t) n is 0;
u) n is 1;
v) $R^5$ is NHC(O)NHR$^6$;
w) $R^5$ is C(O)NHR$^6$;
x) $R^6$ is substituted pyrazolyl;
y) $R^6$ is pyrazolyl substituted with $C_1$-$C_6$ alkyl;
z) $R^6$ is 5-tert-butyl-pyrazol-3-yl;
aa) $R^6$ is substituted phenyl;
bb) $R^6$ is trifluoromethylphenyl;
cc) $R^6$ is m-trifluoromethylphenyl;
dd) $R^6$ is substituted thiadiazolyl;
ee) $R^6$ is thiadiazolyl substituted with $C_1$-$C_6$ alkyl;
ff) $R^6$ is 5-tert-butyl-thiadiazol-2-yl;
gg) $R^6$ is substituted isoxazolyl;
hh) $R^6$ is isoxazolyl substituted with $C_1$-$C_6$ alkyl;
ii) $R^6$ is 5-tert-butyl-isoxazol-3-yl;
jj) $R^6$ is 3-tert-butyl-isoxazol-5-yl;
kk) $R^6$ is substituted thiazolyl;
ll) $R^6$ is thiazolyl substituted 1-2 times with $C_1$-$C_6$ alkyl;
mm) $R^6$ is 5-tert-butyl-thiazol-2-yl;
nn) $R^6$ is 5-tert-butyl-4-morpholin-4-ylmethyl-thiazol-2-yl;
oo) $R^6$ is 4-methyl-5-i-propylthiazol-2-yl;
pp) $R^6$ is 4-dimethylaminomethyl-5-(1-methylcyclopropyl)thiazol-2-yl;
qq) $R^6$ is substituted pyridinyl;
rr) $R^6$ is 4-tert-butyl-6-morpholinymethylpyridin-2-yl;
ss) $R^6$ is 4-trifluoromethylpyridin-2-yl;
tt) $R^1$ is pyridinyl, $R^4$ is phenyl, n is 1, $R^5$ is CONHR$^6$, and $R^6$ is 3-trifluoromethylphenyl;
uu) $R^1$ is pyridinyl, $R^4$ is fluorophenyl, n is 1, $R^5$ is CONHR$^6$, and $R^6$ is 5-tert-butyl-thiadiazol-2-yl;
vv) $R^1$ is pyridinyl, $R^4$ is fluorophenyl, n is 1, $R^5$ is CONHR$^6$, and $R^6$ is 4-methyl-5-isopropyl-thiazol-2-yl;
ww) $R^1$ is pyridinyl, $R^4$ is fluorophenyl, n is 1, $R^5$ is CONHR$^6$, and $R^6$ is 4-tert-butyl-6-morpholinylmethylpyridin-2-yl;
xx) $R^1$ is 2-(2-morpholinylpropyl)pyridin-4-yl, $R^4$ is fluorophenyl, n is 1, $R^5$ is CONR$^6$, and $R^6$ is 4-trifluoromethylpyridinyl; both enantiomers and racemate;

yy) $R^1$ is pyridinyl, $R^4$ is fluorophenyl, n is 1, $R^5$ is CONHR$^6$, and $R^6$ is 4-dimethylamino-5-methylcyclopropylthiazol-2-yl;

zz) $R^1$ is pyridinyl, $R^4$ is fluorophenyl, n is 1, $R^5$ is CONHR$^6$, and $R^6$ is 4-morpholinylmethyl-5-t-butyl-thiazol-2-yl;

aaa) A compound of Formula I which is 2-[4-(7-pyridin-4-yl-imidazo[1,2-a]pyridin-3-yl)-phenyl]-N-(3-trifluoromethyl-phenyl)-acetamide;

bbb) A compound of Formula I which is N-(5-tert-butyl-[1,3,4]thiadiazol-2-yl)-2-[2-fluoro-4-(7-pyridin-4-yl-imidazo[1,2-a]pyridin-3-yl)-phenyl]-acetamide;

ccc) A compound of Formula I which is 2-[2-fluoro-4-(7-pyridin-4-yl-imidazo[1,2-a]pyridin-3-yl)-phenyl]-N-(5-isopropyl-4-methyl-thiazol-2-yl)-acetamide;

ddd) A compound of Formula I which is N-(4-tert-butyl-6-morpholin-4-ylmethyl-pyridin-2-yl)-2-[2-fluoro-4-(7-pyridin-4-yl-imidazo[1,2-a]pyridin-3-yl)-phenyl]-acetamide;

eee) A compound of Formula I which is 2-(2-fluoro-4-{7-[2-(2-morpholin-4-yl-propyl)-pyridin-4-yl]-imidazo[1,2-a]pyridin-3-yl}-phenyl)-N-(4-trifluoromethyl-pyridin-2-yl)-acetamide;

fff) A compound of Formula I which is N-[4-dimethylaminomethyl-5-(1-methyl-cyclopropyl)-thiazol-2-yl]-2-[2-fluoro-4-(7-pyridin-4-yl-imidazo[1,2-a]pyridin-3-yl)-phenyl]-acetamide;

ggg) A compound of Formula I which is 2-[2-fluoro-4-(7-pyridin-4-yl-imidazo[1,2-a]pyridin-3-yl)-phenyl]-N-[5-tert-butyl-4-morpholin-4-ylmethyl-thiazol-2-yl]-acetamide;

hhh) A compound of Claim 1 wherein $R^1$ is phenyl, thienyl, thiazolyl, or pyridinyl all of which are optionally substituted with —(CH$_2$)$_{0-4}$NR$^2$R$^3$, C$_1$-C$_6$ alkyl optionally substituted with amino, pyrrolidinyl, or morpholinyl, or 1-2 substituents independently selected from the group consisting of C$_1$-C$_4$ alkoxy, halo, (C$_1$-C$_6$ alkyl)sulfonyl, nitro, -sulfonyl(CH$_2$)$_{0-4}$NR$^2$R$^3$, and -carbonyl(CH$_2$)$_{0-4}$NR$^2$R$^3$;

iii) A compound of claim 1 wherein $R^1$ is 4-pyridinyl which is optionally substituted with —(CH$_2$)$_{0-4}$NR$^2$R$^3$, C$_1$-C$_6$ alkyl optionally substituted with amino, pyrrolidinyl, or morpholinyl, or 1-2 substituents independently selected from the group consisting of C$_1$-C$_4$ alkoxy, halo, (C$_1$-C$_6$ alkyl)sulfonyl, nitro, -sulfonyl(CH$_2$)$_{0-4}$NR$^2$R$^3$, and -carbonyl(CH$_2$)$_{0-4}$NR$^2$R$^3$; and $R^6$ is phenyl, pyridinyl, pyrimidinyl, pyrazolyl, thiazolyl, isothiazolyl, thiadiazolyl, isoxazolyl, all of which are optionally substituted with 1-3 substituents independently selected from the group consisting of C$_1$-C$_6$ alkyl optionally substituted with hydroxy, dimethylamino, pyrrolidinyl, piperidinyl, or morpholinyl, C$_2$-C$_6$ alkenyl optionally substituted with dimethylaminocarbonyl, C$_1$-C$_6$ alkoxy, trifluoromethyl, difluoromethoxy, trifluoromethoxy, dimethylaminoethoxy, phenoxy, tolyl, halo, methylsulfonyl, dimethylamino, diethylamino, cyano, C$_3$-C$_6$ cycloalkyl optionally substituted with hydroxy, methoxy, methoxyethoxy, or methyl, 3,4-dimethylisoxazol-5-yl-aminosulfonyl, tetrahydropyranyl, tetrahydropyranylaminocarbonyl, C$_2$-C$_6$ alkylcarbonyl, morpholinylcarbonyl, and piperazinylcarbonyl;

jjj) A compound of Claim 1 wherein $R^1$ is 2-pyridinyl which is optionally substituted with —(CH$_2$)$_{0-4}$NR$^2$R$^3$, C$_1$-C$_6$ alkyl optionally substituted with amino, pyrrolidinyl, or morpholinyl, or 1-2 substituents independently selected from the group consisting of C$_1$-C$_4$ alkoxy, halo, (C$_1$-C$_6$ alkyl)sulfonyl, nitro, -sulfonyl (CH$_{12}$)$_{0-4}$NR$^2$R$^3$, and -carbonyl(CH$_2$)$_{0-4}$NR$^2$R$^3$; and $R^6$ is phenyl, pyridinyl, thiazolyl, isothiazolyl, thiadiazolyl, or isoxazolyl, all of which are optionally substituted with 1-3 substituents independently selected from the group consisting of C$_1$-C$_6$ alkyl optionally substituted with hydroxy, dimethylamino, pyrrolidinyl, piperidinyl, or morpholinyl, C$_2$-C$_6$ alkenyl optionally substituted with dimethylaminocarbonyl, C$_1$-C$_6$ alkoxy, trifluoromethyl, difluoromethoxy, trifluoromethoxy, dimethylaminoethoxy, phenoxy, tolyl, halo, methylsulfonyl, dimethylamino, diethylamino, cyano, C$_3$-C$_6$ cycloalkyl optionally substituted with hydroxy, methoxy, methoxyethoxy, or methyl, 3,4-dimethylisoxazol-5-yl-aminosulfonyl, tetrahydropyranyl, tetrahydropyranylaminocarbonyl, C$_2$-C$_6$ alkylcarbonyl, morpholinylcarbonyl, and piperazinylcarbonyl.

kkk) A compound of Claim 1 wherein $R^1$ is phenyl which is optionally substituted with —(CH$_2$)$_{0-4}$NR$^2$R$^3$, C$_1$-C$_6$ alkyl optionally substituted with amino, pyrrolidinyl, or morpholinyl, or 1-2 substituents independently selected from the group consisting of C$_1$-C$_4$ alkoxy, halo, (C$_1$-C$_6$ alkyl)sulfonyl, nitro, -sulfonyl(CH$_2$)$^{0-4}$NR$^2$R$^3$, and -carbonyl(CH$_2$)$_{0-4}$NR$^2$R$^3$; and $R^6$ is phenyl, pyridinyl, pyrazolyl, thiazolyl, isothiazolyl, thiadiazolyl, or isoxazolyl, all of which are optionally substituted with 1-3 substituents independently selected from the group consisting of C$_1$-C$_6$ alkyl optionally substituted with hydroxy, dimethylamino, pyrrolidinyl, piperidinyl, or morpholinyl, C$_2$-C$_6$ alkenyl optionally substituted with dimethylaminocarbonyl, C$_1$-C$_6$ alkoxy, trifluoromethyl, difluoromethoxy, trifluoromethoxy, dimethylaminoethoxy, phenoxy, tolyl, halo, methylsulfonyl, dimethylamino, diethylamino, cyano, C$_3$-C$_6$ cycloalkyl optionally substituted with hydroxy, methoxy, methoxyethoxy, or methyl, 3,4-dimethylisoxazol-5-yl-aminosulfonyl, tetrahydropyranyl, tetrahydropyranylaminocarbonyl, C$_2$-C$_6$ alkylcarbonyl, morpholinylcarbonyl, and piperazinylcarbonyl;

lll) A compound of Claim 1 wherein $R^1$ is thienyl or thiazolyl which is optionally substituted with —(CH$_2$)$_{0-4}$NR$^2$R$^3$, C$_1$-C$_6$ alkyl optionally substituted with amino, pyrrolidinyl, or morpholinyl, or 1-2 substituents independently selected from the group consisting of C$_1$-C$_4$ alkoxy, halo, (C$_1$-C$_6$ alkyl)sulfonyl, nitro, -sulfonyl(CH$_2$)$_{0-4}$NR$^2$R$^3$, and -carbonyl(CH$_2$)$_{0-4}$NR$^2$R$^3$; and $R^6$ is phenyl, pyrazolyl, thiazolyl, isothiazolyl, thiadiazolyl, or isoxazolyl, all of which are optionally substituted with 1-3 substituents independently selected from the group consisting of C$_1$-C$_6$ alkyl optionally substituted with hydroxy, dimethylamino, pyrrolidinyl, piperidinyl, or morpholinyl, C$_2$-C$_6$ alkenyl optionally substituted with dimethylaminocarbonyl, C$_1$-C$_6$ alkoxy, trifluoromethyl, difluoromethoxy, trifluoromethoxy, dimethylaminoethoxy, phenoxy, tolyl, halo, methylsulfonyl, dimethylamino, diethylamino, cyano, C$_3$-C$_6$ cycloalkyl optionally substituted with hydroxy, methoxy, methoxyethoxy, or methyl, 3,4-dimethylisoxazol-5-yl-aminosulfonyl, tetrahydropyranyl, tetrahydropyranylaminocarbonyl, C$_2$-C$_6$ alkylcarbonyl, morpholinylcarbonyl, and piperazinylcarbonyl;

mmm) A compound of Claim 1 wherein $R^1$ is 3-pyridinyl which is optionally substituted with —(CH$_2$)$_{0-4}$NR$^1$R$^3$, C$_1$-C$_6$ alkyl optionally substituted with amino, pyrrolidinyl, or morpholinyl, or 1-2 substituents independently selected from the group consisting of C$_1$-C$_4$ alkoxy, halo, (C$_1$-C$_6$ alkyl)sulfonyl, nitro, -sulfonyl (CH$_2$)$_{0-4}$NR$^2$R$^3$, and -carbonyl(CH$_2$)$_{0-4}$NR$^2$R$^3$; and $R^6$ is phenyl, thiazolyl, isothiazolyl, thiadiazolyl, or isoxazolyl, all of which are optionally substituted with 1-3 substituents independently selected from the group consisting of $C_1$-$C_6$ alkyl optionally substituted with hydroxy, dimethylamino, pyrrolidinyl, piperidinyl, or morpholinyl, $C_2$-$C_6$ alkenyl optionally substituted with dimethylaminocarbonyl, $C_1$-$C_6$ alkoxy, trifluoromethyl, difluoromethoxy, trifluoromethoxy, dimethylaminoethoxy, phenoxy, tolyl, halo, methylsulfonyl, dimethylamino, diethylamino, cyano, $C_3$-$C_6$ cycloalkyl optionally substituted with hydroxy, methoxy, methoxyethoxy, or methyl, 3,4-dimethylisoxazol-5-yl-aminosulfonyl, tetrahydropyranyl, tetrahydropyranylaminocarbonyl, $C_2$-$C_6$ alkylcarbonyl, morpholinylcarbonyl, and piperazinylcarbonyl;

nnn) A compound of Formula I which is selected from the group consisting of HCl, diHCL, succinate, L-tartrate, and HBr salts;

ooo) A compound of Formula I which is selected from the group consisting of HCl and HBr salts; and ppp) A compound of Formula I which is a succinate salt.

It will be understood that the above classes may be combined to form additional preferred classes.

Another preferred class of the present invention is compounds of Formula II:

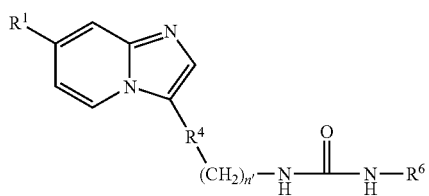

(II)

wherein:

$R^1$: is (a) 2-pyridonyl optionally substituted with —(CH$_2$)$_{1-4}$NR$^2$R$^3$; or (b) phenyl, thienyl, thiazolyl, imidazolyl, pyrazolyl, triazolyl, oxazolyl, pyridinyl, N-oxo-pyridinyl, or pyrimidinyl, all of which are optionally substituted with —(CH$_2$)$_{0-4}$NR$^2$R$^3$, $C_1$-$C_6$ alkyl optionally substituted with amino, pyrrolidinyl, or morpholinyl, or 1-2 substituents independently selected from the group consisting of $C_1$-$C_4$ alkoxy, halo, ($C_1$-$C_6$ alkyl)sulfonyl, nitro, -sulfonyl(CH$_2$)$_{0-4}$NR$^2$R$^3$, and -carbonyl(CH$_2$)$_{0-4}$NR$^2$R$^3$;

$R^2$ is hydrogen or $C_1$-$C_6$ alkyl optionally substituted with hydroxy;

$R^3$ is hydrogen or $C_1$-$C_6$ alkyl optionally substituted with hydroxy, trifluoromethyl, or pyrrolidinyl; or $R^2$, $R^3$ and the nitrogen to which they are attached form piperidinyl, piperazinyl optionally substituted with $C_1$-$C_6$ alkyl, or morpholinyl;

$R^4$ is thiazolyl, pyridinyl, or phenyl optionally substituted with 1-3 substituents selected from the group consisting of halo, amino, methyl, trifluoromethyl, and nitro; and $R^6$ is (a) unsubstituted tetrahydrobenzothiazolyl; or (b) phenyl, pyridinyl, pyrimidinyl, pyrazolyl, thiazolyl, isothiazolyl, thiadiazolyl, isoxazolyl, all of which are optionally substituted with 1-3 substituents independently selected from the group consisting of $C_1$-$C_6$ alkyl optionally substituted with hydroxy, dimethylamino, pyrrolidinyl, piperidinyl, or morpholinyl, $C_2$-$C_6$ alkenyl optionally substituted with dimethylaminocarbonyl, $C_1$-$C_6$ alkoxy, trifluoromethyl, difluoromethoxy, trifluoromethoxy, dimethylaminoethoxy, phenoxy, tolyl, halo, methylsulfonyl, dimethylamino, diethylamino, cyano, $C_3$-$C_6$ cycloalkyl optionally substituted with hydroxy, methoxy, methoxyethoxy, or methyl, 3,4-dimethylisoxazol-5-yl-aminosulfonyl, tetrahydropyranyl, tetrahydropyranylaminocarbonyl, $C_2$-$C_6$ alkylcarbonyl, morpholinylcarbonyl, and piperazinylcarbonyl; or pharmaceutically acceptable salts thereof.

Another preferred class of the present invention is compounds of Formula III:

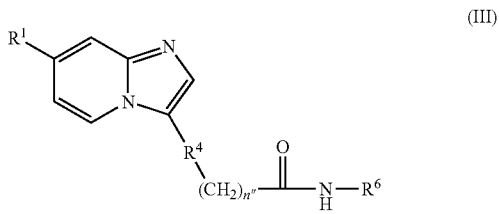

(III)

wherein:

$R^1$: is (a) 2-pyridonyl optionally substituted with —(CH$_2$)$_{1-4}$NR$^2$R$^3$; or (b) phenyl, thienyl, thiazolyl, imidazolyl, pyrazolyl, triazolyl, oxazolyl, pyridinyl, N-oxo-pyridinyl, or pyrimidinyl, all of which are optionally substituted with —(CH$_2$)$_{0-4}$NR$^2$R$^3$, $C_1$-$C_6$ alkyl optionally substituted with amino, pyrrolidinyl, or morpholinyl, or 1-2 substituents independently selected from the group consisting of $C_1$-$C_4$ alkoxy, halo, ($C_1$-$C_6$ alkyl)sulfonyl, nitro, -sulfonyl(CH$_2$)$_{0-4}$NR$^2$R$^3$, and -carbonyl(CH$_2$)$_{0-4}$NR$^2$R$^3$;

$R^2$ is hydrogen or $C_1$-$C_6$ alkyl optionally substituted with hydroxy;

$R^3$ is hydrogen or $C_1$-$C_6$ alkyl optionally substituted with hydroxy, trifluoromethyl, or pyrrolidinyl; or $R^2$, $R^3$ and the nitrogen to which they are attached form piperidinyl, piperazinyl optionally substituted with $C_1$-$C_6$ alkyl, or morpholinyl;

$R^4$ is thiazolyl, pyridinyl, or phenyl optionally substituted with 1-3 substituents selected from the group consisting of halo, amino, methyl, trifluoromethyl, and nitro; and $R^6$ is (a) unsubstituted tetrahydrobenzothiazolyl; or (b) phenyl, pyridinyl, pyrimidinyl, pyrazolyl, thiazolyl, isothiazolyl, thiadiazolyl, isoxazolyl, all of which are optionally substituted with 1-3 substituents independently selected from the group consisting of $C_1$-$C_6$ alkyl optionally substituted with hydroxy, dimethylamino, pyrrolidinyl, piperidinyl, or morpholinyl, $C_2$-$C_6$ alkenyl optionally substituted with dimethylaminocarbonyl, $C_1$-$C_6$ alkoxy, trifluoromethyl, difluoromethoxy, trifluoromethoxy, dimethylaminoethoxy, phenoxy, tolyl, halo, methylsulfonyl, dimethylamino, diethylamino, cyano, $C_3$-$C_6$ cycloalkyl optionally substituted with hydroxy, methoxy, methoxyethoxy, or methyl, 3,4-dimethylisoxazol-5-yl-aminosulfonyl, tetrahydropyranyl, tetrahydropyranylaminocarbonyl, $C_2$-$C_6$ alkylcarbonyl, morpholinylcarbonyl, and piperazinylcarbonyl; or pharmaceutically acceptable salts thereof.

Another embodiment of the present invention is a compound of Formula (IV):

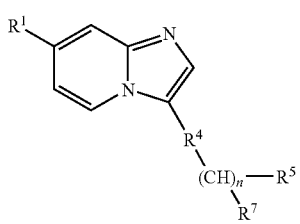

(IV)

wherein:

R[1]: is (a) 2-pyridonyl optionally substituted with $C_1$-$C_6$ alkyl or —$(CH_2)_{1-4}NR^2R^3$; or
  (b) phenyl, thienyl, thiazolyl, thiadiazolyl, imidazolyl, pyrazolyl, triazolyl, tetrazolyl, oxazolyl, isoxazolyl, pyridinyl, or pyrimidinyl, all of which may be optionally substituted with —$(CH_2)_{0-4}NR^2R^3$ or 1-2 substituents independently selected from the group consisting of $C_1$-$C_6$ alkyl, $C_1$-$C_4$ alkoxy, halo, and ($C_1$-$C_6$ alkyl)sulfonyl, -sulfonyl$(CH_2)_{0-4}NR^2R^3$, or -carbonyl($CH_2)_{0-4}NR^2R^3$;

$R^2$ is hydrogen or $C_1$-$C_6$ alkyl;

$R^3$ is hydrogen, $C_1$-$C_6$ alkyl optionally substituted with pyrrolidinyl, piperidinyl, piperazinyl optionally substituted with $C_1$-$C_4$ alkyl, or morpholinyl; or $R^2$ and $R^3$ taken together with the nitrogen to which they are attached form a pyrrolidinyl, piperidinyl, piperazinyl optionally substituted with $C_1$-$C_4$ alkyl, or morpholinyl;

$R^4$ is thiazolyl, thienyl, pyridinyl, or phenyl optionally substituted 1-2 times with halo;

n is 0-4;

$R^5$ is $C(O)NHR^6$, $OC(O)NHR^6$, $NHC(O)CH_2R^6$, or $NHC(O)NHR^6$;

$R^6$ is phenyl optionally substituted with 1-3 substituents independently selected from the group consisting of halo, $C_1$-$C_6$ alkyl, $C_1$-$C_4$ alkoxy, cyano, dimethylamino, difluoromethoxy, trifluoromethyl, trifluoromethoxy, methylsulfonyl, dimethylisoxazolylsulfonamide, and —O-phenyl, pyridinyl optionally substituted with trifluoromethyl, pyrazolyl optionally substituted with 1-2 substituents independently selected from the group consisting of tolyl and $C_1$-$C_6$ alkyl that is optionally substituted with hydroxy, piperidinyl, pyrrolidinyl, or morpholinyl, ($C_1$-$C_6$ alkyl)isoxazolyl, ($C_1$-$C_6$ alkyl)thiazolyl, ($C_1$-$C_6$ alkyl)isothiazolyl, ($C_1$-$C_6$ alkyl)thiadiazolyl;

$R^7$ is H, or $C_1$-$C_6$ alkyl; or pharmaceutically acceptable salts thereof.

The compounds of the present invention are inhibitors of VEGF-R2, a protein kinase which has been shown to be involved in the angiogenic process. VEGF-R2, which is expressed primarily on endothelial cells, binds the potent angiogenic growth factor VEGF and mediates the subsequent signal transduction through activation of its intracellular kinase activity. Thus, one skilled in the art would recognize that direct inhibition of the kinase activity of VEGF-R2 will result in the reduction of angiogenesis and thus affect treatment of conditions wherein abnormal angiogenesis and/or increased vascular permeability is a hallmark, for example, diabetes (hyperglycemia), psoriasis, rheumatoid arthritis, Kaposi's sarcoma, haemangioma, acute and chronic nephropathies, atheroma, arterial restinosis, autoimmune diseases, acute inflammation, ocular diseases with retinal vessel proliferation, and cancer. The utility of angiogenesis inhibitors in the treatment of cancer is known in the literature, see J. Rak et al. *Cancer Research*, 55:4575-4580, 1995 for example. The role of angiogenesis in cancer has been shown in numerous types of cancer and tissues: Breast carcinoma (G. Gasparinin and A. L. Harris, *J. Clin. Oncol.*, 1995, 13:765-782; M. Toi et al. *Japan. J. Cancer Res.*, 1994, 85:1045-1049); bladder carcinomas (A. J. Dickinson et al., *Br. J. Urol.*, 1994, 74:762-766) colon carcinomas (L. M. Ellis et al., Surgery, 1996, 120(5): 871-878); and oral cavity tumors (J. K. Williams et al., *Am J. Surg.*, 1994, 168:373-380). Preferred neoplasms believed to be susceptible to treatment by compounds of the present invention include the following cancers: brain, genitourinary tract, lymphatic system, stomach, larynx, lung (including small cell and non-small cell), pancreas, breast, prostate, histiocytic, lymphoma, hepatocellular, gynecologic (e.g. ovarian), Kaposi's sarcoma, CNS tumors (including astrocytomas, medulloblastomas, and meningiomas), colorectal, head and neck cancer, melanoma, chronic lymphocytic leukemia, multiple myeloma, acute myeloid leukemia (AML), chronic myelogenous leukemia (CML), malignant mesothelioma, myelodysplastic syndrome" (e.g., polycythemia vera, thrombocytemia), gastric cancer, and renal cell carcinoma.

The skilled artisan will appreciate that the introduction of certain substituents will create asymmetry in the compounds of Formula I. The present invention contemplates all enantiomers and mixtures of enantiomers and stereoisomers, that is, both the stereomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers by well known methods, such as, chiral-phase high performance liquid chromatography or crystallizing the compound as a chiral salt complex. Enantiomers and stereoisomers can also be obtained from stereomerically- or enantiomerically-pure intermediates, reagents, and catalysts by well known asymmetric synthetic methods.

Pharmaceutically acceptable salts are contemplated to be within the scope of the present invention. The compounds of the present invention are bases and salts of such compounds may be formed with inorganic or organic acids, for example, HCl, diHCl, succinate, L-tartrate, and HBr with HCl, diHCl and succinate being preferred.

The compounds of this invention may be prepared by employing reactions as shown in the following schemes, in addition to other standard manipulations that are known in the literature or exemplified in the experimental procedures. These schemes, therefore, are not limited by the compounds listed or by any particular substituents employed for illustrative purposes.

The following schemes are used to prepare compounds of Formula I where $R^5$ is $NHC(O)CH_2R^6$ or $NHC(O)NHR^6$. Unless otherwise indicated, all other variables are as previously defined.

Scheme I

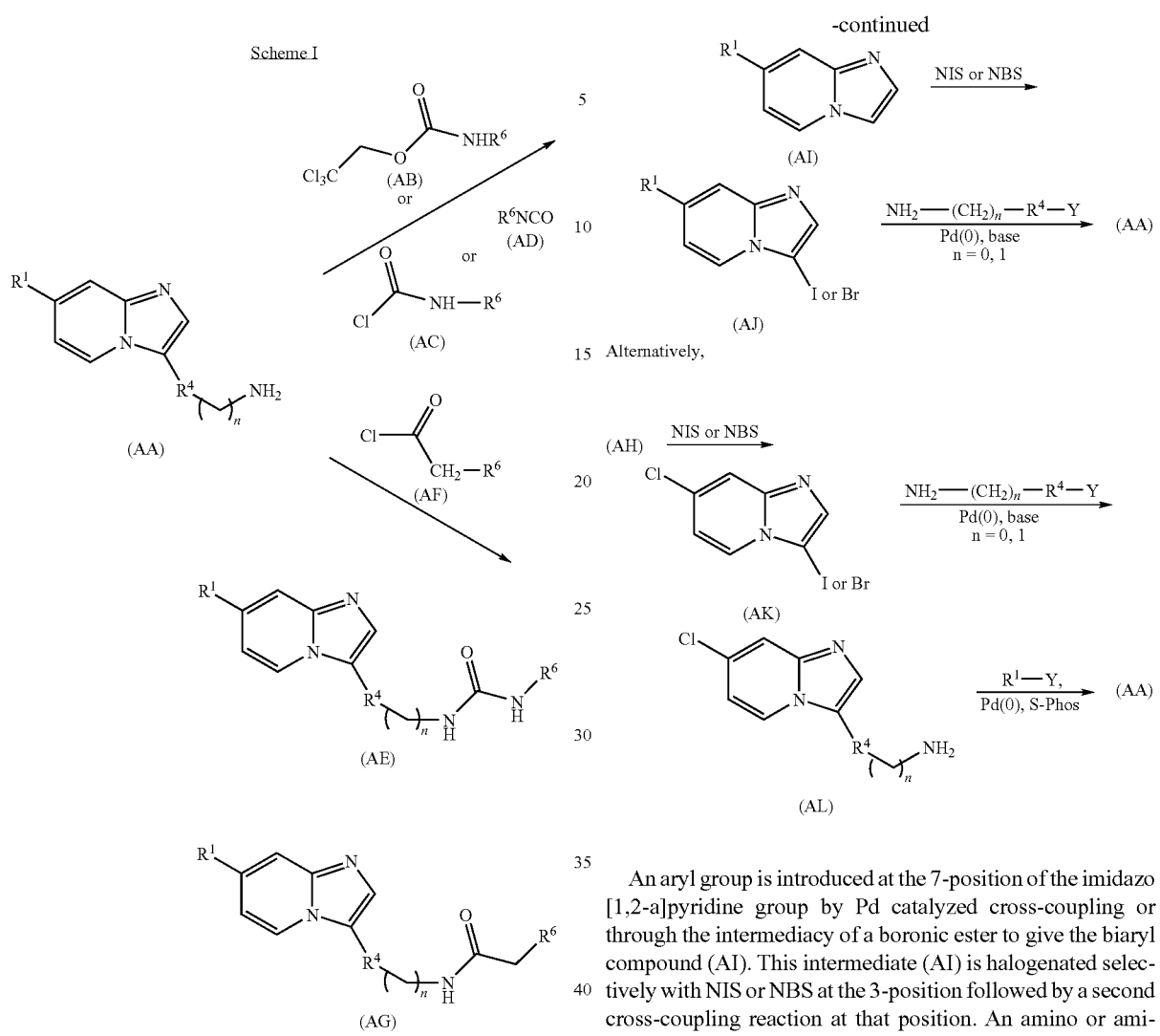

The urea (AE) compounds of Formula I may be generally prepared by reaction of an amine (AA) with a carbamate (AB), a carbamoyl chloride (AC), or an aryl isocyanate (AD), all of which are commercially available or directly prepared by methods known to those skilled in the art. The amide (AG) compounds of Formula I may be generally prepared by reaction of an amine (AA) with an acyl chloride (AF).

The requisite amine (AA) intermediate may be prepared from known 7-chloro-imidazo[1,2-a]pyridine (AH) as in Scheme II. X is Cl, Br, or I, and Y is a boronic acid, boronic ester, or trialkyl stannane. Unless otherwise indicated, all other variables are as previously defined.

An aryl group is introduced at the 7-position of the imidazo[1,2-a]pyridine group by Pd catalyzed cross-coupling or through the intermediacy of a boronic ester to give the biaryl compound (AI). This intermediate (AI) is halogenated selectively with NIS or NBS at the 3-position followed by a second cross-coupling reaction at that position. An amino or aminoalkyl group or a latent amino or aminoalkyl group is a substituent of the aryl boronate coupling partner. Alternatively, the couplings may be carried out first at the 3-position and then at the 7-position through the intermediacy of (AK) and (AL) as depicted in Scheme II. It should also be noted that the cross-coupling reaction used to install the aryl group at the 7-position of the imidazo[1,2-a]pyridine can take place at the end of the sequence, after formation of the urea (not pictured).

The amides of Formula I may be prepared as shown in Scheme III. Unless otherwise indicated, all variables are as previously defined.

Scheme II

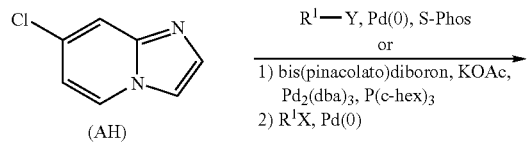

Scheme III

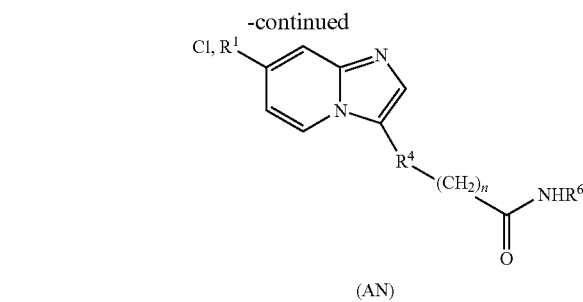

(AN)

Alternatively

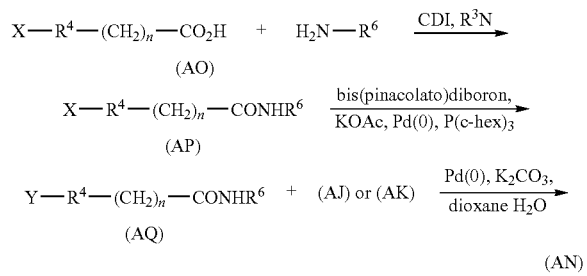

A Pd(0) catalyzed cross-coupling of (AJ) or (AK) with a phenyl boronic acid that is appended with an alkyl tethered carboxylic acid (or protected acid) provides (AM). The carboxylate group is coupled to an amine using standard methods well-known to those skilled in the art resulting in (AN). Alternatively, the amide (AP) can be prepared from a halophenyl acid (AO) using standard methods before the aryl group is coupled to the imidazo[1,2-a]pyridine ring. In this case a halide substituent on the aryl group (AP) is converted to a boronic ester (AQ) for coupling to (AJ) or (AK) as shown in Scheme III. In the cases where a halogen occupies the 7-position of the imidazo[1,2-a]pyridine ring in (AN), a second Pd(0) catalyzed coupling is carried out to obtain the claimed compound as previously described in Scheme I.

The carbamates of Formula I may be prepared as shown in Scheme IV. Unless otherwise indicated, all variables are as previously defined.

Scheme IV

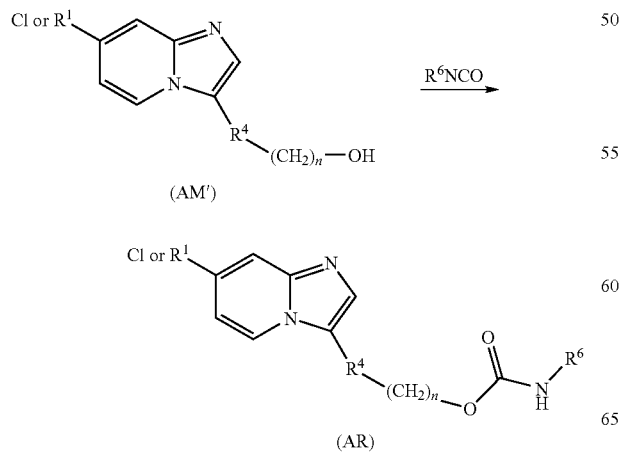

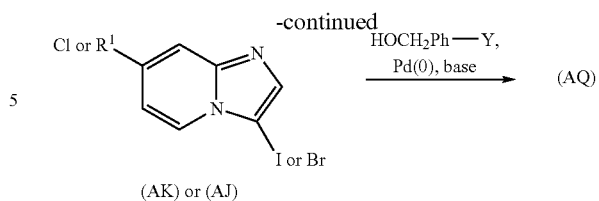

The carbamates (AR) are formed by combining an alcohol (AM') with an isocyanate. Synthesis of this starting material (AM') is by Pd(0) catalyzed cross-coupling at the 3-position of the imidazo[1,2-a]pyridine (AK or AJ) with an alcohol such as hydroxylmethylphenylboronic acid. The aryl group at the 7-position of the imidazo[1,2-a]pyridine can be introduced by a second Pd(0) coupling at any point as shown for the ureas.

Compounds of Formula I where $R^1$ is pyridonyl, methoxy substituted pyridinyl, or di(substituted)aminopyridinyl may be prepared as shown is Scheme V. Unless otherwised indicated, all other variables are as previously defined.

Scheme V

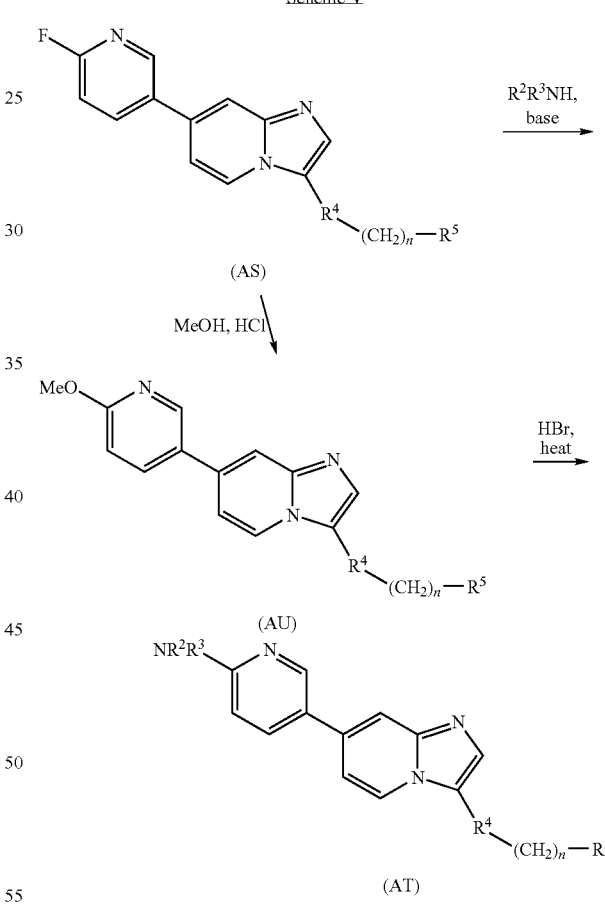

A dialkylamino group can be introduced by nucleophilic aromatic substitution of a 2-fluoropyridyl group (AS) to yield (AT) at the end of the synthesis. A similar strategy using acidic methanolysis gives (AU), and methyl ether cleavage with HBr provides the pyridonyl group (AV).

The aryl bromides of Scheme II, R¹X, may be prepared as described in Scheme VI. R⁷ is as previously described.

Scheme VI

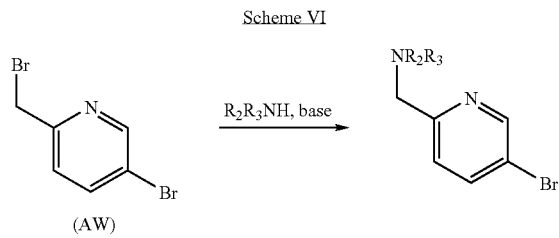

(AW)

An alkyl- or dialkylaminomethyl pyridyl group can be introduced as a substituent on the aryl group at the 7-position of the imidazo[1,2-a]pyridine via alkylation of 5-bromo-2-bromomethyl-pyridine (AW) with a secondary amine, as shown in Scheme VI. The aryl bromide (s) can then participate directly is the reactions previously described.

Scheme VII

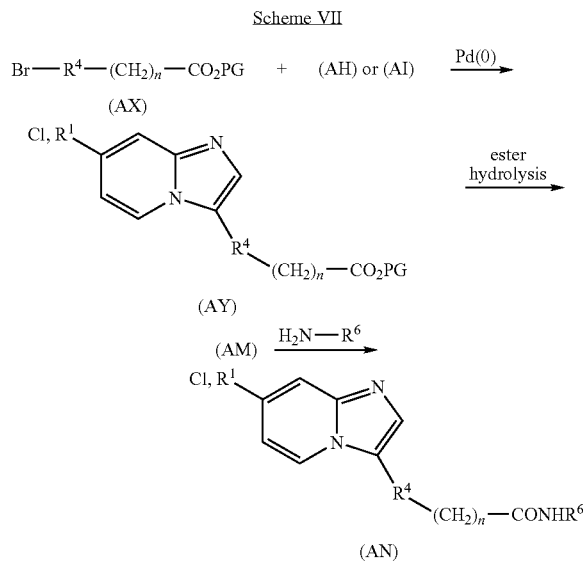

Compounds from the amide class may also be prepared as shown in Scheme VII via the Pd(0) catalyzed arylation reaction of 3-H imidazo[1,2,a]pyridine intermediates (AH) or (AI) with a protected (PG) bromophenyl acetic acid ester (AX) to form the coupled acid (AY). The tert-butyl group is a suitable ester protecting group indicated as PG which is subsequently cleaved under acidic conditions. The amide (AN) may then be formed using either oxalyl chloride/DMF to form an acyl chloride in situ or using the coupling reagents DMTMM/NMM or HATU/diisopropylethyl amine.

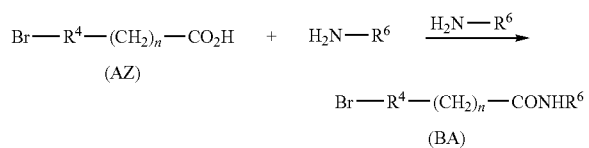

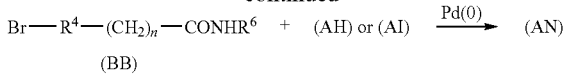

(BB)

Alternately, The amides (BA) are prepared from bromoarylacids (AZ) using the amide formation procedures above, and the BA are coupled via the Pd(0) catalyzed arylation reaction with (AH) or (AI). In the cases where the Pd(0) catalyzed arylation reaction is carried out with (AH), subsequent elaboration is carried out at the C1 substituted position as previously described.

The skilled artisan will appreciate that not all of the substituents in the compounds of Formula I will tolerate certain reaction conditions employed to synthesize the compounds. These moieties may be introduced at a convenient point in the synthesis, or may be protected and then deprotected as necessary or desired. The skilled artisan will appreciate that the protecting groups may be removed at any convenient point in the synthesis of the compounds of the present invention. Methods for introducing and removing nitrogen and oxygen protecting groups are well known in the art; see, for example, Greene and Wuts, *Protective Groups in Organic Synthesis*, 3$^{rd}$ Ed., John Wiley and Sons, New York, Chapter 7 (1999). Furthermore, the skilled artisan will appreciate that in many circumstances, the order in which moieties are introduced is not critical. The particular order of steps required to produce the compounds of Formula I can be dependent upon the particular compound being synthesized, the starting compound, and the relative lability of the substituted moieties.

Abbreviations

AIBN—2,2'-Azobis(2-methyl propionitrile); BINAP—rac-2,2'-Bis(diphenyl-phosphino)-1,1'-binaphthyl; 9-BBN—9-Borabicyclo[3.3.1]nonane; Boc₂O—Di-tert-butyl dicarbonate; TBDMSCl or TBDMSiCl—tert-butyl-dimethylsilyl chloride; TBAF—tert-Butylamine hydrofluoride; MS (ES)—Electrospray Mass spectrum; THF—tetrahydrofuran; DMEA—Dimethylethylamine; DMSO—Dimethylsulfoxide; DMF—Dimethylformamide; DME—Dimethyl ethylene glycol; DCM—dichloromethane; Dioxane—1,4-dioxane; DMAP—4-Dimethylaminopyridine; h—hour(s); LDA—Lawesson Reagent-2,4-Bis-(4-methoxy phenyl)-1,3-dithia-2,4-diphosphetone-2,4-disulfide; Lithium di-isopropylamine; NIS—N-iodosuccinimide; min—minute(s); NBS—N-romosuccinimide; MeOH—methanol; EtOH—95% ethanol; RBF, RB—round bottom flask; RBSN—round bottom single neck flask; SiO₂—silica gel; EtOAc, AcOEt—ethylacetate; ESIMS—electrospray ionization mass spectrometry; HPLC—high pressure liquid chromatography; ISCO—ISCO brand high pressure liquid chromatography; S-Phos—2-Dicyclohexyl-phosphino-2',6'-dimethoxy-1,1'-biphenyl; Pd(TPP)₄-tetralis(triphenylphosphine)-palladium (0); DMTMM—4-(4,6-dimethoxy-[1,3,5]triazin-2-yl)-4-methyl-morpholin-4-ium; chloride; NMM—N-Methylmorpholine; HATU—O-(7-Azabenzotriazole-1-yl)-N,N,N'N'-tetramethyluronium hexafluorophosphate; NMP—1-Methyl-2-pyrrolidinone; PdCl₂(dppf) CH₂Cl₂—1,1'-Bis-(diphenylphosphino)ferrocene palladium(II) dichloride Dichloromethane complex; X-Phos—2-Dicyclohexylphosphino-2',4',6'-tri-1-propyl-1,1'-biphenyl. NMP—1-

Methyl-2-pyrrolidinone; Pearlman's catalyst—Palladium hydroxide, 20 wt % Pd on carbon;

Preparation 1

5-tert-Butyl-2-[2-(tert-butyl-dimethyl-silanyloxy)-ethyl]-2H-pyrazol-3-ylamine

A. 2-(5-Amino-3-tert-butyl-pyrazol-1-yl)-ethanol

To a solution of 4,4-dimethyl-3-oxo-pentanenitrile (5.0 g, 0.04 mol) in absolute ethanol (50 mL), add 2-hydrazino-ethanol (3 mL, 1.1 equiv.) and concentrated HCl (0.5 mL). Reflux the reaction for 4 hours then cool to room temperature and dilute with water and ethyl acetate. Wash the organics with water then saturated aqueous saturated sodium chloride then dry with magnesium sulfate, filter and concentrate in vacuo. Trituration from hexanes and dichloromethane gives a white solid (4.8 g, 66%). MS (ES), m/z 184 (M+1).

B. 5-tert-Butyl-2-[2-(tert-butyl-dimethyl-silanyloxy)-ethyl]-2H-pyrazol-3-ylamine To 2-(5-amino-3-tert-butyl-pyrazol-1-yl)-ethanol (3.42 g, 0.019 mol), add TBDMSCl (3.38 g, 1.2 equiv.) and imidazole (3.18 g, 2.5 equiv.) in DMF (7 mL) and stir overnight at room temperature under $N_2$. Dilute the reaction with ethyl acetate and water. Wash the organic layer with water then saturated aqueous saturated sodium chloride and then dry over magnesium sulfate, filter, and concentrate in vacuo to give a solid (5.5 g, 99%) which is used without further purification. MS (ES), m/z 298 (M+1).

Make the following intermediates according to the general procedure described in the PCT application WO200026202 May 11, 2000, filed Oct. 27, 1999 (p. 52):

| Preparation | Name | Physical Data MS (ES), m/z (M + 1) |
| --- | --- | --- |
| 2 | 5-Ethyl-thiazol-2-ylamine | 129 |
| 3 | 5-Propyl-thiazol-2-ylamine | 143 |
| 4 | 5-Isopropyl-thiazol-2-ylamine | 143 |
| 5 | 5-tert-Butyl-thiazol-2-ylamine | 157 |

Preparation 6

2-[2-(tert-Butyl-dimethyl-silanyloxy)-ethyl]-(5-tert-butyl-2H-pyrazol-3-yl)-carbamic acid 2,2,2-trichloro-ethyl ester Dissolve 5-tert-butyl-2-[2-(tert-butyl-dimethyl-silanyloxy)-ethyl]-2H-pyrazol-3-ylamine (5.5 g, 0.018 mol) in THF (100 mL) under $N_2$ and cool to 0° C. Add pyridine (1.6 mL, 1.1 equiv.) via syringe followed by dropwise addition of 2,2,2-trichloroethyl chloroformate (2.7 mL, 1.1 equiv.). Stir the reaction at 0° C. for one hour then remove the cooling bath and allow the reaction to stir for a total of 5 hours. Dilute the reaction with ethyl acetate and water. Wash the organic layer with water then saturated aqueous saturated sodium chloride and then dry over magnesium sulfate, filter, and concentrate in vacuo to give a residue (8.7 g, 100%) that is used without further purification. MS (ES), m/z 474 (M+1).

Using a procedure similar to Preparation 6, prepare the following intermediates from commercially available starting materials or those described in Preparations 1-5:

| Prep. | Name | Physical Data MS (ES), m/z (M + 1) |
| --- | --- | --- |
| 7 | (3-tert-Butyl-isoxazol-5-yl)-carbamic acid 2,2,2-trichloro-ethyl ester | 317 |
| 8 | [3-(1-Ethyl-1-methyl-propyl)-isoxazol-5-yl]-carbamic acid 2,2,2-trichloro-ethyl ester | 345 |
| 9 | [3-(1,1-Dimethyl-butyl)-isoxazol-5-yl]-carbamic acid 2,2,2-trichloro-ethyl ester | 345 |
| 10 | (5-tert-Butyl-isoxazol-3-yl)-carbamic acid 2,2,2-trichloro-ethyl ester | 317 |
| 11 | (5-tert-Butyl-2-p-tolyl-2H-pyrazol-3-yl)-carbamic acid 2,2,2-trichloro-ethyl ester | 406 |
| 12 | 3-tert-Butyl-5-(2,2,2-trichloro-ethoxycarbonylamino)-pyrazole-1-carboxylic acid tert-butyl ester | 415 |
| 13 | (5-tert-Butyl-2-methyl-2H-pyrazol-3-yl)-carbamic acid 2,2,2-trichloro-ethyl ester | 328 |
| 14 | (5-tert-Butyl-[1,3,4]thiadiazol-2-yl)-carbamic acid 2,2,2-trichloro-ethyl ester | 332 |
| 15 | (5-Ethyl-thiazol-2-yl)-carbamic acid 2,2,2-trichloro-ethyl ester | 304 |
| 16 | (5-Propyl-thiazol-2-yl)-carbamic acid 2,2,2-trichloro-ethyl ester | 319 |
| 17 | (5-Isopropyl-thiazol-2-yl)-carbamic acid 2,2,2-trichloro-ethyl ester | 319 |
| 18 | (5-tert-Butyl-thiazol-2-yl)-carbamic acid 2,2,2-trichloro-ethyl ester | 333 |
| 19 | (4-tert-Butyl-thiazol-2-yl)-carbamic acid 2,2,2-trichloro-ethyl ester | 333 |
| 20 | (4-Trifluoromethyl-pyridin-2-yl)-carbamic acid 2,2,2-trichloro-ethyl ester | 339 |
| 21 | (4-sec-Butyl-pyridin-2-yl)-carbamic acid 2,2,2-trichloro-ethyl ester | 327 |

Preparation 22

3-Iodo-7-chloro-imidazo[1,2,a]pyridine

To a solution of 7-chloro-imidazo[1,2,a]pyridine (6.10 g, 40 mmol) (Yamanaka, Motosuke et al., Chemical & Pharmaceutical Bulletin (1991), 39(6), 1556-67) in dry acetonitrile (100 mL), add N-iodosuccinamide. Stir for 30 minutes. Filter off the precipitate and then wash with acetonitrile. Recrystallize the precipitate from acetonitrile to give a white solid. Concentrate the filtrate, dilute with ethyl acetate, wash with 10% sodium hydrogensulfite (NaHSO$_3$), saturated aqueous sodium bicarbonate, saturated aqueous NaCl, dry over MgSO$_4$, filter and evaporate. Use the combined solid without further purification (8.0 g, 73%). $^1$H NMR (DMSO) δ 8.33 (d, 1H, J=7.3 Hz), 7.79 (d, 1H, J=2.0 Hz), 7.72 (s, 1H), 7.07 (dd, 1H, J=7.3 and 2.0 Hz).

Preparation 23

4-(4,4,5,5-Tetramethyl-[1,3,2]dioxaborolan-2-yl)-pyrazole-1-sulfonic acid dimethylamide

A. Pyrazole-1-sulfonic acid dimethylamide

Dissolve 4-iodopyrazole 9.24 g, 48.0 mmol) in THF (100 mL) and add NaH (2.26 g, 63.6 mmol, 60% in oil) is portionwise and stir for 30 minutes at 0° C. Add dimethyl sulfamoyl chloride (6.18 mL, 57.6 mmol) dropwise and stir 1 hour at 0° C. and 1 hour at room temperature. Quench the reaction with saturated NaHCO$_3$ solution and extract with CH$_2$Cl$_2$, dry over anhydrous MgSO$_4$, filter and concentrate. Chromatograph the residue with hexanes/ethyl acetate 1:0 to 2:1 to give a clear oil (11.8 g, 82% yield). MS (ES), m/z 176 (M+1).

B. 4-(4,4,5,5-Tetramethyl-[1,3,2]dioxaborolan-2-yl)-pyrazole-1-sulfonic acid dimethylamide Combine pyrazole-1-sulfonic acid dimethylamide (7.0 g, 23.2 mmol), potassium acetate (6.3 g, 69.8 mmol), bis(pinacolato)diboron (6.5 g, 25.5 mmol), and DMSO (140 mL) and de-gas under a stream of nitrogen. Add PdCl$_2$(dppf).CH$_2$Cl$_2$ (0.51 g, 0.70 mmol and heat the reaction to 80° C. overnight. Dilute the reaction with water and extract with ethyl acetate. Wash the combined organics with water and dry over anhydrous MgSO4, filter and concentrate. Use the title compound contaminated by a 33% impurity of the bipyrazole as a mixture.

Preparation 24

4-Bromo-2-ethyl-pyridine

Prepare the title compound according to the general procedure described in *Journal Organic Chemistry*, Vol. 50, No. 22, 1985, page 4410-4411. Slurry 4-bromopyridine hydrochloride (4.17 g, 0.021 mol) in THF (100 mL) and cool to −78° C. under nitrogen. Add ethylmagnesium bromide (15.7 mL of a 3.0 M solution in diethyl ether, 2.2 equiv.) dropwise via syringe. Stir the reaction at −78° C. for 10 minutes then remove the ice bath and allow the reaction to warm to room temperature. Quench reaction with 20% ammonium chloride (aq) then dilute with diethyl ether. Wash organics with water, 1 N HCl (aq), then aqueous saturated sodium chloride. Dry organics over magnesium sulfate, filter and concentrate in vacuo. Redissolve the residue in toluene (100 mL) and place under nitrogen. Dissolve tetrachloro-1,2-benzoquinone (5.8 g, 1.1 equiv.) in acetic acid (50 mL) and add dropwise to the reaction. Allow reaction to stir overnight at room temperature. Make the mixture basic by adding 1 N NaOH (aq) then extract with ethyl acetate. Acidify organic layer with 1 N HCl (aq) and extract with ethyl acetate. Set organics aside. Basify the aqueous layer with 1 N NaOH (aq) and extract with DCM. Wash this organic layer with aqueous saturated sodium chloride then dry over magnesium sulfate. Filter and concentrate in vacuo to give a brown residue (2.64 g, 66%). LCMS (ES), m/z 188 (M+1, bromide pattern).

Prepare the following according to the same procedure as Preparation 24.

| Preparation | Name | Physical Data MS (ES), m/z (M + 1) |
|---|---|---|
| 25 | 4-Bromo-2-isopropyl-pyridine | 202 (M + 1, bromide pattern) |

Preparation 26

1-(4-Chloro-pyridin-2-yl)-propan-2-one

Make the title compound with a procedure similar to Preparation 162 A below using 4-chloro-2-methylpyridine. MS(ES), m/z 170 (M+1).

Preparation 27

3-Iodo-7-pyridin-2-yl-imidazo[1,2-a]pyridine

A. 7-Pyridin-2-yl-imidazo[1,2-a]pyridine

To a round bottomed flask add 7-chloro-imidazo[1,2-a]pyridine (0.25 g, 1.6 mmol), tricyclohexylphosphine (55 mg, 0.12 equiv.), potassium acetate (0.24 g, 1.5 equiv.), bis(pinacolato)diboron (0.46 g, 1.1 equiv.) and dioxane (10 mL). Deoxygenate this mixture thoroughly with N$_2$ then add tris (dibenzylideneacetone)dipalladium (0) (75 mg, 0.05 equiv.) and heat the reaction to 80° C. overnight under N$_2$. Filter the reaction thru Celite® and wash with DCM then concentrate to dryness. To this residue, add 2-bromopyridine (0.14 mL, 1.5 mmol), S-Phos (75 mg, 0.125 equiv.), potassium phosphate (0.62 g, 2 equiv.), dioxane (10 mL), and water (5 mL). Deoxygenate this mixture thoroughly with N$_2$, add palladium (II) acetate (16 mg, 0.05 equiv.), and reflux the reaction overnight. Concentrate the reaction to dryness and slurry in DCM. Filter this slurry thru Celite® and wash with DCM. Concentrate the filtrate then purify by silica column (EtOAc to 5% MeOH:DCM) to give a residue (0.325 g, >100%). MS (ES), m/z 196 (M+1).

B. 3-Iodo-7-pyridin-2-yl-imidazo[1,2-a]pyridine

Dissolve 7-pyridin-2-yl-imidazo[1,2-a]pyridine (0.3 g, 1.5 mmol) in absolute ethanol (10 mL) and add NIS (0.35 g, 1 equiv.). Heat the reaction to 50° C. for 30 minutes under N$_2$ then dilute with ethyl acetate. Wash the organic layer with 1 N NaOH followed by sat NaCl. Dry the organic layer over magnesium sulfate, filter and concentrate to give a light tan solid (0.4 g, 82%). MS (ES), m/z 322 (M+1).

Prepare the following according to procedures similar to Preparation 27:

| Preparation | Name | Physical Data MS (ES), m/z (M + 1) |
|---|---|---|
| 28 | 3-Iodo-7-(2-methyl-2H-[1,2,4]triazol-3-yl)-imidazo[1,2-a]pyridine | 326 |
| 29 | 3-Iodo-7-(2-methyl-pyridin-4-yl)-imidazo[1,2-a]pyridine | 336 |
| 30 | 7-(3-Fluoro-pyridin-4-yl)-3-iodo-imidazo[1,2-a]pyridine | 340 |
| 31 | 7-(2-Chloro-pyridin-4-yl)-imidazo[1,2-a]pyridine | 232 |
| 32 | 7-[2-(3,3-Diethoxy-propyl)-pyridin-4-yl]-3-iodo-imidazo[1,2-a]pyridine | 452 |
| 33 | 3-Iodo-7-(2-isopropyl-pyridin-4-yl)-imidazo[1,2-a]pyridine | 364 |
| 34 | 3-Iodo-7-(2-ethyl-pyridin-4-yl)-imidazo[1,2-a]pyridine | 350 |
| 35 | 1-(4-Imidazo[1,2-a]pyridin-7-yl-pyridin-2-yl)-propan-2-one | 252 |
| 36 | 3-Iodo-7-(pyridin-2-yl)-imidazo[1,2-a]pyridine | 322 |
| 37 | 7-(6-Methyl-pyridin-2-yl)-imidazo[1,2-a]pyridine | 210 |

Preparation 38

4-(3-Bromo-imidazo[1,2-a]pyridin-7-yl)-1-(3-piperidin-1-yl-propyl)-1H-pyridin-2-one A. 4-Imidazo[1,2-a]pyridin-7-yl-1H-pyridin-2-one Prepare this intermediate by methods similar to Preparation 27 except using 4-bromo-2-fluoro pyridine as a coupling partner MS (ES), m/z 214 (M+1). Heat the intermediate 2-fluoropyridine in a round bottom flask with 5N HCl under $N_2$ atmosphere to 80° C. for 2 hours. Cool, add 50 mL 2 M $NH_3$ in MeOH and DCM transfer to separatory funnel and extract with DCM (10×). Filter aqueous layer and combine with DCM extracts strip off DCM under reduced pressure to give 1.26 g (26% overall) MS(ES), m/z 212 (M+1).

B. 4-Imidazo[1,2-a]pyridin-7-yl-1-(3-piperidin-1-yl-propyl)-1H-pyridin-2-one

In a RBF under nitrogen, charge (850 mg, 4.0 mmols), 1-(3-chlororpropyl)piperine HCl (1.18 g, 6 mmol), DMF (40 mL), and $Cs_2CO_3$ (2.8 g, 8.8 mmols), NaI (450 mg, 3 mmol) and heat to 78° C. for 24 hours. Filter the reaction and rinse the solids with DCM. Combine DCM and filtrate and strip off under reduced pressure then purify by passing through Varian SCX® (10 g) column that is pre-washed with water and methanol, the product being eluted with (20%) 2 N $NH_3$ in methanol/(80%) DCM. Evaporate solvent from the product containing fractions under reduced pressure. Chromatograph using (40 g ISCO®) $SiO_2$ eluting with a gradient of 0% to 10% 2 M $NH_3$ in MeOH with the balance DCM. Evaporate solvents to afford ivory solid 410 mg (30%) MS(ES), m/z 337 (M+1).

C. 4-(3-Bromo-imidazo[1,2-a]pyridin-7-yl)-1-(3-piperidin-1-yl-propyl)-1H-pyridin-2-one Prepare the title compound in a similar fashion as in Preparation 78 B with the exception that EtOH and acetonitrile are used as solvents. MS(ES), m/z 415, 417 Br isotopes (M+1).

Preparation 39

7-[2-(3,3-Diethoxy-propyl)-pyridin-4-yl]-imidazo[1,2-a]pyridine

In a round bottomed flask, add 9-BBN (0.5 M in THF, 42.2 mL, 2 equiv.) under nitrogen. Add acrolein diethyl acetal (3.4 mL, 2.1 equiv.) via syringe and stir at room temperature overnight. In a separate flask on the second day, combine 7-(2-chloro-pyridin-4-yl)-imidazo[1,2-a]pyridine (2.42 g, 11 mmol), potassium phosphate (4.47 g, 2 equiv.), S-Phos (0.54 g, 12.5 mol %), dioxane (90 mL), and water (45 mL). De-gas with nitrogen then add palladium (II) acetate (0.118 g, 5 mol %) under nitrogen. To this solution add the material from the first flask via canula. Heat the reaction at 80° C. for 5.5 hours. Concentrate to dryness. Slurry in DCM then filter to remove insoluble material. Wash with DCM. Concentrate filtrate and purify by silica plug (1:1 Hexanes:Ethyl Acetate→Ethyl Acetate→5% Methanol:DCM→10% Methanol:DCM) to give a residue (4.15 g, >100%) which is used as is for the next step. MS (ES), m/z 326 (M+1).

Preparation 40

7-[2-(2-Morpholin-4-yl-propyl)-pyridin-4-yl]-imidazo[1,2-a]pyridine

Dissolve 1-(4-imidazo[1,2-a]pyridin-7-yl-pyridin-2-yl)-propan-2-one (3.9 g, 15.5 mmol) in methanol (400 mL) under nitrogen. Add morpholine hydrochloride (38.4 g, 20 equiv.) followed by 3 Å Sieves (7.8 g, powdered and dried in a vacuum oven at 100° C. overnight). Stir five minutes then add sodium cyanoborohydride (1.0 M in THF, 28 mL, 1.8 equiv.) via syringe and stir at room temperature for 5 days. Filter to remove insoluble material, washing with methanol. Concentrate to dryness then make basic with 20% NaOH (aq) and extract with ethyl acetate. Wash organics with aqueous saturated sodium chloride then dry over $MgSO_4$. Filter and concentrate then purify by silica gel (Ethyl Acetate→5% Methanol:DCM→10% Methanol:DCM→5% 2M $NH_3$ in methanol:DCM→10% 2 M $NH_3$ in Methanol:DCM) to give product as a tan solid (3.7 g, 74%). MS (ES), m/z 323 (M+1).

Prepare the following using procedures similar to Preparation 40:

| Preparation | Name | Physical Data MS (ES), m/z (M + 1) |
|---|---|---|
| 41 | 2-(4-Imidazo[1,2-a]pyridin-7-yl-pyridin-2-yl)-1-methyl-ethylamine | 253 |

Preparation 42

[2-(4-imidazo[1,2-a]pyridin-7-yl-pyridin-2-yl)-1-methyl-ethyl]-carbamic acid tert-butyl ester Dissolve 2-(4-imidazo[1,2-a]pyridin-7-yl-pyridin-2-yl)-1-methyl-ethylamine (0.1 g, 0.4 mmol) in a mixture of THF (10 mL) and DCM (10 mL) under nitrogen. Add di-tert-butyl-dicarbonate (0.095 g, 1.1 equiv.). Stir 45 minutes at room temperature then dilute with ethyl acetate. Extract organics with water, 1 N NaOH (aq), then aqeuous sodium chloride. Dry organics over $MgSO_4$, then filter and concentrate. Purify by silica gel (10% Methanol:DCM) to give product (0.125 g, 89%). MS (ES), m/z 353.2 (M+1).

Preparation 42A

3-Iodo-7-(4-methanesulfonyl-phenyl)-imidazo[1,2-a]pyridine

A. 7-(4-Methanesulfonyl-phenyl)-imidazo[1,2-a]pyridine

Heat a mixture of 7-chloro-imidazo[1,2-a]pyridine (100 g, 152.5 mmol, 1 eq), 4-methylsulfonylphenyl boronic acid (157.3 g, 786.8 mmol, 1.2 eq), $Pd(PPh_3)_4$ (19 g, 16.3 mmol, 0.025 eq) and cesium carbonate (472.4 g, 1.44 mol, 2.2 eq) in a mixture of anhydrous DME (2000 mL) and EtOH (1000 mL) at 80° C. under $N_2$ atmosphere for 24 hours. Cool the mixture to room temperature and filter through Celite® to remove Pd catalyst. Add water (5000 mL) and extract this solution with $CH_2Cl_2$ (3×2000 mL). Dry the organic phase over $MgSO_4$ and evaporate. Add to the crude 2000 mL of $CH_2Cl_2$ and heat to reflux. Remove insoluble materials by filtration and evaporate the solvent to afford a yellow solid. Wash the solid with ethyl ether to give 150 g of the desired compound as a light yellow solid. (Yield: 85%). MS (ES), m/z 273 (M+1).

B. 3-Iodo-7-(4-methanesulfonyl-phenyl)-imidazo[1,2-a]pyridine

Treat a solution of 7-(4-methanesulfonyl-phenyl)-imidazo[1,2-a]pyridine (101 g, 371.3 mmol, 1 eq) in 2000 mL of $CH_3CN$ at 0° C. with NIS (83.5 g, 371.3 mmol, 1 eq). Allow the mixture to stir at room temperature for 1 hour. Remove the solvent and the dissolve the residue in 5000 mL of $CH_2Cl_2$, wash with 10% NaOH solution, $NaHSO_3$ sat., water and aqueous saturated sodium chloride. Dry over $MgSO_4$ and evaporate. Triturate the solid obtained with hexanes, filter and dry in vacuo to afford 110 g of the title compound as a yellow solid. (Yield: 75%). MS (ES), m/z 399 (M+1).

Preparation 43

4-(3-Iodo-imidazo[1,2-a]pyridin-7-yl)-benzoic acid methyl

Prepare the title compound using a similar procedure as the one for the preparation of 3-iodo-7-(4-methanesulfonyl-phenyl)-imidazo[1,2-a]pyridine. MS(ES), m/z 379 (M+1).

Preparation 44

4-[7-(4-Methanesulfonyl-phenyl)-imidazo[1,2-a]pyridin-3-yl]-benzylamine

Combine 3-iodo-7-(4-methanesulfonyl-phenyl)-imidazo[1,2-a]pyridine (2.50 g, 6.28 mmol), (4-aminomethylphenyl) boronic acid, HCl (1.29 g, 6.91 mmol) and $K_2CO_3$ (3.47 g, 25.11 mmol) in 1,4-dioxane (30 mL) and water (15 mL). Bubble nitrogen through the mixture for five minutes. Add dichlorobis(triphenylphosphine) palladium (II) (0.132 g, 0.188 mmol). Attach a reflux condenser, and heat the mixture to 110° C. Stir overnight (15 hours), and cool to room temperature. Concentrate the mixture to dryness in vacuo. Slurry the resulting solid into dichloromethane/methanol and filter through Celite® 521. Concentrate the solution in vacuo to a yellow solid. Purify by column chromatography (ethyl acetate→5% methanol in dichloromethane→10% methanol in dichloromethane→10% 2 M $NH_3$ in methanol in dichloromethane) to afford product (1.57 g, 66%). MS(ES), m/z 378 (M+1).

Prepare the following according to Preparation 44:

| Preparation | Compound Name | Physical Data MS (ES), m/z (M + 1) |
|---|---|---|
| 45 | 4-[7-(4-Methanesulfonyl-phenyl)-imidazo[1,2-a]pyridin-3-yl]-phenylamine | 364 |
| 46 | 4-(7-Pyridin-2-yl-imidazo[1,2-a]pyridin-3-yl)-phenylamine | 287 |
| 47 | 4-[7-(1H-[1,2,3]Triazol-4-yl)-imidazo[1,2-a]pyridin-3-yl]-phenylamine | 277 |
| 48 | 4-[7-(2-Methyl-2H-[1,2,4]triazol-3-yl)-imidazo[1,2-a]pyridin-3-yl]-phenylamine | 291 |
| 49 | 4-[7-(2-Methyl-2H-[1,2,4]triazol-3-yl)-imidazo[1,2-a]pyridin-3-yl]-benzylamine | 305 |
| 50 | 4-(3-{4-[3-(5-tert-Butyl-isoxazol-3-yl)-ureido]-3-fluoro-phenyl}-imidazo[1,2-a]pyridin-7-yl)-benzoic acid | 514 |
| 51 | 4-[3-(4-Amino-3-fluoro-phenyl)-imidazo[1,2-a]pyridin-7-yl]-benzoic acid | 348 |
| 52 | 4-(7-Pyridin-3-yl-imidazo[1,2-a]pyridin-3-yl)-benzylamine | 301 |
| 53 | 4-(7-Pyridin-2-yl-imidazo[1,2-a]pyridin-3-yl)-benzylamine | 301 |
| 54 | 4-[7-(2-Methyl-pyridin-4-yl)-imidazo[1,2-a]pyridin-3-yl]-benzylamine | 315 |

Preparation 55

4-(7-Pyridin-3-yl-imidazo[1,2-a]pyridin-3-yl)-phenylamine

A. 4-(7-Chloro-imidazo[1,2-a]pyridin-3-yl)-phenylamine

To a round bottomed flask add 7-chloro-3-iodo-imidazo[1,2-a]pyridine (3.0 g, 0.011 mol), add 4-(4,4,5,5-tetramethyl-1,3,2-dioxaborolan-2-yl)aniline (2.6 g, 1.1 equiv.), potassium carbonate (4.5 g, 3 equiv.), dioxane (40 mL), and water (20 mL). Deoxygenate this mixture thoroughly with $N_2$ then add dichlorobis(triphenylphosphine)palladium (II) (0.23 g, 0.03 equiv.) and reflux the reaction overnight under $N_2$. Concentrate the reaction to dryness and slurry in DCM. Filter this slurry thru Celite® and wash with DCM. Concentrate the filtrate then purify by silica plug (EtOAc to 5% MeOH: DCM to 10% MeOH: DCM) to give a pale grey solid (2.6 g, 100%). MS (ES), m/z 244 (M+1).

B. 4-(7-Pyridin-3-yl-imidazo[1,2-a]pyridin-3-yl)-phenylamine

To a round bottomed flask add 4-(7-chloro-imidazo[1,2-a]pyridin-3-yl)-phenylamine (0.5 g, 2.1 mmol), pyridine-3-boronic acid (0.38 g, 1.5 equiv.), potassium phosphate (0.87 g, 2 equiv.), 2-dicyclohexylphosphino-2',6'-dimethoxy-1,1'-biphenyl (also called S-Phos, 0.105 g, 0.125 equiv.), 1,4-dioxane (10 mL), and water (5 mL). Deoxygenate this mixture thoroughly with $N_2$ then add palladium (II) acetate (23 mg, 0.05 equiv.) and reflux the reaction overnight. Concentrate the reaction to dryness and slurry in DCM. Filter this slurry thru Celite® and wash with DCM. Concentrate the filtrate then purify by silica plug (EtOAc to 5% MeOH: DCM to 10% MeOH: DCM) to give a yellow solid (0.39 g, 66%). MS (ES), m/z 287 (M+1).

Prepare the following according to procedures similar to Preparation 55:

| Preparation | Compound Name | Physical Data MS (ES), m/z (M + 1) |
|---|---|---|
| 56 | 4-(7-Pyridin-4-yl-imidazo[1,2-a]pyridin-3-yl)-benzylamine | 301 |
| 57 | 3-(7-Pyridin-4-yl-imidazo[1,2-a]pyridin-3-yl)-benzylamine | 301 |
| 58 | [4-(7-Pyridin-4-yl-imidazo[1,2-a]pyridin-3-yl)-benzyl]-carbamic acid tert-butyl ester | 401 |
| 59 | 4-(7-Thien-3-yl-imidazo[1,2-a]pyridin-3-yl)-benzonitrile | 302 |
| 60 | 3-(7-Thien-3-yl-imidazo[1,2-a]pyridin-3-yl)-benzonitrile | 302 |
| 61 | 4-Imidazo[1,2-a]pyridin-7-yl-pyrazole-1-sulfonic acid dimethylamide | 292 |

Preparation 62

4-(7-Thien-3-yl-imidazo[1,2-a]pyridin-3-yl)-benzylamine

Dissolve 4-(7-thien-3-yl-imidazo[1,2-a]pyridin-3-yl)-benzonitrile (0.087 g, 0.29 mmol) in THF (8 mL). To the solution add a $BH_3.Me_2S$ solution (2 M, 1.0 mL, 2.0 mmol) at room temperature. Stir the solution for 15 minutes and then heat at 50° C. for 3.5 hours. Cool the mixture at 0° C. and acidify to pH=1 slowly and stir for 30 minutes. Make the reaction mixture basic with solid NaOH to pH=12-14, followed by extraction with ethyl acetate. Wash the extracts with saturated aqueous saturated sodium chloride, dry over $MgSO_4$, filter and evaporate to afford 0.070 g. MS(ES), m/z 306 (M+1).

Prepare the following according to procedures similar to Preparation 62:

| Preparation | Compound Name | Physical Data MS (ES), m/z (M + 1) |
|---|---|---|
| 63 | 3-(7-Thien-3-yl-imidazo[1,2-a]pyridin-3-yl)-benzylamine | 306 |

Preparation 64

4-(7-Pyridin-4-yl-imidazo[1,2-a]pyridin-3-yl)-phenylamine

A. 7-Pyridin-4-yl-imidazo[1,2-a]pyridine Method A

Charge a 250 mL round bottom flask equipped with a magnetic stirrer, temperature controlled heating mantle, under $N_2$ atmosphere, condenser, with 7-chloro-imidazo[1,2-a]pyridine (4.0 g, 26.2 mmol), 4-pyridyl boronic acid (3.54 g, 28.8 mmol 1.1 Eq), 2-dicyclohexylphosphino-2',6'-dimethoxy-1,1'-biphenyl (600 mg) [X-Phos can be used as an alternate ligand in this reaction], $Pd(OAc)_2$ (145 mg), $K_3PO_4$ (11.1 g, 52.6 mmol), and dioxane: $H_2O$ 2:1 (170 mL). Warm the reaction while purging with a $N_2$ needle, then heat to 65° C. for 18 hours. Cool the reaction to room temperature and transfer to a separatory funnel and siphon off the bottom layer (25 mL). Add EtOAc and evaporate the solvents under reduced pressure off. Take the solids up into EtOAc again, and evaporate under reduced pressure to azeotrope off traces of water. Dissolve the brown solid into $CH_2Cl_2$ and 5% MeOH and then chromatograph using $SiO_2$ eluting with a slow gradient of 0% to 10% of 2 M $NH_3$ in MeOH with the balance $CH_2Cl_2$. Evaporate the product fractions under reduced pressure to give a light yellow/tan solid 4.5 g (89%). MS (ES), m/z 196 (M+1).

A. 7-Pyridin-4-yl-imidazo[1,2-a]pyridine Method B

1) To a 250 mL round-bottom flask under nitrogen, charge 7-chloro-imidazo[1,2-a]pyridine (5.07 g, 33.2 mmol, 1 eq), bis(pinacolato)diboron (10.18 g, 40.1 mmol, 1.2 eq), potassium carbonate (6.86 g, 49.6 mmol, 1.5 eq), $Pd(OAc)_2$ (370 mg, 1.6 mmol, 0.05 eq), tricyclohexylphosphine (914 mg, 3.3 mmol, 0.10 eq), diglyme (50 mL), and water (68 μL). Heat the reaction mixture to 100° C. for 24 hours, then stir over the weekend at room temperature. Filter the mixture and rinse with 2×10 mL diglyme. Slurry the solids in 50 mL water for 1 hour, then filter and rinse 2×10 mL water. Dry the wet cake (~10 g) in vacuo at 60° C. overnight to give the title compound as a gray solid (6.54 g, 26.8 mmol, 81% yield) with a purity of 99.3% by HPLC.

2) To a 100 mL round-bottom flask with stir bar and condenser, under nitrogen, charge 4-bromopyridine hydrochloride (3.98 g, 20.5 mmol, 1 eq), 7-(4,4,5,5-tetramethyl-[1,3,2]dioxaborolan-2-yl)-imidazo[1,2-a]pyridine (5.47 g, 22.4 mmol, 1.1 eq), $Pd(OAc)_2$ (90 mg, 401 mmol, 0.02 eq), triphenylphosphine (217 mg, 827 mmol, 0.04 eq), $K_3PO_4$ (8.6 g, 40.5 mmol, 2 eq), 1-propanol (36 mL), and water (12 mL). Heat this reaction mixture to reflux (90° C.) overnight and then cool to room temperature. Separate the layers and add 40 mL MTBE and 40 mL 1 M HCl to the PrOH layer. Wash the aqueous layer with 40 mL MTBE and rinse twice with 6 mL 1-propanol. Add methanol (4 mL) to the aqueous layer, which is heated to 45° C. before adding 9 mL of 5 M NaOH. Cool the reaction mixture, and seed at 25° C. Filter the reaction mixture after 1.5 hours and rinse with 2×4 mL water with 10% MeOH, then with 8 mL MTBE (to help get the water out of the cake and ease drying). Dry the solids in vacuo at 60° C. Isolate the title as a yellow solid (2.90 g) in 73% yield with 98% purity by HPLC (at 215 nm).

B. 3-Iodo-7-pyridin-4-yl-imidazo[1,2-a]pyridine

Charge a 250 µL round bottom flask equipped with: a magnetic stirrer, temperature controlled heating mantle, $N_2$ atmosphere, with 7-pyridin-4-yl-imidazo[1,2-a]pyridine (3.35 g, 17.2 mmol), NIS (3.8 g, 16.8 mmol), EtOH (3A). Heat the reaction to 65° C. for 1 hour. This can be followed by $SiO_2$ TLC (100% EtOAc). Add more NIS (3.8 g, 16.8 mmol) and heat the reaction to 65° C. for 1 hour. Mix the reaction while cooling in an ice bath for 30 minutes then filter and rinse the solids with MeOH. Air dry the solids and vacuum oven dry at 40° C. to afford 4.59 g (83%). Additional product can be obtained from the filtrate. MS (ES), m/z 322 (M+1).

C. 4-(7-Pyridin-4-yl-imidazo[1,2-a]pyridin-3-yl)-phenyl amine

Charge a 250 mL round bottom flask equipped with a magnetic stirrer, temperature controlled heating mantle, under a $N_2$ atmosphere, condenser, with 3-iodo-7-pyridin-4-yl-imidazo[1,2-a]pyridine (4.95 g, 15.4 mmol), 4-amino phenyl boronic acid (1.07 g), 4-(4,4,5,5-tetramethyl-1,3,2-dioxanborolan-2-yl)aniline (2.69 g) [these combined give (18.5 mmols 1.2 equivalents) total of boronic acid], dimethoxy ethane (140 mL), 2 M $K_2CO_3$ (40 mL, 28.8 mmol, 1.1 eq), and Pd(PPh$_3$)$_4$ (836 mg). Warm the reaction while purging with $N_2$, then heat to 65° C. for 18 hours. Cool the reaction to room temperature and transfer to a separatory funnel and siphon off the bottom layer (25-30 mL). Evaporate the DME under reduced pressure off and take the residue up into MeOH (1 L), and 2 M $NH_3$ in MeOH (10 mL). Filter the solution to remove Pd(0) and evaporate under reduced pressure to coat onto $SiO_2$ gel. Vacuum dry the $SiO_2$ and chromatograph using $SiO_2$ eluting with a gradient of 0% to 10% of 2 M $NH_3$ in MeOH with the balance $CH_2Cl_2$. Evaporate the solvents under reduced pressure affording a bright yellow solid 2.6 g (60%). MS (ES), m/z 286 (M+1).

Prepare the following according to Preparation 64:

| Preparation | Compound Name | Physical Data MS (ES), m/z (M + 1) |
|---|---|---|
| 65 | 4-(7-Chloro-imidazo[1,2-a]pyridin-3-yl)-phenylamine | 244 |
| 66 | 4-(7-Chloro-imidazo[1,2-a]pyridin-3-yl)-benzylamine | 258 |
| 67 | 4-(7-Thiazol-2-yl-imidazo[1,2-a]pyridin-3-yl)-benzylamine | 307 |
| 68 | 3-Iodo-7-pyridin-3-yl-imidazo[1,2-a]pyridine | 322 |
| 69 | {2-[4-(3-Iodo-imidazo[1,2-a]pyridin-7-yl)-pyridin-2-yl]-1-methyl-ethyl}-carbamic acid tert-butyl ester | 479 |
| 70 | 3-Iodo-7-(6-methyl-pyridin-3-yl)-imidazo[1,2-a]pyridine | 336 |

Preparation 71

1-(5-Bromo-pyridin-2-yl)-3-(5-tert-butyl-isoxazol-3-yl)-urea

Dissolve (5-tert-butyl-isoxazol-3-yl)-carbamic acid 2,2,2-tichloro-ethyl ester (0.480 g, 1.52 mmol, 1.0 eq.) and 5-bromo-pyridin-2-yl amine (0.263 g, 1.52 mmol, 1.0 eq.) in DMSO (2.0 mL). Add triethyl amine (0.22 mL, 1.52 mmol, 1.0 eq.). Stir the reaction mixture at 80° C. for about 16 hours, cool, then dilute with diethyl ether (100 mL), wash with saturated aqueous saturated sodium chloride (2×20 mL), water (2×20 mL), dry, filter, and concentrate to produce a brown oil. Purify the oil by silica gel flash chromatography employing a 0-10% gradient of ethyl acetate in dichloromethane to furnish 0.302 g (58%) of the title compound as a brown solid. MS (ES), m/z 339, 341 (M+1).

Prepare the following according to procedures similar to Preparation 71:

| Preparation | Name | Physical Data MS (ES), m/z (M + 1) |
|---|---|---|
| 72 | 1-(4-Bromo-phenyl)-3-(5-tert-butyl-2H-pyrazol-3-yl)-urea | 339 |

The following intermediates are prepared using essentially the same procedure as for Example 64 below:

| Preparation | Name | Physical Data MS (ES), m/z (M + 1) |
|---|---|---|
| 73 | 1-(4-Bromo-2-fluoro-phenyl)-3-(5-tert-butyl-isoxazol-3-yl)-urea | 356, 358 |
| 74 | 1-(4-Bromo-2-fluoro-phenyl)-3-(5-tert-butyl-isothiazol-3-yl)-urea | 372, 374 |

Preparation 75

{4-[7-(6-Fluoro-pyridin-3-yl)-imidazo[1,2-a]pyridin-3-yl]-benzyl}-carbamic acid tert-butyl ester

A. [4-(7-Chloro-imidazo[1,2-a]pyridin-3-yl)-benzyl]-carbamic acid tert-butyl ester Add to a suspension of 3-iodo-7-chloro-imidazo[1,2-a]pyridine (4.80 g, 17.2 mmol, 1.0 eq) in dioxane (90 mL) 2 M Na$_2$CO$_3$ (30 mL) and (4-aminomethylphenyl)-boronic acid (3.88 g, 20.7 mmol, 1.2 eq.). Deoxygenate the mixture and fill with nitrogen. Add tetrakis (triphenylphosphine) palladium (0.50 g, 0.43 mmol, 0.025 eq). Deoxygenate the reaction mixture and fill with nitrogen. Stir the reaction mixture at 85° C. for three days. Add (Boc)$_2$O (4.51 g, 20.7 mmol, 1.2 eq.) and stir the mixture at 60° C. for 20 minutes. Concentrate the mixture to dryness in vacuo. Slurry the resulting solid into dichloromethane/methanol and filter through Celite®521. Concentrate the solution in vacuo to a yellow solid (5.60 g). Employ silica gel flash chromatography using a 0-4% MeOH/DCM gradient to afford 4.50 g (12.6 mmol, 73%) of the title compound as a slightly yellow solid as product. MS(ES), m/z 358 (M+1).

B. {4-[7-(6-Fluoro-pyridin-3-yl)-imidazo[1,2-a]pyridin-3-yl]-benzyl}-carbamic acid tert-butyl ester Suspend [4-(7-chloro-imidazo[1,2-a]pyridin-3-yl)-benzyl]-carbamic acid tert-butyl ester (1.90 g, 5.30 mmol, 1.0 eq.) in dioxane/water (2:1, 36 mL). Add 2-fluoro-5-pyridine boronic acid (0.75 g, 5.30 mmol, 1.0 eq.), K$_3$PO$_4$ (2.25 g, 10.6 mmol, 2.0 eq.), and S-phos (0.272 g, 0.66 mmol, 0.125 eq.). Deoxygenate the mixture and fill with nitrogen. Add Pd(OAc)$_2$ (0.059 g, 0.265 mmol, 0.05 eq.). Deoxygenate the reaction mixture and fill with nitrogen. Stir the reaction at 80° C. under nitrogen for 16 hours. A white solid is formed after the solution is cooled down. Filter off the white solid, wash with water (3×15 mL), EtOAc (3×15 mL). Collect the solid (1.50 g). Purify the filtrate by silica gel flash chromatography with a 0-5% MeOH/DCM gradient to afford the title compound (0.52 g) as a slightly yellow solid. Combine the chromatography product and the filtered solids to give slightly yellow solid. (2.02 g, 4.83 mmol) MS(ES), m/z 419 (M+1).

Prepare the following according to procedures similar to Preparation 75:

| Preparation | Name | Physical Data MS (ES), m/z (M + 1) |
|---|---|---|
| 76 | {5-[3-(4-Amino-phenyl)-imidazo[1,2-a]pyridin-7-yl]-pyridin-2-yl}-dimethyl-amine | 405 |
| 77 | 4-[7-(6-Fluoro-pyridin-3-yl)-imidazo[1,2-a]pyridin-3-yl]-phenylamine | 305 |

Preparation 78

4-(7-Thiazol-2-yl-imidazo[1,2-a]pyridin-3-yl)-phenylamine

A. 7-thiazol-2-yl-imidazo[1,2-a]pyridine

In a 500 mL round bottom flask, stir a suspension of 7-chloro-imidazo[1,2-a]pyridine (7.5 g, 49.2 mmol) in 250 mL 1,4-dioxane with bis(pinacolato)diboron (13.74 g, 54.1 mmol, 1.1 eq), potassium acetate (7.24 g, 73.8 mmol, 1.5 eq) and tricyclohexylphosphine (1.66 g. 5.9 mmol, 0.12 eq). Deoxygenate the resulting slurry with two cycles of evacuation and bubbling nitrogen through the slurry for 10 minutes each. Fit the flask with a reflux condenser and add tris(dibenzylidineacetone)dipalladium (0) (2.25 g, 2.45 mmol, 0.05 eq) and stir the mixture under nitrogen at 80° C. overnight. Filter the hot mixture over a ~1 cm pad of celite, wash with 50 mL 1,4-dioxane, then concentrate the combined filtrate and wash to give a brown pasty solid. Suspend a portion of the solid (32.8 mmol) in 80 mL of dioxane, combine with 41.25 mL of 2 M aqueous sodium carbonate (82.5 mmol, 2.5 eq) and 2-bromothiazole (4.38 mL, 8.07 g, 49.2 mmol, 1.5 eq), then deoxygenate twice via evacuation and bubbling nitrogen through the suspension. Add tetrakis (triphenylphosphine) palladium (1.89 g, 1.64 mmol, 0.05 eq), fit the flask with a reflux condenser and stir the mixture under nitrogen at 100° C. overnight. Filter the dark brown-black hot mixture through a 1 cm pad of Celite®, wash with 50 mL dioxane, then apply the combined filtrate and wash equally to three 25 g SCX Mega Bond-Elut™ SCX cartridges (Varian) each pre-washed with 200 mL 1:1 CH$_2$Cl$_2$:MeOH. After loading with vacuum assist, wash each cartridge with 300 mL 1:1 CH$_2$Cl$_2$:MeOH, then elute with 160 mL 1:1 CH$_2$Cl$_2$:2 M NH$_3$-MeOH. Concentrate the combined eluates in vacuo and purify through a 330 g silica gel cartridge using a 0 to 5% methanol gradient in dichloromethane. Concentrate the pooled clean fractions and dry to yield 3 g (45%) of 7-thiazol-2-yl-imidazo[1,2-a]pyridine as a tan solid. MS (ES) mm/z 202, (M+1).

B. 3-Bromo-7-thiazol-2-yl-imidazo[1,2-a]pyridine

Dissolve 7-thiazol-2-yl-imidazo[1,2-a]pyridine (1.14 g, 5.66 mmol) in 25 mL absolute ethanol, then add NBS (1.0 g, 5.66 mmol), stir the mixture at room temperature for 15 minutes, dilute with 35 mL dichloromethane and apply to a 10 g SCX Mega Bond-Elut™ cartridge (Varian) pre-washed with 150 mL 1:1 CH$_2$Cl$_2$:MeOH. Wash the SCX cartridge with 300 mL 1:1 CH$_2$Cl$_2$:MeOH, elute with 150 mL CH$_2$Cl$_2$:2 M NH$_3$-MeOH, and concentrate the eluates and dry to provide 1.07 g (67%) of the title compound as a tan solid. MS (ES) 280, 282.

C. 4-(7-Thiazol-2-yl-imidazo[1,2-a]pyridin-3-yl) phenylamine

Take up 3-bromo-7-thiazol-2-yl-imidazo[1,2-a]pyridine (1.07 g, 3.82 mmol) and 4-aminophenylboronic acid hydrochloride (793 mg, 4.58 mmol, 1.2 eq) in 15 mL of dioxane and 7 mL of 2 N aqueous sodium carbonate, then deoxygenate with vacuum/nitrogen bubbling as described above. Add tetrakis (triphenylphosphine) palladium (0) (221 mg, 0.19 1 mmol, 0.05 eq), fit the reaction flask with a reflux condenser and heat the mixture to 95° C. with stirring under nitrogen for approximately 16 hours. Cool the dark brown reaction mixture, dilute with ethyl acetate (~40 mL) and partition the layers in a separatory funnel. Dry the organic layer over solid magnesium sulfate, filter, then apply to a 10 g SCX Mega Bond-Elut™ cartridge (Varian) prewashed with 100 mL 1:1 CH$_2$Cl$_2$:MeOH. After loading, wash the cartridge with another 200-250 mL of the CH$_2$Cl$_2$:MeOH solution, then elute the product with 100 mL of CH$_2$Cl$_2$:2 M NH$_3$-MeOH, concentrate to a brown-orange oil, and purify via flash chromatography with a gradient of 0 to 5% methanol in dichloromethane. Pool the clean fractions and concentrate to provide 750 mg (67%) of the title compound as a yellow-brown solid after drying. MS (ES) m/z 293 (M+1).

Preparation 79

2-Chloro-4-(7-pyridin-4-yl-imidazo[1,2-a]pyridin-3-yl)-phenylamine

A. 2-Chloro-4-(4,4,5,5-tetramethyl-[1,3,2]dioxaborolan-2-yl)-phenylamine

Dissolve 4-bromo-2-chloro-phenylamine (4.2 g, 20 mmol) in dioxane (80 mL) in a RBF under nitrogen. Add triethylamine (10 mL, 3.6 equiv.) then sparge with nitrogen to degas. Add 4,4,5,5-tetramethyl-[1,3,2]dioxaborolane (8.5 mL, 2.9 equiv.) dropwise via syringe over approximately 5 minutes. Sparge an additional 5 minutes with nitrogen then add [1,1'-Bis(diphenyl-phosphino)ferrocene] dichloropalladium (II) (0.603 g, 3.7 mol %, 1:1 complex with dichloromethane). Place under nitrogen and heat at 80° C. overnight. After the reaction cools, filter via Celite® washing with hexanes. Concentrate filtrate to dryness and use crude.

B. 2-Chloro-4-(7-pyridin-4-yl-imidazo[1,2-a]pyridin-3-yl)-phenylamine

Combine 3-iodo-7-pyridin-4-yl-imidazo[1,2-a]pyridine (2.18 g, 6.8 mmol), 2-chloro-4-(4,4,5,5-tetramethyl-[1,3,2] dioxaborolan-2-yl)-phenylamine (crude material from previous step, excess), potassium carbonate (2.8 g, 3 equiv.), dioxane (30 mL), and water (15 mL). De-gas thoroughly with nitrogen then add dichloro-bis(triphenylphosphine) palladium (II) (0.143 g, 3 mol %). Heat reaction at 80° C. overnight. Concentrate to dryness then slurry in DCM and filter via Celite®, washing with DCM. Concentrate filtrate then purify by silica plug (Hexanes→1:1 Hexanes:Ethyl Acetate→2.5% Methanol:DCM→5% Methanol:DCM) to give an orange-yellow solid (1.42 g, 46%). MS (ES), m/z 321.1 (M+1).

Prepare the following according to procedures similar to the above:

| Preparation | Name | Physical Data MS (ES), m/z (M + 1) |
|---|---|---|
| 80 | 4-(7-Pyridin-4-yl-imidazo[1,2-a]pyridin-3-yl)-2-trifluoromethyl-phenylamine | 355 |
| 81 | 4-[7-(2-Methyl-pyridin-4-yl)-imidazo[1,2-a]pyridin-3-yl]-2-trifluoromethyl-phenylamine | 369 |

Preparation 82

3-{4-[7-(4-Methanesulfonyl-phenyl)-imidazo[1,2-a]pyridin-3-yl]-phenyl}-propionic Combine 3-iodo-7-(4-methanesulfonyl-phenyl)-imidazo [1,2-a]pyridine (125.0 mg, 0.314 mmol, 1.0 equiv) with [4-(2-carboxyethyl)phenylboronic acid (122 mg, 0.628 mmol, 2.0 equiv) in the presence of tetrakis(triphenylphoshine)palladium (0) (36.3 mg, 0.031 mmol, 0.10 equiv), and sodium carbonate (99.8 mg, 0.942 mmol, 3.0 equiv) in DME and water mixture (1:1) (4 mL) in a 2-5 mL reaction volume microwave vessel. Seal the reaction vessel with a septum then place in the microwave cavity. Stir the mixture for 20 seconds then use microwave irradiation to raise the temperature from room temperature to 100° C. Once desired temperature is reached, hold the reaction mixture at this temperature for 3 hours. Allow the reaction vessel to cool to room temperature before opening. Apply the reaction mixture to SCX resin, which is eluted with dichloromethane, methanol, then 2.0 M ammonia in methanol. Concentrate the methanolic ammonia fraction to dryness under reduced pressure using a rotary evaporator. Carry forward the residue (139.0 mg) without additional purification. MS (ES) m/z 421 (M+1)

Prepare the following according to procedures similar to Preparation 82:

| Preparation | Compound Name | Physical data MS (ES) m/z (M + 1) |
|---|---|---|
| 83 | 3-{3-[7-(4-Methanesulfonyl-phenyl)-imidazo[1,2-a]pyridin-3-yl]-phenyl}-propionic acid | 421 |

Preparation 84

2-[4-(4,4,5,5-Tetramethyl-[1,3,2] dioxaborolan-2-yl)-phenyl]-N-(3-trifluoromethyl-phenyl)-acetamide

A. 2-(4-Bromo-phenyl)-N-(3-trifluoromethyl-phenyl)-acetamide

Dissolve 4-bromophenylacetic acid (10.00 g, 46.50 mmol), diisopropylethylamine (12.02 g, 16.20 mL, 93.00 mmol) and 1,1'-carbonyldiimidazole (8.29 g, 51.15 mmol) in tetrahydrofuran (200 mL) at room temperature. Stir the contents under nitrogen for one hour. Add m-trifluoromethylaniline (15.00 g, 93.00 mmol) and stir the reaction overnight at room temperature. Concentrate the reaction to near dryness, dissolve in dichloromethane (250 mL) and extract with 2 N NaOH (200 mL), water (100 mL) and 1 N HCl (2×200 mL). Wash the organic layer with saturated aqueous saturated sodium chloride (100 mL), dry over MgSO₄, filter and concentrate. Dry load the material onto silica (100 g) and chromatograph on silica using dichloromethane as eluent to yield the product (13.00 g, 78.1%). MS(ES), m/z 356/358 (M+1).

B. 2-[4-(4,4,5,5-Tetramethyl-[1,3,2]dioxaborolan-2-yl)-phenyl]-N-(3-trifluoromethyl-phenyl)-acetamide Dissolve 2-(4-bromo-phenyl)-N-(3-trifluoromethyl-phenyl)-acetamide (3.00 g, 8.38 mmol), bis(pinacolato)diboron (2.65 g, 10.48 mmol), potassium acetate (1.23 g, 12.57 mmol), and tricyclohexyl-phosphine (295 mg, 1.05 mmol) in anhydrous dioxane (95 mL). Deoxygenate the reaction contents with nitrogen for 10 minutes at room temperature. Add palladium acetate (II) (95 mg, 0.42 mmol) to the reaction. Fit a reflux condenser and heat the reaction mixture to 80° C. for 15 hours. Cool the reaction and dilute with ethyl acetate (200 mL). Extract/wash the ethyl acetate solution with water (3×100 mL), dry over MgSO₄, filter and concentrate to dryness. Dissolve the crude solid in warm dichloromethane, and slowly add hexane. Upon cooling, crystals form; add additional hexanes to the organics and after sitting for two hours, filter the suspension to yield the product (3.00 g, 88.5%). Wash with hexanes. MS(ES), m/z 404 (M−1).

Prepare the following according to procedures similar to Preparation 49:

| Preparation | Compound Name | Physical Data MS (ES), m/z |
|---|---|---|
| 85 | 4-[4-(4,4,5,5-Tetramethyl-[1,3,2]dioxaborolan-2-yl)-phenyl]-N-(3-trifluoromethyl-phenyl)-butyramide | 432 (M − 1) |

-continued

| Preparation | Compound Name | Physical Data MS (ES), m/z |
|---|---|---|
| 86 | N-(5-tert-Butyl-isoxazol-3-yl)-2-[4-(4,4,5,5-tetramethyl-[1,3,2]dioxaborolan-2-yl)-phenyl]-acetamide | 385 (M + 1) |
| 87 | N-(5-tert-Butyl-2-methyl-2H-pyrazol-3-yl)-2-[4-(4,4,5,5-tetramethyl-[1,3,2]dioxaborolan-2-yl)-phenyl]-acetamide | 398 (M + 1) |
| 88 | N-(5-tert-Butyl-[1,3,4]thiadiazol-2-yl)-2-[4-(4,4,5,5-tetramethyl-[1,3,2]dioxaborolan-2-yl)-phenyl]-acetamide | 402 (M + 1) |
| 89 | 2-[4-(4,4,5,5-Tetramethyl-[1,3,2]dioxaborolan-2-yl)-phenyl]-N-(4-trifluoromethyl-pyridin-2-yl)-acetamide | 407 (M + 1) |
| 90 | 2-[2-Fluoro-4-(4,4,5,5-tetramethyl-[1,3,2]dioxaborolan-2-yl)-phenyl]-N-(3-trifluoromethyl-phenyl)-acetamide | 408 (M + 1) |
| 91 | N-(5-tert-Butyl-thiazol-2-yl)-2-[2-fluoro-4-(4,4,5,5-tetramethyl-[1,3,2]dioxaborolan-2-yl)-phenyl]-acetamide | 419 (M + 1) |

Preparation 92

N-(4-Chloro-3-trifluoromethyl-phenyl)-2-[4-(4,4,5,5-tetramethyl-[1,3,2]dioxaborolan-2-yl)-phenyl]-acetamide A. 2-(4-Bromo-phenyl)-N-(4-chloro-3-trifluoromethyl-phenyl)-acetamide Dissolve 4-bromophenylacetic acid (25.39; 118.07 mmol) in ether (200 mL). Add anhydrous pyridine (1 mL) and cool the reaction to 0° C., then add oxalyl chloride (18.44 g, 12.86 mL, 145.32 mmol). After 15 minutes, allow the reaction to come to ambient temperature. At 1.5 hours, add DMF (0.4 mL) and stir for an additional hour. Concentrate to a thick amber oil. Dilute with dichloromethane (118 mL) to provide a 1 N stock solution of (4-bromo-phenyl)-acetyl chloride (118 mmol).

Dissolve 4-chloro-3-trifluoromethylaniline (4.13 g, 21.1 mmol) in anhydrous dichloromethane (21 mL) with N,N-diisopropylethylamine (13.57 g, 18.29 mL, 105 mmol) and cool to 0° C. Add to the aniline in the ice cold solution the stock acid chloride solution in dichloromethane (21.1 mL) dropwise. Stir overnight at ambient temperature. Dilute further with dichloromethane (100 mL) and wash with 1 N HCl (1×50 mL), water (1×50 mL), 1 N NaOH (2×50 mL), and aqueous saturated sodium chloride (50 mL). Dry organics over MgSO$_4$, filter and then concentrated to provide crude amide. Chromatograph on silica using 1:1 of (15% ethyl acetate in dichloromethane)/hexanes. Recrystallize from dichloromethane/hexanes. (2.78 g, 7.08 mmol, 42.2%). MS(ES), m/z 390/392 (M+1).

B. N-(4-Chloro-3-trifluoromethyl-phenyl)-2-[4-(4,4,5,5-tetramethyl-[1,3,2]dioxaborolan-2-yl)-phenyl]-acetamide Use a procedure similar to that for Preparation 84. MS(ES), m/z 438 (M−1).

Prepare the following according to procedures similar to Preparation 92:

| Preparation | Name | Physical Data MS (ES), m/z (M + 1) |
|---|---|---|
| 93 | N-(5-tert-Butyl-thiazol-2-yl)-2-[4-(4,4,5,5-tetramethyl-[1,3,2]dioxaborolan-2-yl)-phenyl]-acetamide | 402 |
| 94 | 2-[2-Chloro-4-(4,4,5,5-tetramethyl-[1,3,2]dioxaborolan-2-yl)-phenyl]-N-(3-trifluoromethyl-phenyl)-acetamide | 440 |
| 95 | N-(5-tert-Butyl-isoxazol-3-yl)-2-[2-chloro-4-(4,4,5,5-tetramethyl-[1,3,2]dioxaborolan-2-yl)-phenyl]-acetamide | 419 |
| 96 | 2-[2-Chloro-4-(4,4,5,5-tetramethyl-[1,3,2]dioxaborolan-2-yl)-phenyl]-N-(4-trifluoromethyl-pyridin-2-yl)-acetamide | 441 |

Preparation 97

4-[4-(7-Chloro-imidazo[1,2-a]pyridin-3-yl)-phenyl]-N-(3-trifluoromethyl-phenyl)-butyramide Suspend 4-[4-(4,4,5,5-tetramethyl-[1,3,2]dioxaborolan-2-yl)-phenyl]-N-(3-trifluoromethyl-phenyl)-butyramide (0.47 g, 1.15 mmol), 7-chloro-3-iodo-imidazo[1,2-a]pyridine (0.29 g, 1.05 mmol) and solid potassium carbonate (0.48 g, 3.45 mmol) in dioxane (4 mL) and water (2 mL). Deoxygenate the reaction contents with nitrogen for 10 minutes at room temperature. Add trans-dichlorobis(triphenylphosphine)palladium (II) (22 mg, 0.03 mmol) to the reaction. Fit a reflux condenser and heat the reaction to 105° C. over the weekend. Cool the reaction, dilute with dichloromethane and filter through Celite®. Concentrate the filtrate and then chromatograph on silica, using 0-3% methanol/ethyl acetate, to yield the product (301 mg, 57%). MS(ES), m/z 458 (M+1).

Prepare the following according to procedures similar to Preparation 97:

| Preparation | Compound Name | Physical Data MS (ES), m/z (M + 1) |
|---|---|---|
| 98 | N-(5-tert-Butyl-thiazol-2-yl)-2-[4-(7-chloro-imidazo[1,2-a]pyridin-3-yl)-2-fluoro-phenyl]-acetamide | 443 |

Preparation 99

C-{4-[7-(4-Methanesulfonyl-phenyl)-imidazo[1,2-a]pyridin-3-yl]-thiazol-2-yl}-methylamine A. [4-(7-Chloro-imidazo[1,2-a]pyridin-3-yl)-thiazol-2-ylmethyl]-carbamic acid tert-butyl ester To a solution of (4-trimethylstannyl-thiazol-2-ylmethyl)-carbamic acid tert-butyl ester (0.480 g, 1.27 mmol, 1.0 eq.) [prepared as in the PCT application WO2004046101, Jun. 3, 2004, filed Nov. 10, 2003] in anhydrous dioxane (4 mL), add 7-chloro-3-iodo-imidazo[1,2-a]pyridine (0.354 g, 1.27 mmol, 1.0 eq.) and LiCl (0.162 g, 3.0 eq.). Add Pd(PPh$_3$)$_4$ (0.102 g, 0.07 eq.). Deoxygenate the reaction mixture and fill with nitrogen. Stir at 90° C. over night, cool, then dilute with 5% MeOH/DCM (100 mL), wash with saturated aqueous saturated sodium chloride (2×20 mL), water (2×20 mL), dry, filter, and concentrate. Chromatograph on silica gel first with a 50%-100% EtOAc/DCM gradient then a 5% MeOH/DCM gradient to afford 0.180 g of the title compound, which is used in the next step without further purification: MS(ES), m/z 365 (M+1).

B. {4-[7-(4-Methanesulfonyl-phenyl)-imidazo[1,2-a]pyridin-3-yl]-thiazol-2-ylmethyl}-carbamic acid tert-butyl ester To a suspension of [4-(7-chloro-imidazo[1,2-a]pyridin-3-yl)-thiazol-2-ylmethyl]-carbamic acid tert-butyl ester (0.180 g, 0.49 mmol, 1.0 eq.) in dioxane/water (2:1, 6 mL), add 4-(methylsulphonyl)-benzeneboronic acid (0.108 g, 1.1 eq.), K$_3$PO$_4$ (0.208 g, 2.0 eq.), S-phos (0.025 g, 12.5% eq.) and Pd(OAc)$_2$ (0.006 g, 0.05 eq.). Deoxygenate the reaction mixture and fill with nitrogen and stir at 100° C. for 4 hours. Cool the mixture to room temperature and dilute with 5:95 MeOH/DCM (100 mL). Wash the mixture with saturated aqueous saturated sodium chloride (2×20 mL), water (2×20 mL), dry, filter, and concentrate. Purify the residue on silica gel with a 0-80% EtOAc/Hexane gradient, then with 5:95 MeOH/DCM to give 0.160 g of the title compound as a slightly yellow solid.

C. {4-[7-(4-Methanesulfonyl-phenyl)-imidazo[1,2-a]pyridin-3-yl]-thiazol-2-yl}-methylamine To a solution of {4-[7-(4-methanesulfonyl-phenyl)-imidazo[1,2-a]pyridin-3-yl]-thiazol-2-ylmethyl}-carbamic acid tert-butyl ester (0.160 g, 0.33 mmol, 1.0 eq.) in 1:1 MeOH/DCM (20 mL), add HCl (4 M in dioxane, 6 mL). Stir the reaction mixture at room temperature for 3 hours, then at 60° C. for 2 hours. Evaporate the reaction mixture under vacuum and use without further purification.

Preparation 100

2-[4-(7-Chloro-imidazo[1,2-a]pyridin-3-yl)-phenyl]-N-(3-trifluoromethyl-phenyl)-acetamide Couple 3-iodo-7-chloro-imidazo[1,2,a]pyridine (655 mg, 2.35 mmol) and 2-[4-(4,4,5,5-Tetramethyl-[1,3,2]dioxaborolan-2-yl)-phenyl]-N-(3-trifluoromethyl-phenyl)-acetamide (1.00 g, 2.47 mmol) using a procedure similar to Preparation 99B. MS(ES), m/z 430 (M+1).

Prepare the following according to procedures similar to Preparation 100:

| Preparation | Compound Name | Physical Data MS (ES), m/z (M + 1) |
|---|---|---|
| 101 | N-(5-tert-Butyl-isoxazol-3-yl)-2-[4-(7-chloro-imidazo[1,2-a]pyridin-3-yl)-phenyl]-acetamide | 409 |

Preparation 102

7-Iodo-imidazo[1,2-a]pyridine

Combine 4-iodo-pyridin-2-ylamine (4.00 g, 18.18 mmol) and chloroacetaldehyde (2.77 mL, 21.82 mmol) in ethanol (40 mL). Attach a reflux condenser, and heat the mixture to 83° C., stir overnight (15 hours), and cool to room temperature. Filter the resulting solution to yield the product as a tan solid (1.40 g, 32%). MS(ES), m/z 245 (M+1)

Preparation 103

7-Ethynyl-imidazo[1,2-a]pyridine

A. 7-[(Triisopropylsilanyl)-ethynyl]-imidazo[1,2-a]pyridine

Combine 7-iodo-imidazo[1,2-a]pyridine (2.64 g, 10.82 mmol), ethynyl-triisopropyl-silane (3.61 mL, 16.23 mmol), copper (I) iodide (0.103 g, 0.541 mmol) and triethylamine (7.54 mL, 54.09 mmol) in 1,4-dioxane (50 mL). Bubble nitrogen through the mixture for five minutes. Add [1,1'-Bis(diphenyl-phosphino)ferrocene] dichloropalladium(II) (0.442 g, 0.541 mmol, 1:1 complex with dichloromethane). Attach a reflux condenser, and heat the mixture to 85° C., stir overnight (15 hours), and cool to room temperature. Filter the mixture through Celite® 521. Concentrate the solution in vacuo to a dark brown oil and use as is. MS(ES), m/z 299 (M+1).

B. 7-Ethynyl-imidazo[1,2-a]pyridine

Combine 7-[(Triisopropylsilanyl)-ethynyl]-imidazo[1,2-a]pyridine (3.23 g, 10.82 mmol) and tetrabutylammonium fluoride (1.19 mL, 1.19 mmol, 1.0 M in THF) in THF (5 mL). Stir the mixture at room temperature for 40 minutes, then concentrate in vacuo to a black oil. Purify by column chromatography (ethyl acetate) to afford product (1.10 g, 71%). MS(ES), m/z 143.1 (M+1).

Preparation 104

7-(1H-[1,2,3]Triazol-4-yl)-imidazo[1,2-a]pyridine

Combine 7-ethynyl-imidazo[1,2-a]pyridine (1.10 g, 7.74 mmol), copper (I) iodide (0.074 g, 0.387 mmol), and trimethylsilyl azide (1.53 mL, 11.61 mmol) in a 9:1 mixture of DMF:methanol (13.8 mL) in a pressure flask. Seal the flask with a Teflon screw cap and heat the reaction mixture to 100° C., stir overnight (15 hours), and cool to room temperature. Concentrate the mixture to dryness in vacuo. Slurry the resulting solid into dichloromethane and filter through Celite® 521. Concentrate the solution in vacuo to an orange solid. Purify by column chromatography (ethyl acetate→5% methanol in dichloromethane→8% methanol in dichloromethane) to afford product (0.82 g, 57%). MS(ES), m/z 186 (M+1).

Preparation 105

3-Iodo-7-(1H-[1,2,3]triazol-4-yl)-imidazo[1,2-a]pyridine

Use a procedure similar to Preparation 27B with 7-(1H-[1,2,3]triazol-4-yl)-imidazo[1,2-a]pyridine to give the title compound MS(ES), m/z 312 (M+1).

Preparation 106

7-(2,6-Dimethyl-pyridin-4-yl)-imidazo[1,2-a]pyridine

Prepare from 7-iodo-imidazo[1,2,a]pyridine and 4-bromo-2,6-dimethylpyridine (Acta. Chemica. Scandinavica. B42, (1988) pages 373-377) using a procedure similar to Preparation 27A. MS(ES), m/z 224 (M+1).

Preparation 107

5-(1-Methyl-cyclopropyl)-[1,3,4]thiadiazol-2-ylamine

Combine 1-methylcyclopropane-1-carboxylic acid (10.00 g, 99.88 mmol), and thiosemicarbazide (9.10 g, 99.88 mmol) in dioxane (110 mL). Heat the mixture to 90° C. under $N_2$, then add phosphorus(III) oxychloride (9.14 mL, 99.88 mmol) dropwise over 25 minutes. The reaction mixture is stirred for 6 hours at 90° C., then 8 hours at room temperature. Decant onto 200 g ice and add ammonium hydroxide to make basic. Filter to remove solids; the filtrate is extracted with ethyl acetate. The organic layer is washed with water. Dry the resulting organics over magnesium sulfate, filter, and concentrate to give product (2.54 g, 16%). MS (ES), m/z 156 (M+1).

Preparation 108

4-Dimethylaminomethyl-5-(1-methyl-cyclopropyl)-thiazol-2-ylamine dihydrochloride

A. 2-Amino-5-(1-methyl-cyclopropyl)-thiazole-4-carboxylic acid methyl ester Combine (1-Methyl-cyclopropyl)-methanol (5.00 g, 58.05 mmol), 4-methylmorpholine N-oxide (10.20 g, 87.08 mmol) and 4 angstrom sieves (5.6 g) in $CH_2Cl_2$ (200 mL). Stir the reaction mixture for 20 minutes at room temperature under $N_2$. Add tetrapropylammonium perruthenate (1.02 g, 2.90 mmol) and stir for 5 hours. Purify on a plug of silica gel; elute with $CH_2Cl_2$. Combine fractions containing product and concentrate in vacuo; some $CH_2Cl_2$ remains. Carry this material on directly to the next reaction step.

Combine 1-Methyl-cyclopropanecarbaldehyde (4.88 g, 58.01 mmol) and methyldichloroacetate (5.46 mL, 52.74 mmol) in diethyl ether (20 mL); cool to 0° C. Add dropwise a solution of sodium (1.21 g, 52.74 mmol) in methanol (20 mL). Stir the reaction mixture for 4 hours at 0° C. under $N_2$. Extract the mixture with diethyl ether versus water. Dry the resulting organics over magnesium sulfate, filter, and concentrate to a clear liquid. Combine the liquid with thiourea (4.42 g, 58.01 mmol) in methanol (25 mL). Heat the reaction mixture for 14 hours at 60° C. under $N_2$. Concentrate in vacuo and purify on a plug of silica gel, eluting with hexanes→3% methanol in dichloromethane→5% methanol in dichloromethane to afford product (5.10 g, 46% over two steps). MS (ES), m/z 213 (M+1).

B. 2-tert-Butoxycarbonylamino-5-(1-methyl-cyclopropyl)-thiazole-4-carboxylic acid Combine 2-Amino-5-(1-methyl-cyclopropyl)-thiazole-4-carboxylic acid methyl ester (5.10 g, 24.03 mmol) and di-tert-butyl dicarbonate (5.24 g, 24.03 mmol) in pyridine (15 mL). Stir the reaction mixture for 1 hour, then add a solution of potassium trimethylsilanolate (17.12 g, 120.13 mmol) in THF (100 mL). Stir the reaction mixture for 14 hours under $N_2$. Extract the mixture with ethyl acetate versus 1 N HCl. The organic layer is washed with aqueous saturated sodium chloride. The resulting organics are dried over magnesium sulfate, filtered, and concentrated. Purify on a plug of silica gel, eluting with hexanes→5% methanol in dichloromethane to afford product (4.55 g, 64%). MS (ES), m/z 243 (M+1, product—tert-butyl).

C. [4-Hydroxymethyl-5-(1-methyl-cyclopropyl)-thiazol-2-yl]-carbamic acid tert-butyl ester Dissolve 2-tert-butoxycarbonylamino-5-(1-methyl-cyclopropyl)-thiazole-4-carboxylic acid (2 g, 6.7 mmol) in THF (100 mL) and cool to 0° C. under nitrogen. Add triethylamine (0.93 mL, 1 equiv.) followed by the dropwise addition of isobutyl chloroformate (0.87 mL, 1 equiv.). Stir 30 minutes at 0° C. then filter, washing with THF. Cool filtrate back to 0° C. then add sodium borohydride (0.76 g, 3 equiv.) in one sum followed by the dropwise addition of methanol (4.1 mL, 15 equiv.). After 45 minutes at 0° C. remove cooling bath and let warm to room temperature for 15 minutes. Quench reaction (cautiously) with 1 N HCl (aq), approximately 50 mL. Extract with DCM. Wash organics with aqueous saturated sodium chloride. Dry organics over $MgSO_4$ then filter and concentrate. Purify on silica gel (2:1 Hexanes:Ethyl Acetate→1:1 Hexanes:Ethyl Acetate) to give a white solid (1.11 g, 58%). LCMS (ES), m/z 229 (M+1, product→t Butyl).

D. [4-Dimethylaminomethyl-5-(1-methyl-cyclopropyl)-thiazol-2-yl]-carbamic acid tert-butyl ester Dissolve [4-hydroxymethyl-5-(1-methyl-cyclopropyl)-thiazol-2-yl]-carbamic acid tert-butyl ester (1.11 g, 3.9 mmol) in DCM (50 mL) under nitrogen. Add triphenylphosphine (2.05 g, 2 equiv.) followed by carbon tetrabromide (2.6 g, 2 equiv.). Let stir at room temperature for 15 minutes then concentrate and purify on silica gel (Hexanes→9:1 Hexanes: Ethyl acetate) to give the bromide (1.02 g, 75%). Redissolve this material in THF (40 mL) and add dimethylamine (7.3 mL of a 2 M solution in THF, 5 equiv.) and stir at room temperature for 4 hours. Filter the reaction, washing with THF. Concentrate filtrate to give product (0.9 g, 99%). $^1$H NMR (400 MHz, DMSO-d$_6$) δ 11.2 (bs, 1H), 3.34 (s, 2H), 2.15 (s, 6H), 1.43 (s, 9H), 1.28 (s, 3H), 0.80 (m, 2H), 0.73 (m, 2H).

E. 4-Dimethylaminomethyl-5-(1-methyl-cyclopropyl)-thiazol-2-ylamine dihydrochloride Dissolve [4-dimethylaminomethyl-5-(1-methyl-cyclopropyl)-thiazol-2-yl]-carbamic acid tert-butyl (0.9 g, 2.9 mmol) in dioxane (40 mL) under nitrogen then add 4M HCl in dioxane (7.2 mL, 10 equiv.) and stir at room temperature overnight. LCMS shows mostly starting material. Heat the reaction at 40° C. overnight. LCMS shows partial conversion to product. Raise temperature to 60° C. and heat overnight. LCMS shows reaction complete. A white precipitate is present; filter to isolate solid. Solid appears hygroscopic. Redissolve solid in methanol and concentrate to give a white solid (0.784 g, 95%). MS (ES), m/z 212 (M+1).

Preparation 109

5-tert-Butyl-4-dimethylaminomethyl-thiazol-2-ylamine

Prepare using procedures similar to Preparation 108. Isolate the product using a SCX cartridge (10 g VARIAN bond elut), eluting with 1:1 methanol:dichloromethane, then 1:1 2 M NH$_3$ in methanol:dichloromethane. Concentrate the latter to afford the title compound (0.190 g, 1>100%). MS (ES), m/z 169 (M+1, product—NMe$_2$).

Prepare the following according to procedures similar to Preparations 108/109:

| Preparation | Compound Name | Physical Data MS (ES), m/z (M + 1) |
|---|---|---|
| 109b | 5-tert-Butyl-4-morpholin-4-ylmethyl-thiazol-2-ylamine | 256 |

Preparation 110

2-(2-Amino-thiazol-5-yl)-propan-2-ol

Add n-Butyl lithium (1.6 M solution in hexane, 24 mL, 38 mmol, 2.0 eq.) in a dropwise manner at −78° C. under nitrogen to the solution of 2-amino thiazole (1.90 g, 18.97 mmol, 1.0 eq.) in anhydrous THF (80 mL). Add chlorotrimethyl silane (4.8 mL, 38 mmol, 2.0 eq.) to the mixture slowly at −78° C. Let the reaction mixture warm up to 0° C. slowly and stir the mixture at 0° C. for 10 minutes. Cool the solution to −78° C. and add n-Butyl lithium (1.6 M solution in hexane, 12 mL, 19 mmol, 1.0 eq.) in a dropwise manner. Add acetone (1.4 mL, 19 mmol, 1.0 eq.) last. Stir the reaction mixture at −78° C. for 10 minutes, then at room temperature for 30 minutes. Quench with ammonium chloride (sat. 10 mL) at −78° C. Then warm up to room temperature. Add ethyl acetate (200 mL). Wash the organic layer with aqueous saturated sodium chloride (3×30 mL), water (2×30 mL). Dry the organic phase over MgSO$_4$ and filter the drying reagent off. Concentrate in vacuo. Purify by column chromatography (0%→5% methanol in dichloromethane→10% methanol in dichloromethane) to afford product (1.38 g, 46%). MS(ES), m/z 159 (M+1).

Prepare the following according to procedures similar to Preparation 110:

| Preparation | Compound Name | Physical Data MS (ES), m/z (M + 1) |
|---|---|---|
| 111 | 4-(2-Amino-thiazol-5-yl)-tetrahydro-pyran-4-ol | 242 |
| 112 | 1-(2-Amino-thiazol-5-yl)-cyclobutanol | 171 |

Preparation 113

5-Cyclobutyl-thiazol-2-ylamine

Hydrogenate 1-(2-amino-thiazol-5-yl)-cyclobutanol (0.94 g, 5.52 mmol, 1.0 eq.) in trifluoroacetic acid (16 mL) in the presence of Pearlman's catalyst (0.16 g) under H$_2$ (52 psi) for over night. Filter off the catalyst. Wash with methanol. Concentrate in vacuo. Add dichloromethane (100 mL) to the residue. Wash the organic layer with sodium bicarbonate (sat. 2×30 mL), aqueous saturated sodium chloride (2×20 mL) and water (2×30 mL). Dry the organic phase over MgSO$_4$ and filter the drying reagent off. Concentrate in vacuo. Purify by column chromatography (0%→5% methanol in dichloromethane) to afford product (0.508 g, 60%). MS(ES), m/z 155 (M+1).

Preparation 114

5-Isopropyl-4-pyrrolidin-1-ylmethyl-thiazol-2-ylamine

A. 4-Methyl-1-pyrrolidin-1-yl-pentane-1,2-dione

Add oxalychloride (5.3 mL, 60.24 mmol, 1.6 eq.) slowly to the solution of 4-methyl-2-oxovaleric acid (4.90 g, 37.65 mmol, 1.0 eq.) in dichloromethane (50 mL) at 0° C. under nitrogen. Add Dimethylforamide (2 drops) last. Stir the reaction mixture overnight. Concentrate in vacuo. Add dichloromethane (100 mL). Add this solution to the solution of pyrrolidine (6.90 g, 97.02 mmol, 2.6 eq.) in dichloromethane (50 mL) at 0° C. slowly under nitrogen. Stir the reaction mixture for 1 hour at room temperature after addition. Wash with HCl (1 N) until the aqueous layer is acidic, then with aqueous saturated sodium chloride (2×20 mL) and water (2×30 mL). Dry the organic phase over MgSO$_4$ and filter the drying reagent off. Concentrate in vacuo. Purify by column chromatography (0%→5% ethyl acetae in dichloromethane) to afford product (4.60 g, 66%).

B. 3-Bromo-4-methyl-1-pyrrolidin-1-yl-pentane-1,2-dione

Add 4-methyl-1-pyrrolidin-1-yl-pentane-1,2-dione (4.50 g, 24.56 mmol, 1.0 eq.) in chloroform (120 mL) to the solution of copper (II) bromide (16.45 g, 73.67 mmol, 3.0 eq.) in ethyl acetate (200 mL) at 68° C. Stir the reaction mixture overnight. Filter through a pad of celica, wash with dichloromethane. Concentrate in vacuo. Use the 6.12 g brown oil (23.3 mmol, 95%) for the next step without further purification.

C. (2-Amino-5-isopropyl-thiazol-4-yl)-pyrrolidin-1-yl-methanone

Add 3-bromo-4-methyl-1-pyrrolidin-1-yl-pentane-1,2-dione (3.0 g, 11.44 mmol, 1.0 eq.) to the solution of thiourea (1.31 mmol, 1.5 eq.) in ethanol (40 mL). Stir the reaction mixture at reflux for overnight. Concentrate in vacuo. Add dichloromethane (200 mL). Wash the organic layer with sodium bicarbonate (sat. 2×30 mL), aqueous saturated sodium chloride (2×20 mL) and water (2×30 mL). Dry the organic phase over MgSO$_4$ and filter the drying reagent off. Concentrate in vacuo. Purify by column chromatography (0%→5% ethyl acetae in dichloromethane) to afford product (4.60 g, 66%). MS(ES), m/z 240 (M+1).

D. 5-Isopropyl-4-pyrrolidin-1-ylmethyl-thiazol-2-ylamine

Prepare according to procedures similar to preparation of 3-morpholin-4-ylmethyl-5-trifluoromethyl-phenylamine. MS(ES), m/z 226 (M+1).

Preparation 115

5-tert-Butyl-4-(2-dimethylamino-ethoxy)-2-methyl-phenylamine

Heat a mixture of 4-amino-2-tert-butyl-5-methyl-phenol (600 mg, 3.2 mmol), N,N-dimethylamine ethyl bromide HBr salt (820 mg, 3.4 mmol), and potassium hydroxide (750 mg, 13.4 mmol) in 1,2-dimethoxyethane in a microwave vessel with irradiation of <10 Watts at a temperature of 150-170° C. for 5 minutes. After the reaction cools, filter via Celite® and wash with dichloromethane. Concentrate the filtrate and purify by silica gel column chromatography, with a gradient from 100% DCM to 5% MeOH in DCM to 5% (2N ammonia in MeOH) in DCM to yield the title compound as a red brown oil (26% yield). LCMS (ES), m/z 251 (M+1).

Preparation 116

3-tert-Butyl-5-morpholin-4-ylmethyl-phenylamine

A. 4-(3-tert-Butyl-5-iodo-benzyl)-morpholine

Dissolve 1-tert-butyl-3-iodo-5-methyl-benzene (1 g, 3.6 mmol, prepared according to *Chem. Soc. Perkin Trans. I*, 1987, page 859-866) in carbon tetrachloride (20 mL) under nitrogen. Add NBS (0.71 g, 1.1 equiv.) followed by AIBN (0.06 g, 0.1 equiv.) and heat overnight at 70° C. Filter in the morning, washing with hexanes. Concentrate filtrate and use crude. Dissolve this residue in THF (10 mL) under nitrogen and cool to 0° C. Add morpholine (0.64 mL, 2 equiv.) dropwise via syringe and stir 5 minutes with cooling. Remove ice bath and let warm to room temperature. After one hour concentrate to dryness and purify the residue on silica gel (Hexanes→4:1 Hexanes Ethyl Acetate) to give product (0.785 g, 60% over 2 steps). MS (ES), m/z 360.1 (M+1).

B 3-tert-Butyl-5-morpholin-4-ylmethyl-phenylamine

Combine 4-(3-tert-butyl-5-iodo-benzyl)-morpholine (0.785 g, 2.2 mmol), benzophenone imine (0.44 mL, 1.2 equiv.), sodium tert-butoxide (0.29 g, 1.4 equiv.), racemic BINAP (0.061 g, 4.5 mol %), and THF (10 mL). De-gas with nitrogen then add bis(dibenzylideneacetone) palladium (0.037 g, 3 mol %) and heat reaction at 50° C. overnight under nitrogen. In the morning add approximately 4 mL of 5 N HCl (aq) and heat for one hour at 50° C. Let cool to room temperature then dilute with ethyl acetate and make basic with 1 N NaOH (aq). Wash organics with water then aqueous saturated sodium chloride. Dry organics with MgSO$_4$, filter and concentrate in vacuo. Purify on silica gel (4:1 Hexanes:Ethyl Acetate→10% Methanol: DCM) to give product (0.449 g, 83%). MS (ES), m/z 249.3 (M+1).

Prepare the following according to procedures similar to Preparation 116:

| Preparation | Compound Name | Physical Data MS (ES), m/z (M + 1) |
|---|---|---|
| 117 | 3-tert-Butyl-5-dimethylaminomethyl-phenylamine | 207 |

Preparation 118

1-(3-Amino-phenyl)-2,2-dimethyl-propan-1-one

A. 1-(3-Iodo-phenyl)-2,2-dimethyl-propan-1-one

Combine NaOtBu (3.6 g, 4 equiv.), THF (10 mL), and NMP (10 mL) in a round bottomed flask. Place under nitrogen and cool to 0° C. Dissolve 1-(3-iodo-phenyl)-propan-1-one (2 g, 9.4 mmol) in THF (10 mL) and add dropwise to the reaction. Immediately following, add methyl iodide (2.3 mL, 4 equiv.) via syringe. Stir at 0° C. for 5 hours. Quench reaction with water then dilute with ethyl acetate. Wash organics with water then aqueous saturated sodium chloride. Dry over magnesium sulfate, filter and concentrate in vacuo. Purify by silica chromatography (Hex→5% EtOAc:Hexanes) to give 2.0 g clear liquid. $^1$H NMR (400 MHz, DMSO-d$_6$) δ 7.70 (m, 2H), 7.66 (m, 1H), 7.40 (m, 1H), 1.23 (s, 9H).

B. 1-(3-Amino-phenyl)-2,2-dimethyl-propan-1-one

Combine 1-(3-iodo-phenyl)-2,2-dimethyl-propan-1-one (2.0 g, 8.3 mmol), benzophenone imine (1.7 mL, 1.2 equiv.), racemic BINAP (0.23 g, 4.5 mol %), NaOtBu (1.1 g, 1.4 equiv.), and THF (30 mL). De-gas thoroughly with nitrogen then add bis(dibenzylideneacetone) palladium (0.14 g, 3 mol %) and place under nitrogen. Heat the reaction at 50° C. overnight. The next morning add approximately 8 mL 5 N HCl (aq) and heat for an additional hour at 50° C. Let cool to room temperature then dilute with ethyl acetate and make basic with 1 N NaOH (aq). Wash organics with aqueous saturated sodium chloride. Dry over magnesium sulfate, filter and concentrate in vacuo. Purify by silica chromatography (Hex→9:1 Hex:EtOAc→4:1 Hex:EtOAc) to give a yellow residue (1.2 g, 82%). MS (ES), m/z 178 (M+1).

Preparation 119

3-(6-Amino-4-tert-butyl-pyridin-3-yl)-N,N-dimethyl-acrylamide

A. 5-Bromo-4-tert-butyl-pyridin-2-ylamine

Dissolve 4-tert-butyl-pyridin-2-ylamine (3 g, 20 mmol) in anhydrous acetonitrile (25 mL). Add N-bromosuccinimide (3.56 g, 20 mmol). Stir the reaction in the dark for overnight at room temperature. Dilute with EtOAc and wash with 1 N NaOH (aq.) and saturated aqueous sodium bicarbonate. Extract the organic layer. Wash the aqueous layer further with DCM. Dry the combined organic layers (MgSO$_4$), and purify by silica gel column chromatography (EtOAc/hexane) to yield 2 g of the title compound (44%). LCMS (ES), m/z 231 (M+1).

B. 3-(6-Amino-4-tert-butyl-pyridin-3-yl)-N,N-dimethyl-acrylamide

De-gas a mixture of 5-bromo-4-tert-butyl-pyridin-2-ylamine (330 mg, 1.4 mol), N,N-dimethylacrylamide (0.22 mL, 2.1 mmol), triethylamine (0.4 mL, 2.1 mmol) in toluene (4 mL) while purging with nitrogen for 3 minutes. Add palladium(II)acetate (60 mg, 0.28 mmol) and tetrakis(triphenylphosphine)palladium(0) (690 mg, 0.6 mmol) under nitrogen. Heat the reaction overnight in sealed vessel at 120° C. Cool the mixture to room temperature, filter through Celite® and concentrate. Purification by silica gel column chromatography (100% DCM to 3% MeOH in DCM) to yield the title compound (81% yield). LCMS (ES), m/z 248 (M+1).

Prepare the following according to procedures similar to Preparation 119:

| Preparation | Name | Physical Data MS (ES), m/z |
|---|---|---|
| 120 | 3-(6-Amino-2-methyl-4-trifluoromethyl-pyridin-3-yl)-N,N-dimethyl-acrylamide | 274 |

Preparation 121

2-(4-Bromo-2-fluoro-phenyl)-N-[3-(morpholine-4-carbonyl)-5-trifluoromethyl-phenyl]-acetamide

A. Morpholin-4-yl-(3-nitro-5-trifluoromethyl-phenyl)-methanone

Dissolve 3-nitro-5-trifluoromethyl-benzoic acid (2.9 g, 12.6 mmol) and 1-hydroxy-7-azabenzotriazole (25 mL of 0.5 M solution in DMF) in THF. Add 1,3-dicyclohexylcarbodiimide (2.6 g, 12.6 mmol) and morpholine (1 g, 11 mmol). Stir the mixture for 48-72 hours at room temperature. Dilute the resulting suspension with DCM and quench with saturated aqueous ammonium chloride. Wash the organic layer further by aqueous saturated sodium chloride and water, dry (MgSO₄) and concentrate to a yellow-white residue. Purify by silica gel column chromatography, with a gradient from 100% hexane to 50% hexane in ethyl acetate, yielding the title compound as 2.5 g white solid (75% yield). LCMS (ES), m/z 305 (M+1).

B. (3-Amino-5-trifluoromethyl-phenyl)-morpholin-4-yl-methanone

Dissolve the morpholin-4-yl-(3-nitro-5-trifluoromethyl-phenyl)-methanone (830 mg, 2.7 mmol) in MeOH (40 mL) at room temperature. Add ammonium chloride (3 g, 56 mmol) and stir at for 10 minutes before adding Zn powder (5 g, 76 mmol) with stirring for another 5-10 minutes. Filter and wash with MeOH. Concentrate to a white solid of 2 g material, containing excess ammonium chloride. LCMS (ES), m/z 275 (M+1). Use in the next step without further purification.

C. 2-(4-Bromo-2-fluoro-phenyl)-N-[3-(morpholine-4-carbonyl)-5-trifluoromethyl-phenyl]-acetamide Dissolve (4-bromo-2-fluoro-phenyl)-acetic acid (692 mg, 3.0 mmol) in THF (24 mL) and add 1-(3-dimethylaminopropyl)-3-ethylcarbodiimide hydrochloride (618 mg, 3.2 mmol), stir for 10 minutes. Dissolve (3-amino-5-trifluoromethyl-phenyl)-morpholin-4-yl-methanone (740 mg, excluding excess ammonium chloride) from previous step in DCM (24 mL) with Et₃N (3.3 mL, 23 mmol). Add the activated acid to the amine mixture and stir at room temperature for overnight. Dilute the resulting suspension with EtOAc and wash with saturated NaHCO₃ and aqueous saturated sodium chloride successively. Dry the organic layer (MgSO₄), concentrate and purify by silica gel column chromatography (EtOAc/Hexane gradient) to obtain the title compound (15% yield). LCMS (ES), m/z 491 (M+1).

Prepare the following according to procedures similar to Preparation 121:

| Preparation | Name | Physical Data MS (ES), m/z (M + 1) |
|---|---|---|
| 122 | 3-[2-(4-Bromo-2-fluoro-phenyl)-acetylamino]-N-(tetrahydro-pyran-4-yl)-5-trifluoromethyl-benzamide | 505 |

Preparation 123

3-Morpholin-4-ylmethyl-5-trifluoromethyl-phenylamine

Dissolve (3-amino-5-trifluoromethyl-phenyl)-morpholin-4-yl-methanone (1.2 g, 4.3 mmol) in THF and dropwise and add BH₃-Me₂S solution (6.5 mL, 13.1 mmol, 2M in THF). Stir at room temperature for 3 hours. Add another portion of BH₃-Me₂S solution (2.2 mL, 4.3 mmol, 2M in THF) and heat at 65° C. for 1.5 hours under nitrogen. Cool to room temperature and quench carefully with dropwise addition of 1 N HCl:water 1:1 (8 mL), stir for 30-60 minutes. Extract by EtOAc and wash with saturated aqueous NaHCO₃ and aqueous saturated sodium chloride. Purification by silica gel column chromatography with gradient from 100% DCM to 6% MeOH in DCM to 5% (2N NH3 in MeOH)/in DCM, yielding the title compound (600 mg, 54% yield). LCMS (ES), m/z 261 (M+1).

Preparation 124

4-Dimethylaminomethyl-pyridin-2-yl amine

A. 2-Amino-N,N-dimethyl-isonicotinamide

To LDA (7.3 mL, 13 mmol, 1.8M in ether/heptane) at 0° C., add dropwise dimethylamine (13 mL, 26 mmol, 2M in THF) under nitrogen. Stir for 30 minutes and add 2-amino-4-pyridine carboxylic acid methyl ester (2 g, 13 mmol, in 3 mL of anhydrous THF and 2 mL of anhydrous ether). Seal and heat at 85° C. overnight. Cool the mixture to room temperature and quench with water. Dilute with EtOAc and isolate the top organic layer. Extract the aqueous layer further with saturated sodium bicarbonate and ether, then DCM. Pool all the organic layers, dry (MgSO₄) and concentrate. Purify by strong cation exchange (SCX) column to obtain the crude product and use in the next step without further purification. LCMS (ES), m/z 166 (M+1).

B. 4-Dimethylaminomethyl-pyridin-2-ylamine

Use the same procedure that was described for the preparation of 3-morpholin-4-ylmethyl-5-trifluoromethyl-phenylamine to obtain the desired compound. Use in the next step without chromatography purification.

Preparation 125

4-Cyclopropyl-pyridin-2-ylamine

A. 4-Cyclopropyl-pyridine

In a 3-neck round bottom flask of anhydrous THF (60 mL), add pyridine (6.1 mL, 75 mmol) and cool to −20° C. Add CuI (463 mg, 2.5 mmol), and then dropwise add ethyl chloroformate (4.8 mL, 50 mmol) via a syringe and stir. At the same temperature, add cyclopropylmagnesium bromide solution (100 mL, 0.5 M in ether, 50 mmol) dropwise via a syringe over 10-15 minutes. Stir for 15 minutes at −20° C., and then at room temperature for 2 hours. Dilute the reaction with ether (200 mL) and quench at room temperature by $NH_4Cl$ (20% aq.). Wash the organic layer by 30-50 mL portions of 20% $NH_4Cl/NH_4OH$ (1:1) buffer, water, 10% HCl, water and aqueous saturated sodium chloride subsequently. Dry the organic layer over $MgSO_4$ and concentrate to a crude orange-brown/yellow oil. Purification by silica gel/column chromatography with a gradient of hexane to 50% hexane/ether to afford the dihydropyridine intermediate.

Heat the crude dihydropyridine intermediate (3.3 g, approximately 17 mmol) with sulfur (neat, 656 mg, 20 mmol) at 190-200° C. for 100 minutes while distillation of ethanol proceeds. After removal of ethanol is completed, vacuum distill the remaining residue to afford the title compound in 30% yield (2 steps). LCMS (ES), m/z 120 (M+1).

B. 4-Cyclopropyl-pyridin-2-ylamine

Reflux 4-cyclopropyl-pyridine (600 mg, 5 mmol), N,N-dimethylaniline (1.4 mL, 11 mmol) and $NaNH_2$ (50% in toluene, 468 mg, 6 mmol) at 150-160° C. under nitrogen in toluene for overnight. Cool the mixture and dilute with water and ethyl acetate. Extract the organic layer by minimal amount of water. Dry the organic layer (combination of anhydrous $MgSO_4$, $Na_2SO_4$ and $K_2CO_3$), concentrate and purify by silica gel column chromatography to obtain the title compound in 12% yield. LCMS (ES), m/z 135 (M+1).

Prepare the following according to procedures similar to Preparation 125:

| Preparation | Name | Physical Data MS (ES), m/z (M + 1) |
|---|---|---|
| 126 | 4-Isobutyl-pyridin-2-ylamine | 151 |
| 127 | 4-sec-Butyl-pyridin-2-ylamine | 151 |

Preparation 128

2-(4-Bromo-2-fluoro-phenyl)-N-[5-(1-methyl-cyclopropyl)-[1,3,4]thiadiazol-2-yl]-acetamide Combine (4-bromo-2-fluoro-phenyl)-acetic acid (3.81 g, 16.35 mmol) and 5-(1-Methyl-cyclopropyl)-[1,3,4]thiadiazol-2-ylamine (2.54 g, 16.35 mmol) in THF (45 mL). Under $N_2$, add 4-methyl-morpholine (2.16 mL, 19.62 mmol), then 4-(4,6-dimethoxy-[1,3,5]triazin-2-yl)-4-methyl-morpholin-4-ium; chloride (5.43 g, 19.62 mmol). Stir the reaction mixture for 14 hours under $N_2$. Extract with ethyl acetate versus water. Wash with aqueous saturated sodium chloride, dry over magnesium sulfate, filter, and concentrate. Triturate the resulting solid from ethyl acetate/hexanes, filter, and dry to give fluffy white solid as the title compound (2.86 g, 47%). MS (ES), mm/z 370, 372 (M+1).

Preparation 129

4-(3-Amino-5-trifluoromethyl-benzoyl)-piperazine-1-carboxylic acid tert-butyl ester

A. 4-(3-Nitro-5-trifluoromethyl-benzoyl)-piperazine-1-carboxylic acid tert-butyl ester Prepare the title compound according to the same procedure as Preparation 128. MS (ES), m/z 402 (M−1).

B. 4-(3-Amino-5-trifluoromethyl-benzoyl)-piperazine-1-carboxylic acid tert-butyl ester Hydrogentate 4-(3-nitro-5-trifluoromethyl-benzoyl)-piperazine-1-carboxylic acid tert-butyl ester (4.8 g, 11.9 mmol) in MeOH (120 mL) with 10% Pd on activated carbon (400 mg) at room temperature for 3 hours. Filter and concentrate into a white solid as the title compound (3.94 g, 10.55 mmol, 89%). MS (ES), m/z 372 (M−1). Use in the next step without purification.

Prepare the following according to procedures similar to Preparation 128:

| Preparation | Name | Physical Data MS (ES), m/z |
|---|---|---|
| 130 | 2-(4-Bromo-2-fluoro-phenyl)-N-(5-tert-butyl-thiazol-2-yl)-acetamide | 373 (M + 2, Br pattern) |
| 131 | 2-(4-Bromo-2-fluoro-phenyl)-N-(5-isopropyl-thiazol-2-yl)-acetamide | 359 (M + 2, Br pattern) |
| 132 | 2-(4-Bromo-2-fluoro-phenyl)-N-(5-isopropyl-4-methyl-thiazol-2-yl)-acetamide | 373 (M + 2, Br pattern) |
| 133 | N-(3-Acetyl-phenyl)-2-(4-bromo-2-fluoro-phenyl)-acetamide | 352 (M + 2, Br pattern) |
| 134 | 2-(4-Bromo-2-fluoro-phenyl)-N-(3-tert-butyl-5-morpholin-4-ylmethyl-phenyl)-acetamide | 465.2, 463.3 (M + 1, bromide pattern) |
| 135 | 2-(4-Bromo-2-fluoro-phenyl)-N-[4-dimethylaminomethyl-5-(1-methyl-cyclopropyl)-thiazol-2-yl]-acetamide | 426 (M + 1) |

-continued

| Preparation | Name | Physical Data MS (ES), m/z |
|---|---|---|
| 136 | 2-(4-Bromo-2-fluoro-phenyl)-N-(4-tert-butyl-pyridin-2-yl)-acetamide | 365.13, 367.12 Br isotopes (M), (M + 2) |
| 137 | 2-(4-Bromo-2-fluoro-phenyl)-N-(4-trifluoromethyl-pyridin-2-yl)-acetamide | 377, 379 (M + 1) |
| 138 | 2-(4-Bromo-2-fluoro-phenyl)-N-(5-tert-butyl-[1,3,4]thiadiazol-2-yl)-acetamide | 372, 374 (M + 1) |
| 139 | 2-(4-Bromo-2-fluoro-phenyl)-N-[5-tert-butyl-4-(2-dimethylamino-ethoxy)-2-methyl-phenyl]-acetamide | 466 (M + 1) |
| 140 | 2-(4-Bromo-2-fluoro-phenyl)-N-(3-morpholin-4-ylmethyl-5-trifluoromethyl-phenyl)-acetamide | 476 (M + 1) |
| 141 | 2-(4-Bromo-2-fluoro-phenyl)-N-(4-dimethylaminomethyl-pyridin-2-yl)-acetamide | 367 (M + 1) |
| 142 | 2-(4-Bromo-2-fluoro-phenyl)-N-(3-tert-butyl-phenyl)-acetamide | 365 (M + 1) |
| 143 | 2-(4-Bromo-2-fluoro-phenyl)-N-(4-cyclopropyl-pyridin-2-yl)-acetamide | 350 (M + 1) |
| 144 | 3-{6-[2-(4-Bromo-2-fluoro-phenyl)-acetylamino]-4-tert-butyl-pyridin-3-yl}-N,N-dimethyl-acrylamide | 463 (M + 1) |
| 145 | 3-{6-[2-(4-Bromo-2-fluoro-phenyl)-acetylamino]-2-methyl-4-trifluoromethyl-pyridin-3-yl}-N,N-dimethyl-acrylamide | 489 (M + 1) |
| 146 | 2-(4-Bromo-2-fluoro-phenyl)-N-(5-cyclobutyl-thiazol-2-yl)-acetamide | 371 (M + 1) |
| 147 | 2-(4-Bromo-2-fluoro-phenyl)-N-[5-(1-hydroxy-1-methyl-ethyl)-thiazol-2-yl]-acetamide | 375 (M + 1) |
| 148 | 2-(4-Bromo-2-fluoro-phenyl)-N-[5-(1-hydroxy-tetrahydro-pyran-4-yl)-thiazol-2-yl]-acetamide | 415, 417 (M + 1) |
| 149 | 2-(4-Bromo-2-fluoro-phenyl)-N-(4-isobutyl-pyridin-2-yl)-acetamide | 365, 367 (M + 1) |
| 150 | 2-(4-Bromo-2-fluoro-phenyl)-N-(4-sec-butyl-pyridin-2-yl)-acetamide | 365, 367 (M + 1) |
| 151 | 2-(4-Bromo-2-fluoro-phenyl)-N-(5-isopropyl-4-pyrrolidin-1-ylmethyl-thiazol-2-yl)-acetamide | 440, 442 (M + 1) |
| 152 | 4-[3-(4-Bromo-2-fluoro-benzoylamino)-5-trifluoromethyl-benzoyl]-piperazine-1-carboxylic acid tert-butyl ester | 372 (M + 1) |

Preparation 153

4-[7-(2-Diethylaminomethyl-pyridin-4-yl)-imidazo[1,2-a]pyridin-3-yl]-2-fluoro-phenylamine Combine diethyl-(4-imidazo[1,2-a]pyridin-7-yl-pyridin-2-ylmethyl)-amine (1.00 g, 3.57 mmol), 4-bromo-2-fluoro-phenylamine (1.36 g, 7.13 mmol) and potassium acetate (0.700 g, 7.13 mmol) in DMSO (4 mL). De-gas the mixture for 10 minutes with $N_2$. Add dichlorobis(triphenylphosphine) palladium (II) (0.250 g, 0.357 mmol); stir the reaction mixture for 14 hours under $N_2$ at 100° C. Purify using an SCX cartridge (10 g VARIAN bond elut), eluting with 1:1 methanol:dichloromethane, then 1:1 2 M $NH_3$ in methanol:dichloromethane. Purify via reverse phase chromatography using a 25 cm by 50.8 mm (i.d.) column w/10 micron particles (MeCN/0.03% HCl $H_2O$ (5:95) to 100% MeCN; 30 min). Compound obtained is partitioned between ethyl acetate and 1 N NaOH. Wash the organic layer with aqueous saturated sodium chloride, dry over magnesium sulfate, filter, and concentrate to afford the title compound (0.286 g, 21%). MS(ES), m/z 390 (M+1).

Preparation 154

4-[4-(3-{4-[3-(5-tert-Butyl-isoxazol-3-yl)-ureido]-3-fluoro-phenyl}-imidazo[1,2-a]pyridin-7-yl)-benzoyl]-piperazine-1-carboxylic acid tert-butyl ester Combine 4-(3-{4-[3-(5-tert-Butyl-isoxazol-3-yl)-ureido]-3-fluoro-phenyl}-imidazo[1,2-a]pyridin-7-yl)-benzoic acid (2.00 g, 3.89 mmol), piperazine-1-carboxylic acid tert-butyl ester (1.09 g, 5.84 mmol), 1-(3-dimethylaminopropyl)-3-ethylcarbodiimide hydrochloride (0.821 g, 4.28 mmol), triethylamine (1.63 mL, 11.68 mmol), and 1-hydroxybenzotriazole (0.579 g, 4.28 mmol) in DMF (50 mL). Stir at room temperature for 14 hours. Partition between ethyl acetate and 1 N NaOH, wash with aqueous saturated sodium chloride, dry over magnesium sulfate, filter, and concentrate. Triturate the resulting solid from $CH_2Cl_2$/hexanes, filter, and dry to give off-white solid as product (1.53 g, 58%). MS (ES), m/z 683 (M+1).

Prepare the following according to procedures similar to the one above:

| Preparation | Name | Characterization |
|---|---|---|
| 155 | {4-[3-(4-Amino-3-fluoro-phenyl)-imidazo[1,2-a]pyridin-7-yl]-phenyl}-(4-methyl-piperazin-1-yl)-methanone | 430 (M + 1) |
| 156 | N,N-Bis-(2-hydroxy-ethyl)-4-(3-iodo-imidazo[1,2-a]pyridin-7-yl)-benzamide | 452 (M + 1) |

Preparation 157

(4-{7-[4-(4-Methyl-piperazine-1-carbonyl)-phenyl]-imidazo[1,2-a]pyridin-3-yl}-benzyl)-carbamic acid tert-butyl ester Combine [4-(7-boronic acid-imidazo[1,2-a]pyridin-3-yl)-benzyl]-carbamic acid tert-butyl ester (1.86 g, 5.07 mmol), (4-bromo-phenyl)-(4-methyl-piperazin-1-yl)-methanone (1.6 g, 5.65 mmol), sodium carbonate (1.08 g, 10.14 mmol) in 1,4-dioxane (50 mL) and water (5 mL). Bubble nitrogen through the mixture for five minutes. Add tetrakis-(triphenylphosphine-palladium[0] (0.29 g, 0.25 mmol). Attach a reflux condenser, and heat the mixture to 80° C., stir overnight (15 hours), and cool to room temperature. Add ethylacetate/water (300 mL/100 mL). Extract the aqueous phase 2× with ethylacetate (100 mL). Extract the combined organic phase with aqueous saturated sodium chloride (50 mL) and then dry the organic phase over anhydrous magnesium sulfate. Filter the organic phase and concentrate the filtrate to a residue. Purify by chromatography (hexanes→50% ethyl acetate/hexanes→5% methanol in dichloromethane→10% methanol in dichloromethane→10% 2N ammonia methanol in dichloromethane) to afford the title product (0.87 g, 33%). MS(ES), m/z 526 (M+1).

Preparation 158

{4-[3-(4-Aminomethyl-phenyl)-imidazo[1,2-a]pyridin-7-yl]-pyridin-2-ylmethyl}-diethyl-amine tri-hydrochloride

A. 4-Iodo-2-methyl-pyridine

Dissolve 4-chloro-2-methyl-pyridine (1.2 g, 9.4 mmol) in THF (10 mL) under nitrogen. Add 4 M HCl in dioxane (2.4 mL, 1.0 equiv.) dropwise to the reaction to give a white precipitate. Stir five minutes then concentrate to dryness. Add sodium iodide (4.8 g, 3.4 equiv.) and acetonitrile (40 mL) to the solid and reflux overnight under nitrogen. Dilute with DCM then wash with a solution of $K_2CO_3$ and $NaHSO_3$ (approximately 10% and 5% respectively). Dry the organics over $MgSO_4$ then filter and concentrate. Purify by silica gel (Hexanes→9:1 Hexanes:Ethyl Acetate→4:1 Hexanes:Ethyl Acetate) to give a clear oil (1.1 g, 53%). MS (ES), m/z 220.0 (M+1).

B. Diethyl-(4-iodo-pyridin-2-ylmethyl)-amine

Combine 4-iodo-2-methyl-pyridine (1.1 g, 5 mmol), NBS (0.98 g, 1.1 equiv.) and carbon tetrachloride (50 mL) in a round bottomed flask under nitrogen. Add AIBN (82 mg, 0.1 equiv.) and heat reaction overnight at reflux. Filter the reaction, washing with hexanes. Concentrate filtrate to approximately 10-20 mL volume. Redissolve in THF (20 mL) and cool to 0° C. under nitrogen. Add diethylamine (1.04 mL, 2 equiv.) dropwise via syringe and stir one hour at 0° C. Remove cooling bath and let warm to room temperature. After 6 hours total, concentrate to dryness and purify by silica gel (1:1 Hexanes:Ethyl Acetate→Ethyl Acetate) to give a tan liquid (0.51 g, 35% over 2 steps). MS (ES), m/z 291.0 (M+1).

C. {4-[7-(2-Diethylaminomethyl-pyridin-4-yl)-imidazo[1,2-a]pyridin-3-yl]-benzyl}-carbamic acid tert-butyl ester Combine {4-[7-(boronic acid)-imidazo[1,2-a]pyridin-3-yl]-benzyl}-carbamic acid tert-butyl ester (0.46 g, 1.3 mmol), diethyl-(4-iodo-pyridin-2-ylmethyl)-amine (0.51 g, 1.4 equiv.), $Na_2CO_3$ (0.265 g in 1.25 mL $H_2O$), and DME (20 mL). De-gas with nitrogen then add tetrakis (triphenylphosphine) palladium (72 mg, 5 mol %) and heat overnight at 80° C. under nitrogen. Load directly onto a Varian MegaElut® SCX cartridge (10 gram cartridge prewashed with methanol), decanting from $Na_2CO_3$ as much as possible. Rinse with methanol to remove impurities then elute crude product with 2 M $NH_3$ in methanol. Concentrate this solution in vacuo then purify by silica gel chromatography (Ethyl Acetate→5% Methanol:DCM→10% Methanol:DCM) to give a yellow residue (0.246 g, 40%). MS (ES), m/z 486.2 (M+1).

D. {4-[3-(4-Aminomethyl-phenyl)-imidazo[1,2-a]pyridin-7-yl]-pyridin-2-ylmethyl}-diethyl-amine tri-hydrochloride Dissolve {4-[7-(2-diethylaminomethyl-pyridin-4-yl)-imidazo[1,2-a]pyridin-3-yl]-benzyl}-carbamic acid tert-butyl ester (0.24 g, 0.49 mmol) in dioxane (10 mL) under nitrogen. Add 4 M HCl in dioxane (5 mL) to the reaction and stir for 2 hours. Concentrate to dryness and use crude as the tri-HCl salt (0.321 g, crude). MS (ES), m/z 386.2 (M+1).

Prepare the following according to procedures similar to Preparation 158:

| Preparation | Compound Name | Physical Data MS (ES), m/z (M + 1) |
|---|---|---|
| 159 | {6-[3-(4-Aminomethyl-phenyl)-imidazo[1,2-a]pyridin-7-yl]-pyridin-3-ylmethyl}-diethyl-amine | 486 |
| 160 | 4-[7-(1-methyl-imidazol-2-yl)-imidazo[1,2-a]pyridin-3-yl]-benzylamine | 304 |
| 161 | 4-[7-(1H-Pyrazol-4-yl)-imidazo[1,2-a]pyridin-3-yl]-benzylamine | 290 |

Preparation 162

7-[6-(2-Morpholin-4-yl-propyl)-pyridin-2-yl]-imidazo[1,2-a]pyridine

A. 1-(6-Chloro-pyridin-2-yl)-propan-2-one

Charge into a well stirred $N_2$ flushed RBF 2-chloro-6-methylpyridine (15 g, 177 mmol), THF (120 mL), and cool to −78° C. in Dewar containing dry ice/acetone. Add slowly over 15 minutes. 1.6 M n-BuLi in hexane (80 mL, 128 mmol) via addition funnel. Mix reaction for 30 minutes at −78° C. then add dimethyl acetamide (15.3 g, 16.3 mL, 175 mmol) over 10 minutes. Quench by adding MeOH slowly. Concentrate by stripping off solvent under reduced pressure. Mix residue with (1:1) hexane:EtOAc and filter. Chromatograph filtrate in 2 portions on (120 g ISCO®) $SiO_2$ eluting with a gradient of 20% to 50% EtOAc with the balance hexane Strip off solvents under reduced pressure to give gold oil 6.97 g (35.2%) also 5.6 g of 2-chloro-6-methylpyridine can be recovered MS(ES), m/z 170 (M+1).

B. 1-(6-Imidazo[1,2-a]pyridin-7-yl-pyridin-2-yl)-propan-2-one

Prepare from 1-(6-chloro-pyridin-2-yl)-propan-2-one and 7-(4,4,5,5-Tetramethyl-[1,3,2]dioxaborolan-2-yl)-imidazo

[1,2-a]pyridine using conditions similar to Preparation 21 step A. MS(ES), m/z 170 (M+1).

C. 7-[6-(2-Morpholin-4-yl-propyl)-pyridin-2-yl]-imidazo[1,2-a]pyridine

In a well mixed round bottomed flask under $N_2$ charge 1-(6-Imidazo[1,2-a]pyridin-7-yl-pyridin-2-yl)-propan-2-one (1.8 g, 7.2 mmol), morpholine mono HCl salt (16 g, 129 mmol), 3 Å molecular sieves (powdered, vacuum oven dried 110° C. for 24 hours., 3.6 g), methanol (200 mL), and 1 M NaCNBH$_3$ solution in THF (12.9 mL, 12.9 mmol). Stir for 24 hours. at room temp. Filter through Celite® strip off solvents under reduced pressure. Take up into DCM and adjust pH to 10 with 5N NaOH and extract with DCM (5×). Concentrate DCM under reduced pressure and chromatograph on (120 g ISCO®) $SiO_2$ eluting with a slow gradient of 0% to 10% 2 M $NH_3$ in MeOH with the balance DCM. Strip off solvents under reduced pressure to give clear oil 1.67 g (72%) MS(ES), m/z 323 (M+1).

Preparation 163

7-[6-(2-Morpholin-4-yl-propyl)-pyridin-3-yl]-imidazo[1,2-a]pyridine

Prepare in a similar way as 7-[6-(2-morpholin-4-yl-propyl)-pyridin-2-yl]-imidazo[1,2-a]pyridine. In the first step LDA is used with starting material 5-bromo-2-methylpyridine. MS (ES) m/z 323 (M+1).

Preparation 164

4-Bromo-2-fluoro-phenylacetic acid, tert-butyl ester

Combine 4-bromo-2-fluoro-phenyl acetic acid (15 g, 0.064 mol), dichloromethane (30 mL) and concentrated sulfuric acid (1.1 mL) in a 2 L stainless steel Parr® vessel. Cool the vessel and contents in a dry ice-acetone bath. Freshly distill isobutene (60 mL) with dry ice-acetone condenser and add the isobutene to the cooled Parr® vessel. Seal and pressurize the vessel with nitrogen (20 psig), agitate while allowing the reaction to warm to room temperature and continue agitation at room temperature for 18 hours. Cool the vessel to 10-15° C. with dry ice, vent, and carefully add 150 mL of ice-cold saturated sodium carbonate solution and mix. Decant vessel contents, rinse vessel with dichloromethane (100 mL), agitate mixture and separate the phases. Extract aqueous phase twice with 100 mL portions of dichloromethane, combine organic layers and wash with aqueous saturated sodium chloride, dry over $MgSO_4$ and concentrate to produce 18.61 g (90%) of the title compound as a light orange oil. MS (ES) m/z 288/290, (M+1).

Preparation 165

4-tert-Butyl-6-morpholin-4-ylmethyl-pyridin-2-ylamine

A. (4-tert-Butyl-pyridin-2-yl)-morpholin-4-yl-methanone

Suspend 4-tert-butyl-pyridine-2-carboxylic acid hydrochloride (11.14 g, 51.8 mmol) in 50 mL dichloromethane, add 4-methylmorpholine (10.48 g, 11.4 mL, 104 mmol), stir, add 100 mL THF and stir the suspension a few minutes. Add N,N'-carbonyldiimidazole (8.4 g, 51.8 mmol) to the stirring suspension, note moderate gas evolution and stir the light suspension at room temperature for 30 to 90 minutes. Add morpholine (13.54 g, 13.61 mL, 155 mmol) via pipet, stir overnight at room temperature. Dilute the suspension with 400 mL dichloromethane, wash with 400 mL saturated aqueous sodium bicarbonate solution and back-extract the aqueous phase with 100 mL dichloromethane. Combine organic layers and wash with 300 mL portions of saturated sodium bicarbonate (once) and dilute aqueous saturated sodium chloride (three times). Dry the organic layers over $MgSO_4$ concentrate to an oil and purify on a 400 g silica cartridge with a gradient of 0→10% acetone in EtOAc over 20 minutes. Pool, concentrate, and dry fractions to provide 10.24 grams of a viscous colorless oil. LCMS (ES) m/z 249 (M+1).

B. (4-tert-Butyl-1-oxy-pyridin-2-yl)-morpholin-4-yl-methanone

Dissolve (4-tert-butyl-pyridin-2-yl)-morpholin-4-yl-methanone (10.24 g, 41.2 mmol) in dichloromethane (21 mL), add methyltrioxorhenium (VII) (MTO, 620 mg, 2.48 mmol, 0.06 eq) and stir to give a pale olive green solution. Jacket flask with room temperature water bath, add 8.5 mL aqueous hydrogen peroxide via pipet to produce a canary yellow emulsion that evolves gas. Stir the emulsion overnight at room temperature, then add a suspension of $MnO_2$ (25 mg) in 5 mL water to quench excess peroxide. Stir 45-60 minutes until gas evolution subsides, filter the mixture through filter paper, then remove volatiles by evaporation under vacuum to provide a viscous yellow oil. Purify oil on a 400 g silica cartridge with a gradient of 0→20% MeOH in acetone over 20 minutes. Pool, concentrate and dry appropriate fractions to provide 9.49 g (87%) of the title compound as a tacky foam. LCMS (ES) m/z 265 (M+1).

C. (6-Amino-4-tert-butyl-pyridin-2-yl)-morpholin-4-yl-methanone

Dissolve (4-tert-butyl-1-oxy-pyridin-2-yl)-morpholin-4-yl-methanone (9.8 g, 37 mmol) in anhydrous pyridine (29.33 g, 30 mL, 370 mmol) and add p-toluenesulfonyl chloride (10.58 g, 55.5 mmol, 1.5 eq), fit flask with reflux condenser and warm the clear brown-red solution to 45° C. overnight under nitrogen atmosphere. Remove volatiles in vacuo at 50° C. bath temperature to yield a viscous brown-red oil. Dissolve the oil in ethanolamine (55 mL) with thorough agitation to provide a deep brown-red solution. Cool the flask with water to keep the reaction at about room temperature and stir for 30-60 minutes. Dilute the mixture with 400 mL cool water and 50 mL 1 N NaOH, stir and a few chunks of ice. Stir the slurry and filter off the tan-yellow solid with a fritted funnel. Dissolve the filter cake in dichloromethane (150 mL), dry over $MgSO_4$, filter and concentrate to provide an orange-white solid. Purify this solid on a 400 g silica cartridge employing a gradient of 0→5% MeOH in dichloromethane over 30 minutes. Concentrate fractions and dry under high vacuum to give 6.02 g of an off white solid. Extract additional material from the filtrate (above) by extracting it three times with 200 mL portions of dichloromethane. Combine organic layers, dry over $MgSO_4$, concentrate to a brown-orange oil. Dissolve the oil in 15 mL dichloromethane and apply to a 400 g silica cartridge and elute the product with neat acetone. Concentrate and dry clean fractions to provide 2.0 g of product. Net recovery 8.02 g (82%) of the title compound. LCMS (ES) m/z 264 (M+1).

D. 4-tert-Butyl-6-morpholin-4-ylmethyl-pyridin-2-ylamine

Suspend (6-amino-4-tert-butyl-pyridin-2-yl)-morpholin-4-yl-methanone (6.02 g, 22.86 mmol) in 40 mL anhydrous THF. Add 2 M solution of $BH_3$-$Me_2S$ complex in THF (34.3 mL, 68.6 mmol, 3 eq) dropwise at room temperature. On $BH_3$-$Me_2S$/THF solution addition, the suspension turns clear and bright yellow after complete addition. Stir overnight at room temperature under nitrogen atmosphere. Carefully quench reaction with slow addition of MeOH (24 mL), stir 3 hours at 60° C. and concentrate in vacuo. Purify the residue on 300 g silica cartridge with a gradient of 0→2% MeOH in dichloromethane over 2 minutes, followed by 2→10% MeOH in dichloromethane over 40 minutes. Concentrate and dry clean fractions to give 2.0 g (35%) of the title compound as a white solid. LCMS (ES) m/z 250 (M+1).

Preparation 166

N-(4-Cyano-3-trifluoromethyl-phenyl)-2-[4-(4,4,5,5-tetramethyl-[1,3,2]dioxaborolan-2-yl)-phenyl]-acetamide

A. 2-(4-Bromo-phenyl)-N-(4-cyano-3-trifluoromethyl-phenyl)-acetamide

Dissolve 4-bromo-phenyl acetic acid (5 g, 23.3 mmol) in 125 mL dichloromethane. Add 1 mL DMF, stir to give a clear solution, then add oxalyl chloride (3.25 g, 2.23 mL, 25.5 mmol) portionwise via syringe and stir at room temperature for 15-30 minutes until gas evolution ceases. Remove volatiles on rotovap to yield a clear yellow oil. Dissolve the oil in 100 mL amylene-stabilized chloroform, chill on ice and fit flask with a dropping funnel. Fill the dropping funnel with a solution of 4-amino-2-trifluoromethyl-benzonitrile (4.65 g, 25 mmol) and pyridine (6.05 g, 6.19 mL, 76.5 mmol) in 200 mL amylene-stabilized chloroform. Add the benzonitrile solution to the cold acid chloride solution with stirring over 30 minutes, remove the ice bath and stir overnight at room temperature. Dilute the reaction mixture with 200 mL dichloromethane, wash twice with 250 mL portions of 1 N $NaHSO_4$, once with aqueous saturated sodium chloride, then dry over $MgSO_4$ and concentrate to a brown solid. Purify on Biotage 75L® silica cartridge in 4.5:4.5:1 $CH_2Cl_2$:hexanes:diethyl ether to yield 4.33 g (48%) of the title compound as a pale yellow-ivory solid. LCMS (ES) m/z 381,383 (M−1).

B. N-(4-Cyano-3-trifluoromethyl-phenyl)-2-[4-(4,4,5,5-tetramethyl-[1,3,2]dioxaborolan-2-yl)-phenyl]-acetamide Dissolve 2-(4-bromo-phenyl)-N-(4-cyano-3-trifluoromethyl-phenyl)-acetamide (4.23 g, 11 mmol) in 125 mL dioxane, add bis(pinacolato)diboron (3.5 g, 13.8 mmol), tricyclohexylphosphine (386 mg, 1.38 mmol), and anhydrous potassium acetate (1.62 g, 16.5 mmol). Bubble nitrogen through the mixture for at least 15 minutes to deoxygenate, then add palladium (II) acetate (123 mg, 0.55 mmol), fit flask with a reflux condenser and heat at 80° C. under nitrogen atmosphere for 4 hours. Cool reaction mixture and pass through a 50 g silica cartridge with 400 mL EtOAc. Concentrate the clear brown eluate to a tan-gray solid and recrystallize from dichloromethane-hexanes to give 3.7 g (78%) of the title compound as tan-gray crystals. LCMS (ES) m/z 429 (M−1).

Preparation 167

2-(4-Bromo-phenyl)-N-(6-methyl-4-trifluoromethyl-pyridin-2-yl)-acetamide

Dissolve 4-bromo-phenylacetic acid (660 mg, 3.07 mmol) and 6-methyl-4-trifluoromethyl-pyridin-2-ylamine (500 mg, 2.84 mmol) in 10 mL dry THF. Add 4-methyl morpholine (345 mg, 0.375 mL, 3.4 mmol), stir a few minutes under nitrogen atmosphere, then add DMTMM (865 mg, 3.12 mmol) and stir the pale yellow slurry overnight. Dilute slurry with 90 mL EtOAc, wash twice each with saturated aqueous $NaHCO_3$ and aqueous saturated sodium chloride, then dry the organic layer over $MgSO_4$ and concentrate to give an ivory crystalline solid. Purify this solid on a 120 g silica cartridge with 0→5% EtOAc in dichloromethane to give 660 mg (62%) of the title compound as a white crystalline solid. LCMS (ES) m/z 373/375 (M+1).

Preparation 168

4-tert-Butyl-6-methyl-pyridin-2-ylamine

A. 2-Methyl-4-tert-butyl-pyridine

Cool a solution of methyl lithium in ether (200 mL, 1.6 M, 320.00 mmol) in an ice bath and add 4-tert-butyl-pyridine (20.28 g, 150.00 mmol) drop wise. Once the substrate is added, warm the reaction to ambient temperature for 3 hours. Concentrate the reaction to near dryness to remove the ether and then add anhydrous toluene (200 mL) and heat to reflux for 20-21 hours. Cool in an ice bath while slowly and cautiously adding ice to quench the reaction. Add water (200 mL) and then extract the aqueous with ethyl acetate (3×250 mL) and separate the layers. Pool, desiccate, filter and concentrate the organic extracts to an oil. Chromatograph the oil on silica using a gradient of 0→50% ethyl acetate hexanes over 25 minutes to yield the title compound (16.60 g, 111.23 mmol). MS(ESI), m/z 150 (M+1).

B. 4-tert-Butyl-2-methyl-pyridine 1-oxide

Dissolve 2-methyl-4-tert-butyl-pyridine (16.60 g, 111.23 mmol) in dichloromethane (80 mL) and add methyltrioxorhenium (VII) (0.139 g, 0.56 mmol) with vigorous stirring. At ambient temperature, add 30% hydrogen peroxide (40 mL) and stir vigorously for 18 hours. Quench the reaction by adding drop wise aqueous manganese dioxide (100 mg in 20 mL). After the off-gassing ceases, the aqueous turns a cloudy gray, the layers are separated and the aqueous is re-extracted with dichloromethane (3×100 mL). The organics are pooled, desiccated, filtered and concentrated to yield the title compound analytically pure (16.60 g, 100.61 mmol). MS (ESI), m/z 166 (M+1).

C. 2-Chloro-6-methyl-4-tert-butyl-pyridine

Add phosphorus oxychloride (15 mL) to 4-tert-butyl-2-methyl-pyridine 1-oxide (2.00 g, 12.10 mmol) and heat to 100° C. for 36 hours. Evaporate off the excess phosphorus oxychloride. Treat the oil cautiously with ice and water with stirring and make basic by treatment with aqueous bicarbonate solution. Extract with dichloromethane (3×75 mL) and pool, desiccate, filter, and concentrated. Chromatograph the crude product on silica using a gradient of (0→5→8%) ethyl acetate in dichloromethane to afford the title compound (0.82 g, 4.46 mmol). MS (ESI), m/z 184 (M+1).

D. 4-tert-Butyl-6-methyl-pyridin-2-ylamine

Combine 2-chloro-6-methyl-4-tert-butyl-pyridine (0.18 g, 1.00 mmol), benzophenone imine (0.22 g, 1.2 mmol), sodium tert-butoxide (0.14 g, 1.4 mmol), BINAP (0.09, 0.02 mmol) in a round bottom flask and suspended in toluene. Bubble nitrogen through the suspension for 5 minutes, then add $Pd_2(dba)_3$ (0.03 g, 0.03 mmol) and heat to 90° C. for 18 hours. Load the crude reaction onto silica and elute with a (0→3%) methanol in dichloromethane to afford the imine intermediate, which is then taken up in tetrahydrofuran (6 mL) and 5N HCl (6 mL) and stirred at 60° C. for 2.5 hours. Concentrate the reaction to dryness, then re-dissolve in methanol and SCX to afford the title compound (0.07 g, 0.43 mmol). MS (ESI), m/z 165 (M+1).

Preparation 169

4-tert-Butyl-6-dimethylaminomethyl-pyridin-2-ylamine

A. 2-Bromomethyl-4-tert-butyl-6-chloro-pyridine

Dissolve 2-chloro-6-methyl-4-tert-butyl-pyridine (3.00 g, 16.33 mmol), N-bromosuccinimide (3.20 g, 17.97 mmol) and AIBN (0.03 g, 0.16 mmol) in carbon tetrachloride (60 mL) and heat to reflux. After heating for 6 hours, stir the contents overnight at ambient temperature. The contents are then concentrated to dryness and dry loaded onto a silica plug and eluted with dichloromethane to obtain the title compound (1.90 g, 7.23 mmol). MS(ES), m/z 263 (M+1).

B. (4-tert-Butyl-6-chloro-pyridin-2-ylmethyl)-dimethylamine

Stir a solution of 2N dimethylamine (9.00 mL, 18.08 mmol) in tetrahydrofuran, N,N-diisopropylethylamine (2.80 g, 3.80 mL, 21.69 mmol) while adding a solution of 2-bromomethyl-4-tert-butyl-6-chloro-pyridine (1.90 g, 7.23 mmol) in tetrahydrofuran (20 mL). Stir for 2.5 hours at ambient temperature, dilute the reaction with aqueous sodium bicarbonate (80 mL) and extract the aqueous layer with ethyl acetate (3×75 mL). Pool, desiccate, filter and concentrate the organics to yield the title compound (99%) (1.64 g, 7.23 mmol). MS(ES), m/z 227 (M+1).

C) Benzyl-(4-tert-butyl-6-dimethylaminomethyl-pyridin-2-yl)-amine

In method similar to that for Preparation 168 D, treat 4-tert-butyl-6-chloro-pyridin-2-ylmethyl)-dimethylamine (1.64 g, 7.23 mmol) with benzylamine rather than benzophenone imine to provide after chromatography (0.88 g, 2.96 mmol).

D) 4-tert-Butyl-6-dimethylaminomethyl-pyridin-2-ylamine

Add concentrated sulfuric acid (20 mL) to benzyl-(4-tert-butyl-6-dimethylaminomethyl-pyridin-2-yl)-amine (0.88 g, 2.96 mmol) at ambient temperature and stir for 1.5 hours. Adjust the pH of the aqueous solution carefully with saturated sodium bicarbonate solution. Extract the aqueous phase with ethyl acetate (3×75 mL) and pool, desiccate, filter and concentrate to a residue. Dissolve the residue in methanol and subject the material to SCX chromatography. Concentrate the methanolic ammonia eluent and plug chromatograph the amine to provide the title compound (0.56 g, 2.7 mmol). MS(ES), m/z 208 (M+1).

Prepare the following intermediates using a procedure similar to Preparation 169:

| Preparation | Name | Physical Data MS (ES), m/z |
|---|---|---|
| 170 | 4-tert-Butyl-6-morpholin-4-ylmethyl-pyridin-2-ylamine | 250 (M + 1). |
| 171 | 4-tert-Butyl-6-pyrrolidin-1-ylmethyl-pyridin-2-ylamine | 234 (M + 1). |

Prepare the following according to procedures similar to Preparation 128:

| Preparation | Name | Physical Data MS (ES), m/z |
|---|---|---|
| 172 | 2-(4-Bromo-2-fluoro-phenyl)-N-(4-tert-butyl-6-dimethylaminomethyl-pyridin-2-yl)-acetamide | 422/424 (M + 2). |
| 173 | 2-(4-Bromo-2-fluoro-phenyl)-N-(4-pyrrolidin-1-ylmethyl-pyridin-2-yl)-acetamide | 448/450 (M + 2). |

Preparation 174

N-(4-tert-Butyl-6-methyl-pyridin-2-yl)-2-[2-fluoro-4-(7-pyridin-4-yl-imidazo[1,2-a]pyridin-3-yl)-phenyl]-acetamide A. [2-Fluoro-4-(7-pyridin-4-yl-imidazo[1,2-a]pyridin-3-yl)-phenyl]-acetic acid tert-butyl ester Couple 4-bromo-2-fluoro-phenylacetic acid, tert-butyl ester (3.65 g, 18.68 mmol) with 7-pyridin-4-yl-imidazo[1,2-a]pyridine (5.40 g, 18.68 mmol) as described in Preparation 153. MS(ES), m/z 404 (M+1).

B. [2-Fluoro-4-(7-pyridin-4-yl-imidazo[1,2-a]pyridin-3-yl)-phenyl]-acetic acid dihydrochloride Suspend [2-fluoro-4-(7-pyridin-4-yl-imidazo[1,2-a]pyridin-3-yl)-phenyl]-acetic acid tert-butyl ester (1.36 g, 3.369 mmol) in water (8 mL) and 4N hydrochloric acid in dioxane (40 mL) and stir at ambient temperature for 3 hours. Concentration under vacuum quantitatively provides the title compound (1.42 g, 3.69 mmol). MS(ES), m/z 348 (M+1).

C. N-(4-tert-Butyl-6-methyl-pyridin-2-yl)-2-[2-fluoro-4-(7-pyridin-4-yl-imidazo[1,2-a]pyridin-3-yl)-phenyl]-acetamide Combine [2-fluoro-4-(7-pyridin-4-yl-imidazo[1,2-a]pyridin-3-yl)-phenyl]-acetic acid dihydrochloride (0.66 g, 1.57 mmol), 4-tert-butyl-6-methyl-pyridin-2-yl-amine (0.26 g, 1.57 mmol), HATU (0.72 g, 1.57 mmol), diisopropylethylamine (8.12 g, 11.2 mL, 6.28 mmol) in DMF (10 mL) and stir at ambient temperature for 3 hours. Pour the reaction contents onto a pre-washed (with methanol) Varian SCX column (25 g) and wash the column with portions (30 mL) of dichloromethane (2×) and methanol (3×). Elute the product with 2N methanolic ammonia (75 mL) and concentrate the solution to dryness. Chromatograph the crude product on silica using (0-5%) methanol in dichloromethane. Recrystallization from dichloromethane/ether/hexanes provides N-(4-tert-Butyl-6-methyl-pyridin-2-yl)-2-[2-fluoro-4-(7-pyridin-4-yl-imidazo[1,2-a]pyridin-3-yl)-phenyl]-acetamide (0.17 g). MS(ES), m/z 494 (M+1).

Preparation 175

{4-[3-(4-Aminomethyl-phenyl)-imidazo[1,2-a]pyridin-7-yl]-phenyl}-(4-methyl-piperazin-1-yl)-methanone, bis hydrochloride Combine (4-{7-[4-(4-methyl-piperazine-1-carbonyl)-phenyl]-imidazo[1,2-a]pyridin-3-yl}-benzyl)-carbamic acid tert-butyl ester (0.87 g, 1.65 mmol), 4N HCl in 1,4-dioxane (15 mL, 60 mmol) in 1,4-dioxane (35 mL) and stir overnight (16 hours). Concentrate slurry to a residue. Dissolve residue in methanol (50 mL) and concentrate to afford the title compound (0.90 g, 100%). MS(ES), m/z 426 (M+1 for free base).

Preparation 176

2-(4-Bromo-2-fluoro-phenyl)-N-(5-tert-butyl-[1,3,4]thiadiazol-2-yl)-acetamide

Dissolve 4-bromo-2-fluoro-phenyl)-acetic acid (1.10 g, 4.72 mmol) and N-(5-tert-butyl-[1,3,4]thiaziazol-2-yl)amine (0.89 g, 5.67 mmol) in anhydrous tetrahydrofuran (10 mL). Add N-methyl morpholine (0.62 mL, 5.67 mmol) and DMTMM (1.57 g, 5.67 mmol). Stir the reaction mixture for 2 hours at room temperature. Concentrate to solid. Add water (40 mL) and stir vigorously for 10 minutes. Filter off the white solid and recrystallize from ethyl acetate and hexane to provide 1.13 g of the product as a white solid. Concentrate the filtrate and purify via flash silica gel chromatography (0-20% Ethyl acetate/hexane) to yield a further 0.51 g, giving a combined yield of 1.64 g (4.39 mmol, 93%). MS (ES), m/z 372/374 (M+1).

Example 1

1-(5-tert-Butyl-2-p-tolyl-2H-pyrazol-3-yl)-3-[4-(7-thiophen-3-yl-imidazo[1,2-a]pyridin-3-yl)-benzyl]-urea

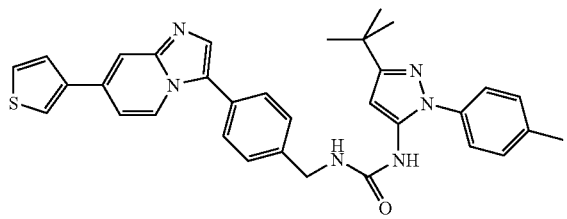

Dissolve 4-(7-thien-3-yl-imidazo[1,2-a]pyridin-3-yl)-benzylamine (0.058 g, 0.19 mmol), (5-tert-butyl-2-p-tolyl-2H-pyrazol-3-yl)-carbamic acid 2,2,2-trichloro-ethyl ester (0.093 g, 0.23 mmol) and diisopropylethylamine (0.071 g, 0.55 mmol) in DMSO (3.6 mL). Heat the mixture at 62° C. for 8 hours. After evaporation of solvent, dilute the reaction with water and ethyl acetate. Extract the water phase with ethyl acetate and wash the combined organic layers with saturated aqueous saturated sodium chloride and evaporate to dryness. Purify the residue by silica gel column chromatography (dichlromethane/ethyl acetate gradient) to give 0.023 g (21% yield) of desired compound: MS(ES), m/z 561 (M+1).

Prepare the following according to procedures similar to Example 1:

| Ex. | Compound Name | Physical Data MS (ES), m/z |
|---|---|---|
| 2 | 1-(5-tert-Butyl-2-methyl-2H-pyrazol-3-yl)-3-{4-[7-(thien-3-yl)-imidazo[1,2-a]pyridin-3-yl]-benzyl}-urea | 485 (M + 1) |
| 3 | 1-(5-tert-Butyl-2-p-tolyl-2H-pyrazol-3-yl)-3-{4-[7-(4-methanesulfonyl-phenyl)-imidazo[1,2-a]pyridin-3-yl]-benzyl}-urea | 633 (M + 1) |
| 4 | 1-(5-tert-Butyl-2-p-tolyl-2H-pyrazol-3-yl)-3-{4-[7-(4-methanesulfonyl-phenyl)-imidazo[1,2-a]pyridin-3-yl]-phenyl}-urea, trifluoroacetate | 617 (M − 1) |
| 5 | 1-(5-tert-Butyl-2-methyl-2H-pyrazol-3-yl)-3-{4-[7-(4-methanesulfonyl-phenyl)-imidazo[1,2-a]pyridin-3-yl]-phenyl}-urea | 543 (M + 1) |
| 6 | 1-(5-tert-Butyl-[1,3,4]thiadiazol-2-yl)-3-{4-[7-(4-methanesulfonyl-phenyl)-imidazo[1,2-a]pyridin-3-yl]-phenyl}-urea | 547 (M + 1) |
| 7 | 1-(5-tert-Butyl-2H-pyrazol-3-yl)-3-{4-[7-(4-methanesulfonyl-phenyl)-imidazo[1,2-a]pyridin-3-yl]-benzyl}-urea, bis-trifluoroacetate | 543 (M + 1) |
| 8 | 1-[3-(1-Ethyl-1-methyl-propyl)-isoxazol-5-yl]-3-{4-[7-(4-methane-sulfonyl-phenyl)-imidazo[1,2-a]pyridin-3-yl]-benzyl}-urea | 572 (M + 1) |
| 9 | 1-[3-(1,1-Dimethyl-butyl)-isoxazol-5-yl]-3-{4-[7-(4-methane-sulfonyl-phenyl)-imidazo[1,2-a]pyridin-3-yl]-benzyl}-urea | 572 (M + 1) |
| 10 | 1-(5-tert-Butyl-2-methyl-2H-pyrazol-3-yl)-3-{4-[7-(4-methanesulfonyl-phenyl)-imidazo[1,2-a]pyridin-3-yl]-benzyl}-urea | 557 (M + 1) |

-continued

| Ex. | Compound Name | Physical Data MS (ES), m/z |
|---|---|---|
| 11 | 1-(3-tert-Butyl-isoxazol-5-yl)-3-{4-[7-(4-methanesulfonyl-phenyl)-imidazo[1,2-a]pyridin-3-yl]-benzyl}-urea | 544 (M + 1) |
| 12 | 1-(5-tert-Butyl-[1,3,4]thiadiazol-2-yl)-3-{4-[7-(4-methanesulfonyl-phenyl)-imidazo[1,2-a]pyridin-3-yl]-benzyl}-urea | 561 (M + 1) |
| 13 | 1-(5-tert-Butyl-isoxazol-3-yl)-3-{4-[7-(4-methanesulfonyl-phenyl)-imidazo[1,2-a]pyridin-3-yl]-benzyl}-urea | 544 (M + 1) |
| 14 | 1-(5-tert-Butyl-isoxazol-3-yl)-3-{4-[7-(4-methanesulfonyl-phenyl)-imidazo[1,2-a]pyridin-3-yl]-phenyl}-urea | 530 (M + 1) |
| 15 | 1-(5-tert-Butyl-2-methyl-2H-pyrazol-3-yl)-3-[4-(7-pyridin-4-yl-imidazo[1,2-a]pyridin-3-yl)-benzyl]-urea | 480 (M + 1) |
| 16 | 1-(5-tert-Butyl-2-methyl-2H-pyrazol-3-yl)-3-[4-(7-pyridin-4-yl-imidazo[1,2-a]pyridin-3-yl)-phenyl]-urea | 466 (M + 1) |
| 17 | 1-(5-tert-Butyl-[1,3,4]thiadiazol-2-yl)-3-[4-(7-pyridin-4-yl-imidazo[1,2-a]pyridin-3-yl)-phenyl]-urea | 470 (M + 1) |
| 18 | 1-(5-tert-Butyl-isoxazol-3-yl)-3-[4-(7-pyridin-4-yl-imidazo[1,2-a]pyridin-3-yl)-phenyl]-urea | 453 (M + 1) |
| 19 | 1-(5-tert-Butyl-2H-pyrazol-3-yl)-3-[4-(7-pyridin-4-yl-imidazo[1,2-a]pyridin-3-yl)-phenyl]-urea | 452 (M + 1) |
| 20 | 1-(5-tert-Butyl-[1,3,4]thiadiazol-2-yl)-3-[4-(7-pyridin-4-yl-imidazo[1,2-a]pyridin-3-yl)-benzyl]-urea | 484 (M + 1) |
| 21 | 1-(5-tert-Butyl-isoxazol-3-yl)-3-[4-(7-pyridin-4-yl-imidazo[1,2-a]pyridin-3-yl)-benzyl]-urea | 467 (M + 1) |
| 22 | 1-(3-tert-Butyl-isoxazol-5-yl)-3-[4-(7-pyridin-4-yl-imidazo[1,2-a]pyridin-3-yl)-benzyl]-urea | 467 (M + 1) |
| 23 | 1-(5-tert-Butyl-2H-pyrazol-3-yl)-3-[4-(7-pyridin-4-yl-imidazo[1,2-a]pyridin-3-yl)-benzyl]-urea | 466 (M + 1) |
| 24 | 1-(5-tert-Butyl-2-methyl-2H-pyrazol-3-yl)-3-[4-(7-pyridin-3-yl-imidazo[1,2-a]pyridin-3-yl)-phenyl]-urea | 466 (M + 1) |
| 25 | 1-(5-tert-Butyl-2-methyl-2H-pyrazol-3-yl)-3-[4-(7-pyridin-2-yl-imidazo[1,2-a]pyridin-3-yl)-phenyl]-urea | 466 (M + 1) |
| 26 | 1-(5-tert-Butyl-isoxazol-3-yl)-3-[4-(7-thiazol-2-yl-imidazo[1,2-a]pyridin-3-yl-phenyl]-urea | 459 (M + 1) |
| 27 | 1-(3-tert-Butyl-isoxazol-5-yl)-3-[4-(7-pyridin-4-yl-imidazo[1,2-a]pyridin-3-yl)-phenyl]-urea | 453 (M + 1) |
| 28 | 1-(5-tert-Butyl-2-p-tolyl-2H-pyrazol-3-yl)-3-[3-(7-thien-3-yl-imidazo[1,2-a]pyridin-3-yl)-benzyl]-urea | 561 (M + 1) |
| 29 | 1-(5-tert-Butyl-2H-pyrazol-3-yl)-3-[3-(7-pyridin-4-yl-imidazo[1,2-a]pyridin-3-yl)-benzyl]-urea | 466 (M + 1) |
| 30 | 1-(5-tert-Butyl-2-p-tolyl-2H-pyrazol-3-yl)-3-[3-(7-pyridin-4-yl-imidazo[1,2-a]pyridin-3-yl)-benzyl]-urea | 556 (M + 1) |
| 31 | 1-(5-tert-Butyl-isoxazol-3-yl)-3-[3-(7-pyridin-4-yl-imidazo[1,2-a]pyridin-3-yl)-benzyl]-urea | 467 (M + 1) |
| 32 | 1-(3-tert-Butyl-isoxazol-5-yl)-3-[3-(7-pyridin-4-yl-imidazo[1,2-a]pyridin-3-yl)-benzyl]-urea | 467 (M + 1) |
| 33 | 1-(5-tert-Butyl-[1,3,4]thiadiazol-2-yl)-3-[3-(7-pyridin-4-yl-imidazo[1,2-a]pyridin-3-yl)-benzyl]-urea | 484 (M + 1) |
| 34 | 1-(5-tert-Butyl-[1,3,4]thiadiazol-2-yl)-3-[4-(7-thiazol-2-yl-imidazo[1,2-a]pyridin-3-yl)-phenyl]-urea | 476 (M + 1) |
| 35 | 1-(3-tert-Butyl-isoxazol-5-yl)-3-[4-(7-thiazol-2-yl-imidazo[1,2-a]pyridin-3-yl)-benzyl]-urea | 473 (M + 1) |
| 36 | 1-(5-n-Propyl-thiazol-2-yl)-3-[4-(7-pyridin-4-yl-imidazo[1,2-a]pyridin-3-yl)-phenyl]-urea | 455 (M + 1) |
| 37 | 1-(5-Isopropyl-thiazol-2-yl)-3-[4-(7-pyridin-4-yl-imidazo[1,2-a]pyridin-3-yl)-phenyl]-urea | 455 (M + 1) |
| 38 | 1-(5-Isopropyl-thiazol-2-yl)-3-[4-(7-pyridin-4-yl-imidazo[1,2-a]pyridin-3-yl)-benzyl]-urea | 469 (M + 1) |
| 39 | 1-(5-tert-Butyl-thiazol-2-yl)-3-[4-(7-pyridin-4-yl-imidazo[1,2-a]pyridin-3-yl)-benzyl]-urea, methane sulfonate | 483 (M + 1) |
| 40 | 1-(4-tert-Butyl-thiazol-2-yl)-3-[4-(7-pyridin-4-yl-imidazo[1,2-a]pyridin-3-yl)-benzyl]-urea | 483 (M + 1) |
| 41 | 1-(5-Ethyl-thiazol-2-yl)-3-[4-(7-pyridin-4-yl-imidazo[1,2-a]pyridin-3-yl)-phenyl]-urea methanesulfonate | 441 (M + 1) |
| 42 | 1-(5-tert-Butyl-thiazol-2-yl)-3-[4-(7-pyridin-4-yl-imidazo[1,2-a]pyridin-3-yl)-phenyl]-urea methanesulfonate | 469 (M + 1) |
| 43 | 1-(5-n-Propyl-thiazol-2-yl)-3-[4-(7-pyridin-4-yl-imidazo[1,2-a]pyridin-3-yl)-benzyl]-urea methanesulfonate | 469 (M + 1) |
| 44 | 1-(5-Isopropyl-thiazol-2-yl)-3-[4-(7-pyridin-4-yl-imidazo[1,2-a]pyridin-3-yl)-benzyl]-urea methanesulfonate | 469 (M + 1) |
| 45 | 1-(4-tert-Butyl-thiazol-2-yl)-3-[4-(7-pyridin-4-yl-imidazo[1,2-a]pyridin-3-yl)-benzyl]-urea methanesulfonate | 483 (M + 1) |
| 46 | 1-(5-tert-Butyl-isoxazol-3-yl)-3-{4-[7-(1H-[1,2,3]triazol-4-yl)-imidazo[1,2-a]pyridin-3-yl]-phenyl}-urea | 443 (M + 1) |

-continued

| Ex. | Compound Name | Physical Data MS (ES), m/z |
|---|---|---|
| 47 | 1-(5-tert-Butyl-isoxazol-3-yl)-3-{4-[7-(2-methyl-2H-[1,2,4]triazol-3-yl)-imidazo[1,2-a]pyridin-3-yl]-phenyl}-urea. | 457 (M + 1) |
| 48 | 1-{4-[7-(2-Methyl-2H-[1,2,4]triazol-3-yl)-imidazo[1,2-a]pyridin-3-yl]-phenyl}-3-(3-trifluoromethyl-phenyl)-urea | 478 (M + 1) |
| 49 | 1-(5-tert-Butyl-2H-pyrazol-3-yl)-3-{4-[7-(2-methyl-2H-[1,2,4]triazol-3-yl)-imidazo[1,2-a]pyridin-3-yl]-phenyl}-urea | 456 (M + 1) |
| 50 | 1-(5-tert-Butyl-isoxazol-3-yl)-3-{4-[7-(2-methyl-2H-[1,2,4]triazol-3-yl)-imidazo[1,2-a]pyridin-3-yl]-benzyl}-urea | 471 (M + 1) |
| 51 | 1-{4-[7-(2-Methyl-2H-[1,2,4]triazol-3-yl)-imidazo[1,2-a]pyridin-3-yl]-benzyl}-3-(3-trifluoromethyl-phenyl)-urea | 492 (M + 1) |
| 52 | 1-(5-tert-Butyl-isoxazol-3-yl)-3-[4-(7-pyridin-3-yl-imidazo[1,2-a]pyridin-3-yl)-phenyl]-urea methanesulfonate | 453 (M + 1) |
| 53 | 1-(5-tert-Butyl-isoxazol-3-yl)-3-[4-(7-pyridin-2-yl-imidazo[1,2-a]pyridin-3-yl)-phenyl]-urea | 453 (M + 1) |
| 54 | 1-(5-tert-Butyl-thiazol-2-yl)-3-[4-(7-pyridin-4-yl-imidazo[1,2-a]pyridin-3-yl)-benzyl]-urea | 483 (M + 1) |
| 55 | 1-(5-tert-Butyl-thiazol-2-yl)-3-{4-[7-(4-methanesulfonyl-phenyl)-imidazo[1,2-a]pyridin-3-yl]-benzyl}-urea | 560 (M + 1) |
| 56 | 1-(5-tert-Butyl-isoxazol-3-yl)-3-[2-chloro-4-(7-pyridin-4-yl-imidazo[1,2-a]pyridin-3-yl)-phenyl]-urea | 487 (M + 1) |
| 57 | 1-(5-tert-Butyl-isoxazol-3-yl)-3-{4-[7-(6-dimethylamino-pyridin-3-yl)-imidazo[1,2-a]pyridin-3-yl]-phenyl}-urea | 496 (M + 1) |
| 58 | 1-(5-tert-Butyl-thiazol-2-yl)-3-{4-[7-(1-methyl-1H-imidazol-2-yl)-imidazo[1,2-a]pyridin-3-yl]-benzyl}-urea[a] | 486.0 (M + 1) |
| 59 | 1-[4-(7-Pyridin-4-yl-imidazo[1,2-a]pyridin-3-yl)-phenyl]-3-(4-trifluoromethyl-pyridin-2-yl)-urea | 475 (M + 1) |
| 60 | 1-[4-(7-Pyridin-4-yl-imidazo[1,2-a]pyridin-3-yl)-benzyl]-3-(4-trifluoromethyl-pyridin-2-yl)-urea | 489 (M + 1) |
| 61 | 1-[3-(1-Methyl-1-ethyl-propyl)-isoxazol-5-yl]-3-[4-(7-pyridin-4-yl-imidazo[1,2-a]pyridin-3-yl)-benzyl]-urea | 495 (M + 1) |
| 62 | 1-[3-(1,1-Dimethyl-butyl)-isoxazol-5-yl]-3-[4-(7-pyridin-4-yl-imidazo[1,2-a]pyridin-3-yl)-benzyl]-urea | 495 (M + 1) |

[a] 72° C. 18 hours. Pass through a pre-washed SCX column; chromatograph on silica gel; and slurry in EtOAc with a trace of MeOH.

Example 63

1-(5-tert-Butyl-isoxazol-3-yl)-3-(2-fluoro-4-{7-[4-(4-isopropyl-piperazine-1-carbonyl)-phenyl]-imidazo[1,2-a]pyridin-3-yl}-phenyl)-urea

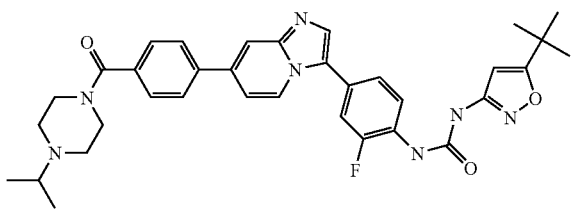

Dissolve 1-(5-tert-butyl-isoxazol-3-yl)-3-(2-fluoro-4-{7-[4-(piperazine-1-carbonyl)-phenyl]-imidazo[1,2-a]pyridin-3-yl}-phenyl)-urea hydrochloride (0.290 g, 0.469 mmol) in methanol (5 mL) and acetone (0.041 mL, 0.563 mmol). Add acetic acid (0.032 mL, 0.563 mmol); stir the mixture for five minutes. Add sodium cyanoboro-hydride (0.053 g, 0.845 mmol). Stir the mixture at room temperature for 14 hours. Concentrate to dryness and quench with 1 N HCl (5 mL). Partition between ethyl acetate and 1 N NaOH, wash with aqueous saturated sodium chloride, dry the organics over magnesium sulfate, filter, and concentrate. Purify by column chromatography (hexanes→5% methanol in dichloromethane→10% methanol in dichloromethane→10% 2 M NH₃ in methanol in dichloromethane) to afford product (0.019 g, 7%). MS(ES), m/z 624 (M+1).

Example 64

1-{4-[7-(4-Methanesulfonyl-phenyl)-imidazo[1,2-a]pyridin-3-yl]-benzyl}-3-(3-trifluoromethyl-phenyl)-urea

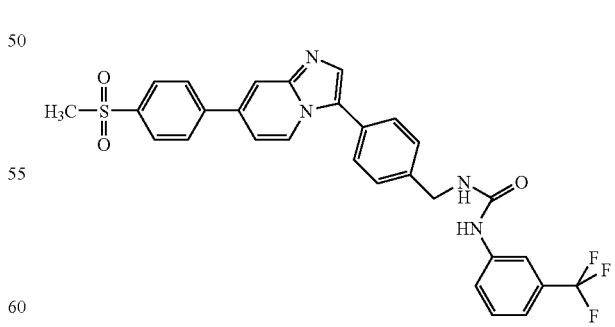

Dissolve 4-[7-(4-methanesulfonyl-phenyl)-imidazo[1,2-a]pyridin-3-yl]-benzylamine (2.37 g, 6.28 mmol) and diisopropylethylamine (2.44 g, 3.28 mL, 18.84 mmol) in dimethylsulfoxide under a nitrogen environment at room temperature. Add 3-trifluoromethylphenylisocyanate (1.17 g, 6.28 mmol) and stir the mixture for 2.5 hours. Pour the reaction contents onto a Varian SCX column (50 g) prewashed with methanol. Wash the column with dichloromethane, 1:1 methanol/dichloromethane and methanol (150 mL each). Elute the title compound with 2 N NH$_3$/methanol (300 mL). Concentrate the methanolic solution to dryness and chromatograph on silica using 0→3→5→10% methanol/dichloromethane over 4, 15 and 30 minutes, respectively. Dissolve the product in heated CHCl$_3$ (65 mL), followed by treatment with hexanes (5 mL) and cooling. Dry the resulting precipitate in vacuo to yield the product (2.33 g, 66%). MS(ES), m/z 565 (M+1).

Prepare the following according to procedures similar to Example 64:

| Ex. | Compound Name | Physical Data MS (ES) (m/z) |
|---|---|---|
| 65 | 1-[4-(7-Thien-3-yl-imidazo[1,2-a]pyridin-3-yl)-benzyl]-3-(3-trifluoromethyl-phenyl)-urea | 493 (M + 1), |
| 66 | 1-(4-Chloro-3-trifluoromethyl-phenyl)-3-[4-(7-thien-3-yl-imidazo[1,2-a]pyridin-3-yl)-benzyl]-urea | 527 (M + 1) |
| 67 | 1-{4-[7-(4-Methanesulfonyl-phenyl)-imidazo[1,2-a]pyridin-3-yl]-phenyl}-3-(3-trifluoromethyl-phenyl)-urea | 551 (M − 1) |
| 68 | 1-{4-[7-(4-Methanesulfonyl-phenyl)-imidazo[1,2-a]pyridin-3-yl]-benzyl}-3-(4-trifluoromethyl-phenyl)-urea | 565 (M + 1) |
| 69 | 1-(4-tert-Butyl-phenyl)-3-{4-[7-(4-methanesulfonyl-phenyl)-imidazo[1,2-a]pyridin-3-yl]-benzyl}-urea | 553 (M + 1) |
| 70 | 1-(4-difluoromethoxy-phenyl)-3-{4-[7-(4-methanesulfonyl-phenyl)-imidazo[1,2-a]pyridin-3-yl]-benzyl}-urea | 563 (M + 1) |
| 71 | 1-{4-[7-(4-Methanesulfonyl-phenyl)-imidazo[1,2-a]pyridin-3-yl]-thiazol-2-ylmethyl}-3-(3-trifluoromethyl-phenyl)-urea | 572 (M + 1) |
| 72 | 1-{4-[7-(4-Methanesulfonyl-phenyl)-imidazo[1,2-a]pyridin-3-yl]-benzyl}-3-(2-trifluoromethyl-phenyl)-urea | 565 (M + 1) |
| 73 | 1-(4-Bromo-phenyl)-3-{4-[7-(4-methanesulfonyl-phenyl)-imidazo[1,2-a]pyridin-3-yl]-benzyl}-urea | 575 (M + 1) |
| 74 | 1-(4-Isopropyl-phenyl)-3-{4-[7-(4-methanesulfonyl-phenyl)-imidazo[1,2-a]pyridin-3-yl]-benzyl}-urea | 539 (M + 1) |
| 75 | 1-{4-[7-(4-Methanesulfonyl-phenyl)-imidazo[1,2-a]pyridin-3-yl]-benzyl}-3-p-tolyl-urea | 511 (M + 1) |
| 76 | 1-{4-[7-(4-Methanesulfonyl-phenyl)-imidazo[1,2-a]pyridin-3-yl]-benzyl}-3-(4-phenoxy-phenyl)-urea | 589 (M + 1) |
| 77 | 1-(4-Chloro-phenyl)-3-{4-[7-(4-methanesulfonyl-phenyl)-imidazo[1,2-a]pyridin-3-yl]-benzyl}-urea | 531 (M + 1) |
| 78 | 1-{4-[7-(4-Methanesulfonyl-phenyl)-imidazo[1,2-a]pyridin-3-yl]-benzyl}-3-(3-methoxy-phenyl)-urea | 527 (M + 1) |
| 79 | 1-{4-[7-(4-Methanesulfonyl-phenyl)-imidazo[1,2-a]pyridin-3-yl]-benzyl}-3-(4-methoxy-phenyl)-urea | 527 (M + 1) |
| 80 | 1-{4-[7-(4-Methanesulfonyl-phenyl)-imidazo[1,2-a]pyridin-3-yl]-benzyl}-3-(4-trifluoromethoxy-phenyl)-urea | 581 (M + 1) |
| 81 | 1-[4-(7-Pyridin-4-yl-imidazo[1,2-a]pyridin-3-yl)-benzyl]-3-(3-trifluoromethyl-phenyl)-urea | 488 (M + 1) |
| 82 | 1-[4-(7-Pyridin-4-yl-imidazo[1,2-a]pyridin-3-yl)-benzyl]-3-(2-trifluoromethyl-phenyl)-urea | 488 (M + 1) |
| 83 | 1-[3-(7-Pyridin-4-yl-imidazo[1,2-a]pyridin-3-yl)-benzyl]-3-(4-trifluoromethyl-phenyl)-urea | 488 (M + 1) |
| 84 | 1-(4-Isopropyl-phenyl)-3-[3-(7-pyridin-4-yl-imidazo[1,2-a]pyridin-3-yl)-benzyl]-urea | 462 (M + 1) |
| 85 | 1-[3-(7-Pyridin-4-yl-imidazo[1,2-a]pyridin-3-yl)-benzyl]-3-(2-trifluoromethyl-phenyl)-urea | 488 (M + 1) |
| 86 | 1-(4-Difluoromethoxy-phenyl)-3-[4-(7-pyridin-4-yl-imidazo[1,2-a]pyridin-3-yl)-phenyl]-urea | 472 (M + 1) |
| 87 | 1-[4-(7-Pyridin-4-yl-imidazo[1,2-a]pyridin-3-yl)-phenyl]-3-(4-trifluoromethyl-phenyl)-urea | 474 (M + 1) |
| 88 | 1-[3-(7-Pyridin-4-yl-imidazo[1,2-a]pyridin-3-yl)-benzyl]-3-(3-trifluoromethyl-phenyl)-urea | 488 (M + 1) |
| 89 | 1-(4-Isopropyl-phenyl)-3-[4-(7-pyridin-4-yl-imidazo[1,2-a]pyridin-3-yl)-phenyl]-urea | 448 (M + 1) |
| 90 | 1-(4-tert-Butyl-phenyl)-3-[4-(7-pyridin-4-yl-imidazo[1,2-a]pyridin-3-yl)-phenyl]-urea | 462 (M + 1) |
| 91 | 1-[4-(7-Thiazol-2-yl-imidazo[1,2-a]pyridin-3-yl)-phenyl]-3-(3-trifluoromethyl-phenyl)-urea | 480 (M + 1) |
| 92 | 1-[4-Thiazol-2-yl-imidazo[1,2-a]pyridin-3-yl)-benzyl]-3-(3-trifluoromethyl-phenyl)-urea | 494 (M + 1) |
| 93 | 1-[4-(7-Pyridin-3-yl-imidazo[1,2-a]pyridin-3-yl)-benzyl]-3-(3-trifluoromethyl-phenyl)-urea | 488 (M + 1) |
| 94 | 1-[4-(7-Pyridin-2-yl-imidazo[1,2-a]pyridin-3-yl)-benzyl]-3-(3-trifluoromethyl-phenyl)-urea | 488 (M + 1) |
| 95 | 1-{4-[7-(2-Diethylaminomethyl-pyridin-4-yl)-imidazo[1,2-a]pyridin-3-yl]-benzyl}-3-(3-trifluoromethyl-phenyl)-urea | 573 (M + 1) |
| 96 | 1-{4-[7-(5-Diethylaminomethyl-pyridin-2-yl)-imidazo[1,2-a]pyridin-3-yl]-benzyl}-3-(3-trifluoromethyl-phenyl)-urea | 573 (M + 1) |

-continued

| Ex. | Compound Name | Physical Data MS (ES) (m/z) |
|---|---|---|
| 97 | 1-(2-Fluoro-5-trifluoromethyl-phenyl)-3-[4-(7-pyridin-4-yl-imidazo[1,2-a]pyridin-3-yl)-benzyl]-urea | 506 (M + 1) |
| 98 | 1-{4-[7-(1H-Pyrazol-4-yl)-imidazo[1,2-a]pyridin-3-yl]-benzyl}-3-(3-trifluoromethyl-phenyl)-urea | 477 (M + 1) |

Example 99

1-(3-Chloro-phenyl)-3-{4-[7-(6-piperazin-1-yl-pyridin-3-yl)-imidazo[1,2-a]pyridin-3-yl]-phenyl}-urea

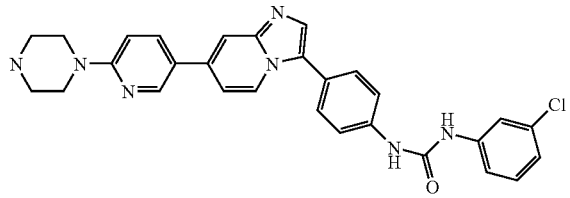

A. 1-{4-[7-(6-Fluoro-pyridin-3-yl)-imidazo[1,2-a]pyridin-3-yl]-phenyl}-3-(3-trifluoromethyl-phenyl)-urea Prepare with procedures similar to example 55. MS(ES), m/z 458 (M+1)

B. 1-(3-Chloro-phenyl)-3-{4-[7-(6-piperazin-1-yl-pyridin-3-yl)-imidazo[1,2-a]pyridin-3-yl]-phenyl}-urea Charge 1-{4-[7-(6-fluoro-pyridin-3-yl)-imidazo[1,2-a]pyridin-3-yl]-phenyl}-3-(3-trifluoromethyl-phenyl)-urea (270 mg, 0.41 mmol), piperazine (53 mg, 0.62 mmol), DMSO (12 mL), K$_2$CO$_3$ (283 mg, 2.1 mmol) into septum capped vial. Heat to 70° C. and mix 24 hours. Cool and add water. Dissolve in MeOH and purify with a Varian SCX® (25 g) column that is pre-washed with water and methanol, the product being eluted with (15%) 2 N NH$_3$ in methanol/(85%) DCM. Evaporate the product containing fractions under reduced pressure. Chromatograph using (40 g ISCO®) SiO$_2$ eluting with a gradient of 0% to 15% of 2 M NH$_3$ in MeOH with the balance CH$_2$Cl$_2$. Evaporate solvents, vacuum dry at 40° C. for 48 hours to afford the title compound 29.1 mg, (13.5%) 524.0 (ES), m/z (M+1).

Example 100

1-(3-tert-Butyl-phenyl)-3-[4-(7-pyridin-4-yl-imidazo[1,2-a]pyridin-3-yl)-phenyl]-urea

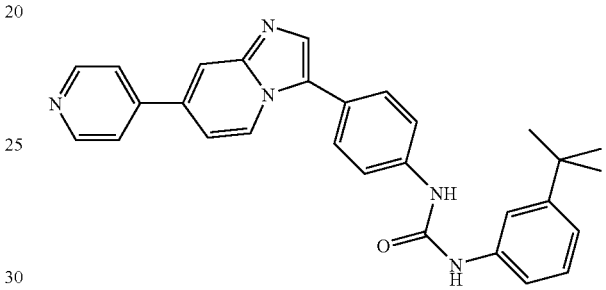

Dissolve phosgene (20% in toluene, 3.2 mL) in CHCl$_3$. To the cooled solution at 0° C. add dropwise a solution 3-t-butylaniline (0.149 g, 1.0 mmol) and triethylamine (0.202 g, 2.0 mmol) in CHCl$_3$. After completion stir the reaction mixture at room temperature for 6 hours. Remove the excess phosgene by a stream of nitrogen, followed by evaporation. Evaporate to dryness again with toluene. Use the crude carbamoyl chloride in the next step without purification.

Dissolve the above material in CHCl$_3$ and cool in an ice bath. To the solution add a solution of 7-(4-pyridinyl)-imidazopyridin-3-yl)-4-aniline (0.114 g, 0.40 mmol) and triethylamine (0.202 g). Stir the mixture at room temperature overnight. Dilute with CHCl$_3$. Adjust the pH of the solution to pH 4-5 and extract with CHCl$_3$ and wash the organic layer with saturated NaCl solution. Concentrate the combined organic layers and chromatograph on silica-gel to give the title compound, 105 mg (yield 57%). MS(ES), m/z 462 (M+1).

Prepare the following according to procedures similar to Example 100:

| Ex. | Compound Name | Physical Data MS (ES), (m/z) |
|---|---|---|
| 101 | 1-(4-Dimethylamino-phenyl)-3-{4-[7-(4-methanesulfonyl-phenyl)-imidazo[1,2-a]pyridin-3-yl]-benzyl}-urea | 540 (M + 1) |
| 102 | 1-(4-Methanesulfonyl-phenyl)-3-{4-[7-(4-methanesulfonyl-phenyl)-imidazo[1,2-a]pyridin-3-yl]-benzyl}-urea | 575 (M + 1) |

-continued

| Ex. | Compound Name | Physical Data MS (ES), (m/z) |
|---|---|---|
| 103 | 1-{4-[7-(4-Methanesulfonyl-phenyl)-imidazo[1,2-a]pyridin-3-yl]-benzyl}-3-{4-[(3,4-dimethyl-isoxazol-5-yl)aminosulfonyl]-phenyl}-urea | 671 (M + 1) |
| 104 | 1-(4-Cyano-phenyl)-3-{4-[7-(4-methanesulfonyl-phenyl)-imidazo[1,2-a]pyridin-3-yl]-benzyl}-urea | 522 (M + 1) |
| 105 | 1-(5-Methyl-thiazol-2-yl)-3-[3-(7-pyridin-4-yl-imidazo[1,2-a]pyridin-3-yl)-benzyl]-urea | 441 (M + 1) |

Example 106

1-(5-tert-Butyl-isoxazol-3-yl)-3-[4-(7-pyridin-4-yl-imidazo[1,2-a]pyridin-3-yl)-2-trifluoromethyl-phenyl]-urea

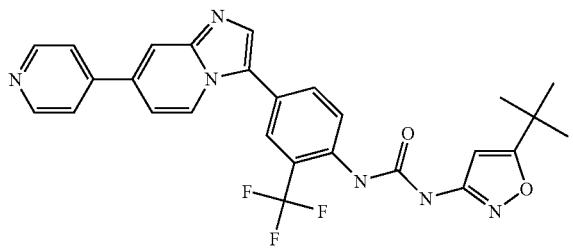

Dissolve 4-(7-pyridin-4-yl-imidazo[1,2-a]pyridin-3-yl)-2-trifluoromethyl-phenylamine (0.4 g, 1.1 mmol) in DCM (40 mL) under nitrogen. Add triethylamine (0.39 mL, 2.5 equiv.) followed by careful addition of triphosgene (0.13 g, 0.4 equiv.). After 15 minutes at room temperature, add 5-tert-butyl-isoxazol-3-ylamine (0.19 g, 1.2 equiv.) and stir for 2 days at room temperature. Quench with water then dilute with ethyl acetate. Wash organics with 1 N NaOH followed by aqueous saturated sodium chloride. Dry organics over MgSO$_4$ then filter and concentrate. Purify by reverse phase (5% MeCN:0.03% HCl in water→65% MeCN:0.03% HCl in water). Dilute product containing fractions with ethyl acetate then wash with 1 N NaOH followed by aqueous saturated sodium chloride. Dry the organics over MgSO$_4$ then filter and concentrate to give the freebase (0.33 g off-white solid, 56%). MS (ES), m/z 521.1 (M+1).

Prepare the following according to procedures similar to Example 106:

| Example | Name | MS |
|---|---|---|
| 107 | 1-[2-Fluoro-4-(7-pyridin-4-yl-imidazo[1,2-a]pyridin-3-yl)-phenyl]-3-(4-trifluoromethyl-pyridin-2-yl)-urea | 493 (M + 1) |
| 108 | 1-(5-tert-Butyl-thiazol-2-yl)-3-[2-fluoro-4-(7-pyridin-4-yl-imidazo[1,2-a]pyridin-3-yl)-phenyl]-urea | 487 (M + 1) |
| 109 | 1-(5-tert-Butyl-thiazol-2-yl)-3-[2-fluoro-4-(7-pyridin-2-yl-imidazo[1,2-a]pyridin-3-yl)-phenyl]-urea | 487 (M + 1) |
| 110 | 1-(5-tert-Butyl-thiazol-2-yl)-3-{2-fluoro-4-[7-(2-methyl-pyridin-4-yl)-imidazo[1,2-a]pyridin-3-yl]-phenyl}-urea | 501 (M + 1) |
| 111 | 1-(5-tert-Butyl-thiazol-2-yl)-3-{4-[7-(2-methyl-pyridin-4-yl)-imidazo[1,2-a]pyridin-3-yl]-phenyl}-urea | 483 (M + 1) |
| 112 | 1-(5-tert-Butyl-thiazol-2-yl)-3-(2-fluoro-4-{7-[4-(4-methyl-piperazine-1-carbonyl)-phenyl]-imidazo[1,2-a]pyridin-3-yl}-phenyl)-urea | 612 (M + 1) |
| 113 | 1-(5-tert-Butyl-isoxazol-3-yl)-3-{4-[7-(2-diethylaminomethyl-pyridin-4-yl)-imidazo[1,2-a]pyridin-3-yl]-2-fluoro-phenyl}-urea | 556 (M + 1) |
| 114 | 1-(5-tert-Butyl-thiazol-2-yl)-3-[4-(7-pyridin-4-yl-imidazo[1,2-a]pyridin-3-yl)-2-trifluoromethyl-phenyl]-urea | 537 (M + 1) |
| 115 | 1-(5-tert-Butyl-thiazol-2-yl)-3-{4-[7-(2-methyl-pyridin-4-yl)-imidazo[1,2-a]pyridin-3-yl]-benzyl}-urea | 497 (M + 1) |
| 116 | 1-(5-tert-Butyl-thiazol-2-yl)-3-{4-[7-(2-methyl-pyridin-4-yl)-imidazo[1,2-a]pyridin-3-yl]-2-trifluoromethyl-phenyl}-urea | 551 (M + 1) |
| 117 | 1-(3-tert-Butyl-5-dimethylaminomethyl-phenyl)-3-[2-fluoro-4-(7-pyridin-4-yl-imidazo[1,2-a]pyridin-3-yl)-phenyl]-urea | 537 (M + 1) |

Example 118

1-[5-tert-Butyl-2-(2-hydroxy-ethyl)-2H-pyrazol-3-yl]-3-{4-[7-(4-methanesulfonyl-phenyl)-imidazo[1,2-a]pyridin-3-yl]-benzyl}-urea

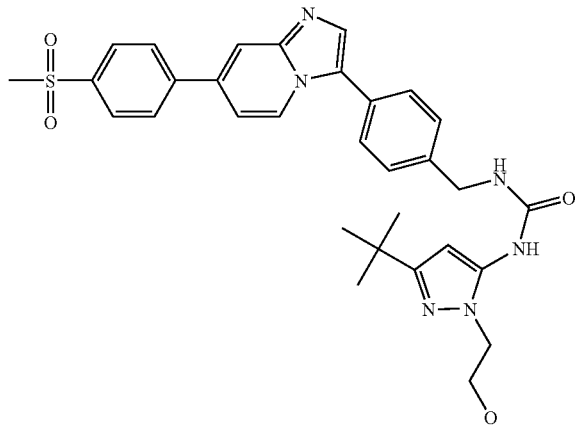

A. 1-{5-tert-Butyl-2-[2-(tert-butyl-dimethyl-silanyloxy)-ethyl]-2H-pyrazol-3-yl}-3-{4-[7-(4-methanesulfonyl-phenyl)-imidazo[1,2-a]pyridin-3-yl]-benzyl}-urea Prepare the title compound in a manner analogous to Example 1 from 4-[7-(4-methanesulfonyl-phenyl)-imidazo[1,2-a]pyridin-3-yl]-benzylamine and {5-tert-butyl-2-[2-(tert-butyl-dimethyl-silanyloxy)-ethyl]-2H-pyrazol-3-yl}-carbamic acid 2,2,2-trichloro-ethyl ester. MS (ES), m/z 701 (M+1).

B. 1-[5-tert-Butyl-2-(2-hydroxy-ethyl)-2H-pyrazol-3-yl]-3-{4-[7-(4-methanesulfonyl-phenyl)-imidazo[1,2-a]pyridin-3-yl]-benzyl}-urea In a round bottomed flask dissolve 1-{5-tert-butyl-2-[2-(tert-butyl-dimethyl-silanyloxy)-ethyl]-2H-pyrazol-3-yl}-3-{4-[7-(4-methanesulfonyl-phenyl)-imidazo[1,2-a]pyridin-3-yl]-benzyl}-urea (0.26 g, 0.37 mmol) in THF (5 mL) under $N_2$. Add TBAF (0.41 mL of a 1M solution in THF, 1.1 equiv.) via syringe and stir the reaction at room temperature for 20 minutes. Load the reaction directly onto a silica column and purify (EtOAc to 5% MeOH: DCM to 10% 2 M $NH_3$ in MeOH: DCM) to give a pale yellow solid (0.168 g, 77%). MS (ES), m/z 587 (M+1).

Example 119

1-[5-tert-Butyl-2-(2-morpholin-4-yl-ethyl)-2H-pyrazol-3-yl]-3-{4-[7-(4-methanesulfonyl-phenyl)-imidazo[1,2-a]pyridin-3-yl]-benzyl}-urea

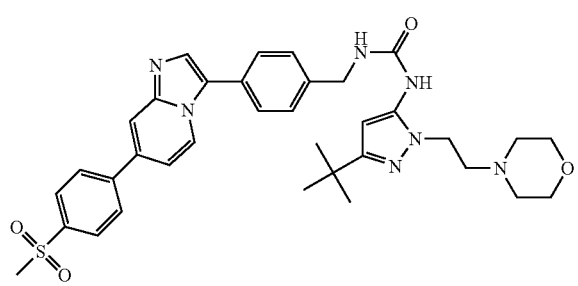

A. Methanesulfonic acid 2-[3-tert-butyl-5-(3-{4-[7-(4-methanesulfonyl-phenyl)-imidazo[1,2-a]pyridin-3-yl]-benzyl}-ureido)-pyrazol-1-yl]-ethyl ester In a round bottomed flask dissolve 1-[5-tert-butyl-2-(2-hydroxy-ethyl)-2H-pyrazol-3-yl]-3-{4-[7-(4-methanesulfonyl-phenyl)-imidazo[1,2-a]pyridin-3-yl]-benzyl}-urea (0.2 g, 0.34 mmol) and triethyl amine (0.48 mL, 10 equiv.) in DCM (20 mL) under $N_2$. Add methanesulfonyl chloride (0.13 mL, 4.8 equiv.) dropwise and stir the reaction at room temperature for 15 minutes. Load the crude reaction directly onto silica gel and purify (EtOAc to 5% MeOH: DCM) to give a yellow solid (0.22 g, 97%). MS (ES), m/z 665 (M+1).

B. 1-[5-tert-Butyl-2-(2-morpholin-4-yl-ethyl)-2H-pyrazol-3-yl]-3-{4-[7-(4-methanesulfonyl-phenyl)-imidazo[1,2-a]pyridin-3-yl]-benzyl}-urea In a round bottomed flask, dissolve methanesulfonic acid 2-[3-tert-butyl-5-(3-{4-[7-(4-methanesulfonyl-phenyl)-imidazo[1,2-a]pyridin-3-yl]-benzyl}-ureido)-pyrazol-1-yl]-ethyl ester (75 mg, 0.11 mmol) in DMF (2 mL). Add morpholine (0.1 mL, 10 eq) and heat the reaction to 70° C. overnight under $N_2$. Dilute the reaction with EtOAc then wash with water, 1 N NaOH, and saturated aqueous saturated sodium chloride. Dry the organics over magnesium sulfate, filter, and concentrate. Purify the compound on a silica gel column (EtOAc to 5% MeOH: DCM to 10% 2 M $NH_3$ in MeOH: DCM) to give a pale yellow solid (46 mg, 62%). MS (ES), m/z 656 (M+1).

Prepare the following according to procedures similar to Example 119:

| Ex. | Compound Name | Physical Data MS (ES), (m/z) |
|---|---|---|
| 120 | 1-[5-tert-Butyl-2-(2-piperidin-1-yl-ethyl)-2H-pyrazol-3-yl]-3-{4-[7-(4-methanesulfonyl-phenyl)-imidazo[1,2-a]pyridin-3-yl]-benzyl}-urea | 654 (M + 1) |

Example 121

1-[4-(7-Pyridin-4-yl-imidazo[1,2-a]pyridin-3-yl)-phenyl]-3-(3-trifluoromethyl-phenyl)-urea

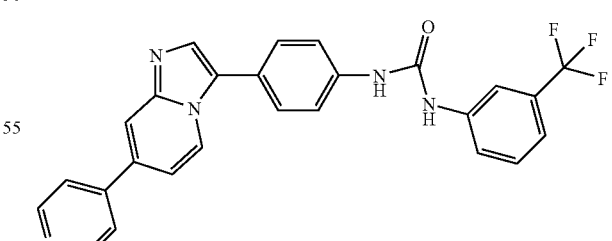

A. 4-{[3-(3-Trifluoromethylphenyl)-ureido]-phenyl}-boronic acid

Charge a 100 mL round bottom flask equipped with a septum, $N_2$ needle, and magnetic stirrer with (4-aminophenyl)boronic acid hydrochloride salt (2.46 g, 14.2 mmol), di-isopropyl ethyl amine (3.6 g, 4.7 mL, 28.4 mmol), CH$_2$Cl$_2$ (dry) (40 mL), DMSO (2 mL). Deoxygenate the reaction with N$_2$ for 4 minutes, and add a solution of 3-trifluoromethylphenyl-isocyanate (15.7 mg, 0.012 mL, 0.084 mmol) in (17 mL) at room temperature. Stir the mixture for 24 hours. Evaporate the mixture under reduced pressure to a tan solid 7.6 g that and use directly in next reaction MS (ES), m/z 324 (M+1).

B. 1-[4-(7-Chloro-imidazo[1,2-a]pyridin-3-yl)-phenyl]-3-(3-trifluoromethyl-phenyl)-urea Charge a 100 mL round bottom flask equipped with: septum, N$_2$ atmosphere, condenser, magnetic stirrer, temperature controlled heating mantle 4-{[3-(3-trifluormethylphenyl)-ureido]-phenyl}-boronic acid (6.10 g, 18.8 mmol), 7-chloro-3-iodo-imidazo[1,2-a]pyridine (5.0 g, 18. mmol), Cs$_2$CO$_3$ (13.19 g, 40.5 mmol), DMF (70 mL), EtOH (12 mL). Deoxygenate the mixture with N$_2$, and add Pd(PPh$_3$)$_4$ (417 mg). Heat the mixture to 70° C. for 18 hours. Pour the reaction into cold water (400 mL) and mix for 15 minutes. Filter the solids off. Dissolve the crude product into CH$_2$Cl$_2$ and chromatograph using SiO$_2$ eluting with a gradient of 0% to 8% of 2 M NH$_3$ in MeOH with the balance CH$_2$Cl$_2$. Slurry the semi-pure product in MeOH/CH$_2$Cl$_2$ and then triturate with a minimal amount of hexane to give a yellow solid. Vacuum oven dry the solid to give the title compound 3.38 g. Additional product (1.0 g) is obtained from concentration of filtrate. MS (ES), m/z 431 (M+1).

C. 1-[4-(7-Pyridin-4-yl-imidazo[1,2-a]pyridin-3-yl)-phenyl]-3-(3-trifluoromethyl-phenyl)-urea Load in a 5 mL septum capped vial the following: small magnetic stir bar, 1-[4-(7-chloro-imidazo[1,2-a]pyridin-3-yl)-phenyl]-3-(3-trifluoromethyl-phenyl)-urea (250 mg, 0.58 mmol), 4-pyridyl boronic acid (77.4 mg, 0.63 mmols, 1.1 Eq), S-phos (236 mg), Pd(OAc)$_2$ (60 mg), K$_3$PO$_4$ (237 mg, 1.12 mmol), 1,4-dioxane: H$_2$O 2:1. Heat the reaction to 50° C. for 24 hours, cool and purify with a Varian SCX® (10 g) column that is pre-washed with water and methanol, and elute the product with 2 N NH$_3$ in methanol. Evaporate the product containing fractions under reduced pressure and take up into CH$_2$Cl$_2$ and chromatograph using SiO$_2$ eluting with a gradient of 0% to 10% of 2 M NH$_3$ in MeOH with the balance CH$_2$Cl$_2$. Evaporate the fractions containing the product under reduced pressure, then vacuum oven dry at 40° C. to give the title compound as a yellow solid 61.8 mg (22.5%). MS (ES), m/z 474 (M+1).

Prepare the following according to procedures similar to Example 121C:

| Ex. | Compound Name | Physical Data MS (ES), (m/z) |
|---|---|---|
| 122 | 1-{4-[7-(4-Dimethylaminomethyl-phenyl)-imidazo[1,2-a]pyridin-3-yl]-phenyl}-3-(3-trifluoromethyl-phenyl)-urea | 530 (M + 1) |
| 123 | 1-{4-[7-(6-Methoxy-pyridin-3-yl)-imidazo[1,2-a]pyridin-3-yl]-phenyl}-3-(3-trifluoromethyl-phenyl)-urea | 504 (M + 1) |

Example 124

1-{4-[7-(6-Methoxy-pyridin-3-yl)-imidazo[1,2-a]pyridin-3-yl]-benzyl}-3-(3-trifluoromethyl-phenyl)-urea

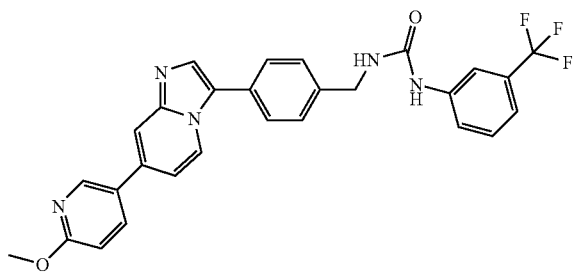

A. 1-[4-(7-Chloro-imidazo[1,2-a]pyridin-3-yl)-benzyl]-3-(3-trifluoromethyl-phenyl)-urea Charge a 50 mL flask equipped with a magnetic stir bar, 4-(7-chloro-imidazo[1,2-a]pyridin-3-yl)-benzylamine (720 mg, 2.79 mmol), di-isopropyl ethyl amine (723 mg, 0.93 mL, 5.6 mmol), and THF (28 mL). Purge the flask with N$_2$, and add 3-trifluoromethylphenyl-isocyanate (1.04 g, 0.77 mL, 5.6 mmol) via syringe. Mix the reaction at room temperature for 24 hours. Evaporate the reaction in vacuo, and chromatograph the residue using SiO$_2$ eluting with a gradient of 1% to 15% of 2 M NH$_3$ in MeOH with the balance CH$_2$Cl$_2$. Evaporate the fractions containing the product under reduced pressure, and vacuum oven dry the resulting ivory solid at 40° C. to give the title compound 624 mg (50.3%). MS(ES), m/z 445.3 (M+1).

B. 1-{4-[7-(6-Methoxy-pyridin-3-yl)-imidazo[1,2-a]pyridin-3-yl]-benzyl}-3-(3-trifluoromethyl-phenyl)-urea Load a 5 mL septum capped vial with the following: small magnetic stir bar, 1-[4-(7-chloro-imidazo[1,2-a]pyridin-3-yl)-benzyl]-3-(3-trifluoromethyl-phenyl)-urea (208 mg, 0.46 mmol), 6-methoxy-pyridin-3-yl boronic acid (0.51 mmols, 1.1 Eq), 2-dicyclohexylphosphino-2',6'-dimethoxy-1,1'-biphenyl (23.6 mg), Pd(OAc)$_2$ (5 mg), K$_3$PO$_4$ (218 mg, 1.03 mmol), dioxane:H$_2$O 2:1 (3 mL). Deoxygenate the reaction with N$_2$ and heat to 40° C. for 24 hours. Cool the mixture and pour into a separatory funnel containing CH$_2$Cl$_2$ (45 mL) and H$_2$O (2 mL). Extract the CH$_2$Cl$_2$ and evaporate under reduced pressure. Mix the residue with CH$_2$Cl$_2$ and a small amount of acetone. Filter the resulting solid and rinse with a small amount of CH$_2$Cl$_2$ and air dry. Vacuum oven dry the solid at 40° C. to give the title compound in 56% yield: MS(ES), m/z 518 (M+1).

Prepare the following according to procedures similar to Example 124B:

| Ex. | Compound Name | Physical Data MS (ES), (m/z) |
|---|---|---|
| 125 | 1-{4-[7-(4-Dimethylaminomethyl-phenyl)-imidazo[1,2-a]pyridin-3-yl]-benzyl}-3-(3-trifluoromethyl-phenyl)-urea | 544 (M + 1) |

Example 126

1-(5-tert-Butyl-2H-pyrazol-3-yl)-3-{4-[7-(4-methanesulfonyl-phenyl)-imidazo[1,2-a]pyridin-3-yl]-phenyl}-urea

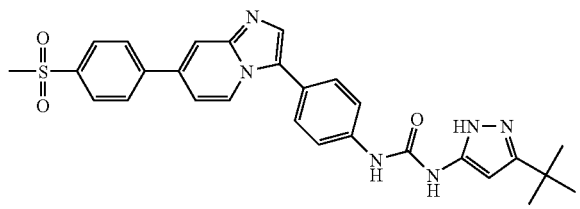

To a round bottomed flask, add 1-(4-bromo-phenyl)-3-(5-tert-butyl-2H-pyrazol-3-yl)-urea (0.41 g, 1.2 mmol), tricyclohexylphosphine (24 mg, 0.07 equiv.), potassium acetate (0.36 g, 3 equiv.), bis(pinacolato)diboron (0.34 g, 1.1 equiv.) and DMSO (5 mL). Deoxygenate this mixture thoroughly with $N_2$ then add tris(dibenzylideneacetone)-di-palladium (0) (33 mg, 0.03 equiv.) and heat to 100° C. overnight. Dilute the reaction with EtOAc and wash with water then saturated aqueous saturated sodium chloride. Pass the organic layer thru a Celite® plug then dry over magnesium sulfate, filter and concentrate to a residue (0.72 g). MS (ES), m/z 385.4 (M+1) is present. Add to this residue 3-iodo-7-(4-methanesulfonyl-phenyl)-imidazo[1,2-a]pyridine (0.25 g, 0.62 mmol), potassium carbonate (0.26 g, 1.86 mmol), dioxane (10 mL), and water (5 mL). Deoxygenate this mixture thoroughly with $N_2$ then add dichloro-bis(triphenylphosphine) palladium (II) (13 mg, 0.03 equiv.) and reflux the reaction overnight under $N_2$. Concentrate the reaction to dryness and slurry in acetone and filter to remove insolubles. Concentrate the filtrate then purify by silica column (1:1 Hex:EtOAc to 1:2 Hex:EtOAc to EtOAc to 5% MeOH:DCM) to give crude product. Triturate from DCM to give a pale yellow solid (0.059 g, 18%). MS (ES), m/z 529 (M+1).

Prepare the following according to procedures similar to Example 126:

| Ex. | Compound Name | Physical Data MS (ES), (m/z) |
|---|---|---|
| 127 | 1-{2-Fluoro-4-[7-(4-methanesulfonyl-phenyl)-imidazo[1,2-a]pyridin-3-yl]-phenyl}-3-(3-trifluoromethyl-phenyl)-urea | 569 (M + 1) |
| 128 | 1-(5-tert-Butyl-isoxazol-3-yl)-3-[2,6-difluoro-4-(7-pyridin-4-yl-imidazo[1,2-a]pyridin-3-yl)-phenyl]-urea | 489 (M + 1) |
| 129 | 1-(5-tert-Butyl-isoxazol-3-yl)-3-{2-fluoro-4-[7-(2-methyl-pyridin-4-yl)-imidazo[1,2-a]pyridin-3-yl]-phenyl}-urea methane sulfonate | 485 (M + 1) |
| 130 | 1-(5-tert-Butyl-isoxazol-3-yl)-3-[2-fluoro-4-(7-pyridin-4-yl-imidazo[1,2-a]pyridin-3-yl)-phenyl]-urea | 471 (M + 1) |
| 131 | 1-(5-tert-Butyl-isoxazol-3-yl)-3-[2-fluoro-4-(7-pyridin-4-yl-imidazo[1,2-a]pyridin-3-yl)-benzyl]-urea | 485 (M + 1) |
| 132 | 1-(5-tert-Butyl-isoxazol-3-yl)-3-{2-fluoro-4-[7-(4-methanesulfonyl-phenyl)-imidazo[1,2-a]pyridin-3-yl]-benzyl}-urea | 562 (M + 1) |
| 133 | 1-(5-tert-Butyl-isoxazol-3-yl)-3-{2-fluoro-4-[7-(4-methanesulfonyl-phenyl)-imidazo[1,2-a]pyridin-3-yl]-phenyl}-urea | 548 (M + 1) |
| 134 | 4-(3-{4-[3-(5-tert-Butyl-isoxazol-3-yl)-ureido]-3-fluoro-phenyl}-imidazo[1,2-a]pyridin-7-yl)-N,N-bis-(2-hydroxy-ethyl)-benzamide | 601 (M + 1) |
| 135 | 1-(5-tert-Butyl-isoxazol-3-yl)-3-[2-fluoro-4-(7-pyridin-3-yl-imidazo[1,2-a]pyridin-3-yl)-phenyl]-urea methane sulfonate | 471 (M + 1) |
| 136 | 1-(5-tert-Butyl-isoxazol-3-yl)-3-[2-fluoro-4-(7-pyridin-2-yl-imidazo[1,2-a]pyridin-3-yl)-phenyl]-urea | 471 (M + 1) |
| 137 | 1-(5-tert-Butyl-isoxazol-3-yl)-3-[3-fluoro-4-(7-pyridin-4-yl-imidazo[1,2-a]pyridin-3-yl)-phenyl]-urea trifluoroacetate | 471 (M + 1) |
| 138 | 1-(5-tert-Butyl-isoxazol-3-yl)-3-{2-fluoro-4-[7-(3-fluoro-pyridin-4-yl)-imidazo[1,2-a]pyridin-3-yl]-phenyl}-urea | 489 (M + 1) |
| 139 | 1-(5-tert-Butyl-isoxazol-3-yl)-3-{2-fluoro-4-[7-(2-isopropyl-pyridin-4-yl)-imidazo[1,2-a]pyridin-3-yl]-phenyl}-urea | 513 (M + 1) |
| 140 | 1-(5-tert-Butyl-isoxazol-3-yl)-3-{4-[7-(2-ethyl-pyridin-4-yl)-imidazo[1,2-a]pyridin-3-yl]-2-fluoro-phenyl}-urea | 499 (M + 1) |
| 141 | 1-(5-tert-Butyl-isoxazol-3-yl)-3-(2-fluoro-4-{7-[2-oxo-1-(3-piperidin-1-yl-propyl)-1,2-dihydro-pyridin-4-yl]-imidazo[1,2-a]pyridin-3-yl}-phenyl)-urea | 612 (M + 1) |
| 142 | 1-(5-tert-Butyl-isothiazol-3-yl)-3-[2-fluoro-4-(7-pyridin-4-yl-imidazo[1,2-a]pyridin-3-yl)-phenyl]-urea | 487 (M + 1) |

Example 143

1-(5-tert-Butyl-isoxazol-3-yl)-3-(4-{7-[2-(3-diethylamino-propyl)-pyridin-4-yl]-imidazo[1,2-a]pyridin-3-yl}-2-fluoro-phenyl)-urea

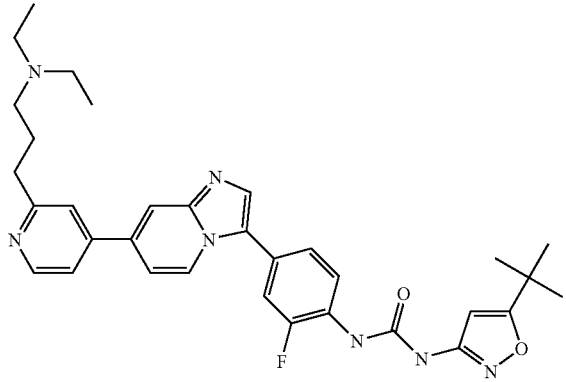

A. 1-(5-tert-Butyl-isoxazol-3-yl)-3-(4-{7-[2-(3,3-diethoxy-propyl)-pyridin-4-yl]-imidazo[1,2-a]pyridin-3-yl}-2-fluoro-phenyl)-urea Prepare according to procedures similar to Example 99. LCMS (ES), m/z 601 (M+1).

B. 1-(5-tert-Butyl-isoxazol-3-yl)-3-(2-fluoro-4-{7-[2-(3-oxo-propyl)-pyridin-4-yl]-imidazo[1,2-a]pyridin-3-yl}-phenyl)-urea hydrochloride Slurry 1-(5-tert-butyl-isoxazol-3-yl)-3-(4-{7-[2-(3,3-diethoxy-propyl)-pyridin-4-yl]-imidazo[1,2-a]pyridin-3-yl}-2-fluoro-phenyl)-urea (1 g, 1.7 mmol) in ethyl acetate (35 mL). Add aqueous 1 N HCl (3.3 mL, 2 equiv.) and stir at room temperature. After 1.5 hours, concentrate to dryness to give an orange solid (0.98 g, 105%). MS (ES), m/z 527 (M+1).

C. 1-(5-tert-Butyl-isoxazol-3-yl)-3-(4-{7-[2-(3-diethylamino-propyl)-pyridin-4-yl]-imidazo[1,2-a]pyridin-3-yl}-2-fluoro-phenyl)-urea Dissolve 1-(5-tert-butyl-isoxazol-3-yl)-3-(2-fluoro-4-{7-[2-(3-oxo-propyl)-pyridin-4-yl]-imidazo[1,2-a]pyridin-3-yl}-phenyl)-urea hydrochloride (0.5 g, 0.89 mmol) in acetic acid (20 mL) under nitrogen. Add diethylamine (0.46 mL, 5 equiv.) and stir overnight at room temperature. In the morning, add sodium triacetoxyborohydride (0.38 g, 2 equiv.) and stir 20 minutes. At this point add excess diethylamine and stir overnight at room temperature. Concentrate to dryness and purify by silica gel (10% Methanol:DCM) to give impure product. Purify by reverse phase (25% MeCN:0.03% HCl in water→100% MeCN). Dilute product containing fractions with ethyl acetate then wash with 1 N NaOH followed by aqueous saturated sodium chloride. Dry the organics over MgSO$_4$, filter and concentrate to give the freebase (0.083 g, 16%) as a yellow solid. LCMS (ES), m/z 584.2 (M+1).

Prepare the following according to procedures similar to Example 143:

| Ex. | Compound Name | Physical Data MS (ES), (m/z) |
|---|---|---|
| 144 | 1-(5-tert-Butyl-isoxazol-3-yl)-3-(2-fluoro-4-{7-[2-(3-morpholin-4-yl-propyl)-pyridin-4-yl]-imidazo[1,2-a]pyridin-3-yl}-phenyl)-urea | 598 (M + 1) |
| 145 | 1-(5-tert-Butyl-isoxazol-3-yl)-3-[2-fluoro-4-(7-{2-[3-(2,2,2-trifluoro-ethylamino)-propyl]-pyridin-4-yl}-imidazo[1,2-a]pyridin-3-yl)-phenyl]-urea | 610 (M + 1) |
| 146 | 1-(5-tert-Butyl-isoxazol-3-yl)-3-[2-fluoro-4-(7-{2-[3-(2-hydroxy-ethylamino)-propyl]-pyridin-4-yl}-imidazo[1,2-a]pyridin-3-yl)-phenyl]-urea | 572 (M + 1) |

Example 147

1-(4-{7-[2-(2-Amino-propyl)-pyridin-4-yl]-Imidazo[1,2-a]pyridin-3-yl}-2-fluoro-phenyl)-3-(5-tert-butyl-isoxazol-3-yl)-urea dihydrochloride

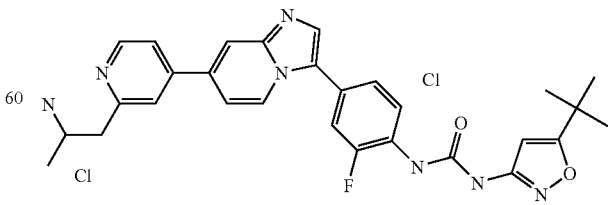

A. {2-[4-(3-{4-[3-(5-tert-Butyl-isoxazol-3-yl)-ureido]-3-fluoro-phenyl}-imidazo[1,2-a]pyridin-7-yl)-pyridin-2-yl]-1-methyl-ethyl}-carbamic acid tert-butyl ester Prepare according to procedures similar to Example 99 from {2-[4-(3-iodo-imidazo[1,2-a]pyridin-7-yl)-pyridin-2-yl]-1-methyl-ethyl}-carbamic acid tert-butyl ester. MS (ES), m/z 628 (M+1).

B. 1-(4-{7-[2-(2-Amino-propyl)-pyridin-4-yl]-imidazo[1,2-a]pyridin-3-yl}-2-fluoro-phenyl)-3-(5-tert-butyl-isoxazol-3-yl)-urea dihydrochloride Prepare according to procedures similar to 108 E. LCMS (ES), m/z 528 (M+1).

Example 148

4-[4-(3-{4-[3-(5-tert-Butyl-isoxazol-3-yl)-ureido]-3-fluoro-phenyl}-imidazo[1,2-a]pyridin-7-yl)-benzoyl]-1-methyl piperazine

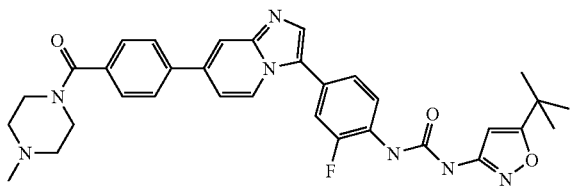

Prepare according to procedures similar to preparation of 4-[4-(3-{4-[3-(5-tert-butyl-isoxazol-3-yl)-ureido]-3-fluoro-phenyl}-imidazo[1,2-a]pyridin-7-yl)-benzoyl]-piperazine-1-carboxylic acid tert-butyl ester. MS(ES), m/z 596 (M+1).

Example 149

1-(4-{7-[6-(4-Methyl-piperazin-1-yl)-pyridin-3-yl]-imidazo[1,2-a]pyridin-3-yl}-benzyl)-3-(3-trifluoromethyl-phenyl)-urea

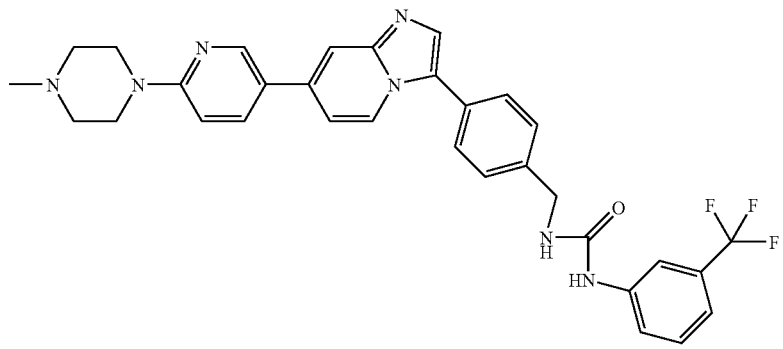

A. (4-{7-[6-(4-Methyl-piperazin-1-yl)-pyridin-3-yl]-imidazo[1,2-a]pyridin-3-yl}-benzyl)-carbamic acid tert-butyl ester Dissolve {4-[7-(6-fluoro-pyridin-3-yl)-imidazo[1,2-a]pyridin-3-yl]-benzyl}-carbamic acid tert-butyl ester (0.500 g, 1.19 mmol, 1.0 eq.) and N-methyl piperazine (0.53 mL, 4.78 mmol, 4.0 eq.) in DMSO (20 mL). Add $K_2CO_3$ (0.330 g, 2.0 eq.). Stir the reaction mixture at 80° C. overnight. Pour the mixture into 20 mL of ice. Filter the solid, and purify by silica gel chromatography with a 0-5% MeOH/DCM gradient to give the title compound 0.408 g (0.82 mmol, 70%) as a slightly yellow solid. Use the solid directly in the reaction B below: MS(ES), m/z 499 (M+1).

B. 1-(4-{7-[6-(4-Methyl-piperazin-1-yl)-pyridin-3-yl]-imidazo[1,2-a]pyridin-3-yl}-benzyl)-3-(3-trifluoromethyl-phenyl)-urea Prepare according to procedures similar to Example 105. MS(ES), m/z 586 (M+1).

Prepare the following according to procedures similar to Example 149:

| Ex. | Compound Name | Physical Data MS (ES), (m/z) |
|---|---|---|
| 150 | 1-{4-[7-(6-Morpholin-4-yl-pyridin-3-yl)-imidazo[1,2-a]pyridin-3-yl]-benzyl}-3-(3-trifluoromethyl-phenyl)-urea | 573 (M + 1) |
| 151 | 1-{4-[7-(6-Dimethylamino-pyridin-3-yl)-imidazo[1,2-a]pyridin-3-yl]-phenyl}-3-(3-trifluoromethyl-phenyl)-urea | 517 (M + 1) |
| 152 | 1-{4-[7-(6-(2-pyrrolidin-1-ylethylamino)-pyridin-3-yl)-imidazo[1,2-a]pyridin-3-yl]-phenyl}-3-(3-trifluoromethyl-phenyl)-urea | 586 (M + 1) |

Example 153

1-(3-tert-Butyl-isoxazol-5-yl)-3-{4-[7-(6-morpholin-4-yl-pyridin-3-yl)-imidazo[1,2-a]pyridin-3-yl]-benzyl}-urea

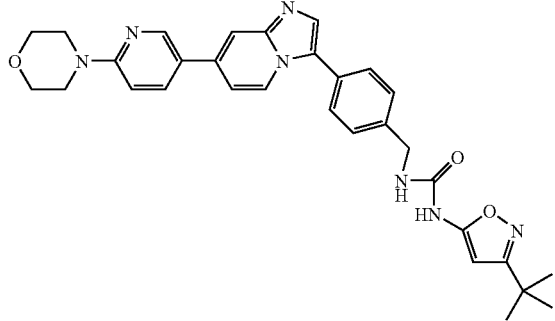

Dissolve 1-{4-[7-(6-morpholin-4-yl-pyridin-3-yl)]-imidazo[1,2-a]pyridin-3-yl]-benzyl}-carbamic acid tert-butyl ester (0.40 g, 0.82 mmol, 1.0 eq.) in DCM/MeOH (2:1, 18 mL). Add HCl (4.0 M in dioxane, 4 mL). Stir the mixture at room temperature overnight. Evaporate under vacuum and dissolve in DMSO (12 mL). Add triethyl amine (0.46 mL, 3.28 mmol, 4 eq.) and (3-tert-butyl-isoxazol-5-yl)-carbamic acid 2,2,2-trichloro-ethyl ester (0.130 g, 0.41 mmol, 1.0 eq.). Stir the reaction mixture at 80° C. overnight under nitrogen. Pour the reaction mixture into 40 mL of ice. Filter off the solid and purify by silica gel chromatography using a 0-5% MeOH/DCM gradient to give the title compound (0.328 g, 72% yield). MS(ES), m/z 552 (M+1)

Prepare the following according to procedures similar to Example 153:

| Ex. | Compound Name | Physical Data MS (ES), (m/z) |
|---|---|---|
| 154 | 1-(5-tert-Butyl-isoxazol-3-yl)-3-{4-[7-(6-morpholin-4-yl-pyridin-3-yl)-imidazo[1,2-a]pyridin-3-yl]-benzyl}-urea | 552 (M + 1) |

Example 155

1-{4-[7-(6-Methylamino-pyridin-3-yl)-imidazo[1,2-a]pyridin-3-yl]-benzyl}-3-(3-trifluoromethyl-phenyl)-urea

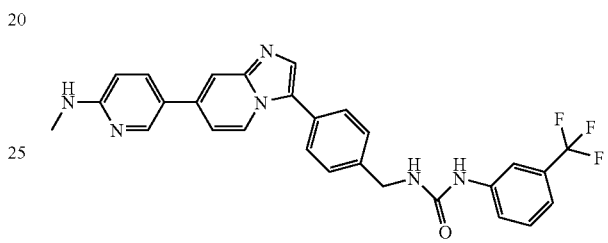

Dissolve 1-{4-[7-(6-Morpholin-4-yl-pyridin-3-yl)-imidazo[1,2-a]pyridin-3-yl]-benzyl}-3-(3-trifluoromethyl-phenyl)-urea (0.220 g, 0.435 mmol, 1.0 eq.) in DMSO (2 mL). Add $K_2CO_3$ (0.120 g, 0.870 mmol, 2.0 eq.). Add piperazine (0.150 g, 1.74 mmol, 4.0 eq.). Stir the reaction mixture at 80° C. overnight under nitrogen. Pour the reaction mixture into 40 mL of ice and filter. Purify the yellow solid by silica gel chromatography using a 0-5% MeOH/DCM gradient to give the title compound 0.170 g (0.33 mmol, 76%) as a slightly yellow solid: MS(ES), m/z 518 (M+1).

Example 156

1-(5-tert-Butyl-isoxazol-3-yl)-3-{4-[7-(6-methoxy-pyridin-3-yl)-imidazo[1,2-a]pyridin-3-yl]-benzyl}-urea

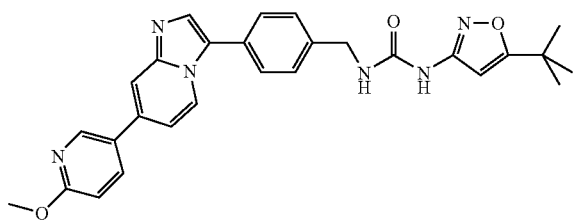

Dissolve {4-[7-(6-fluoro-pyridin-3-yl)-imidazo[1,2-a]pyridin-3-yl]-benzyl}-carbamic acid tert-butyl ester (0.990 g, 2.37 mmol, 1.0 eq.) in DCM/MeOH (3:1, 120 mL). Add HCl (4.0 M in dioxane 14 mL). Stir the mixture at room temperature overnight. Evaporate the mixture under vacuum, and dissolve the residue in MeOH/dioxane (1:2, 90 mL) and triethyl amine (2 mL, 14.22 mmol, 6 eq). Add 5-tert-butyl-isoxazol-3-yl)-carbamic acid 2,2,2-trichloro-ethyl ester, and stir the reaction mixture at 80° C. overnight under nitrogen. Purify the reaction mixture by silica gel chromatography using a 0-5% MeOH/DCM gradient to give the title compound 0.708 g (1.43 mmol, 60%) as a slightly yellow solid: MS(ES), m/z 497 (M+1).

Example 157

1-(5-tert-Butyl-isoxazol-3-yl)-3-{4-[7-(6-oxo-1,6-dihydro-pyridin-3-yl)-imidazo[1,2-a]pyridin-3-yl]-benzyl}-urea

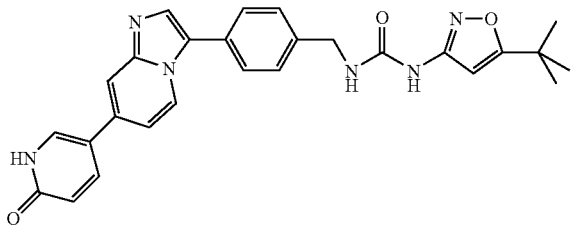

Dissolve 1-(5-tert-butyl-isoxazol-3-yl)-3-{4-[7-(6-methoxy-pyridin-3-yl)-imidazo[1,2-a]pyridin-3-yl]-benzyl}-urea (0.408 g, 0.82 mmol, 1.0 eq.) in HBr (~48%, 4 mL) and stir at 80° C. overnight under nitrogen. Evaporate the reaction mixture under vacuum and purify in four steps: 1) flash SCX, 2) reverse phase HPLC The mixture is purified via reversed phase C18 column HPLC employing a gradient of 5 to 65% acetonitrile vs 0.03% aqueous HCl, 3) flash SCX, and 4) silica gel chromatography using a 0-10% MeOH/DC gradient to give the title compound 0.156 g as a white solid: MS(ES), m/z 483 (M+1).

Example 158

1-{4-[7-(6-Oxo-1,6-dihydro-pyridin-3-yl)-imidazo[1,2-a]pyridin-3-yl]-benzyl}-3-(3-trifluoromethyl-phenyl)-urea

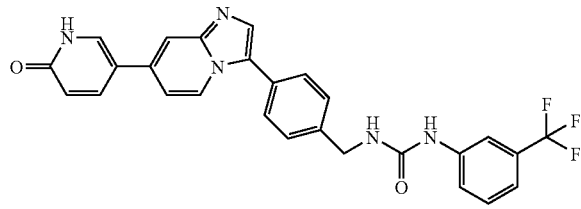

Prepare 1-{4-[7-(6-oxo-1,6-dihydro-pyridin-3-yl)-imidazo[1,2-a]pyridin-3-yl]-benzyl}-3-(3-trifluoromethyl-phenyl)-urea from 1-{4-[7-(6-fluoro-pyridin-3-yl)-imidazo[1,2-a]pyridin-3-yl]-benzyl}-3-(3-trifluoromethyl-phenyl)-urea according to a sequence of steps consisting of the same procedures used to prepare 1-(5-tert-butyl-isoxazol-3-yl)-3-{4-[7-(6-oxo-1,6-dihydro-pyridin-3-yl)-imidazo[1,2-a]pyridin-3-yl]-benzyl}-urea. MS (ES), m/z 504 (M+1).

Example 159

1-(5-tert-Butyl-isoxazol-3-yl)-3-{4-[7-(6-dimethylaminomethyl-pyridin-3-yl)-imidazo[1,2-a]pyridin-3-yl]-phenyl}-urea

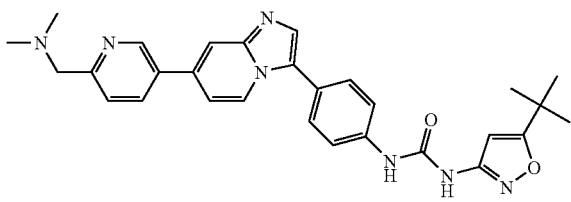

A. (5-Bromo-pyridin-2-ylmethyl)-dimethyl-amine

Place 5-bromo-2-bromomethyl-pyridine (1.7 g, 6.7 mmol, 1 eq) (*Bioorg. Med. Chem. Lett.* 1994, 4(1), 99) in a 250 mL round bottom short neck flask, dissolve in 100 mL of THF, cool to 0° C. and treat with a 2 M N,N-dimethylamine solution in THF (9 mL, 18 mmol, 2.7 eq). After 2 hours, concentrate the reaction, dilute with 50 mL of $CH_2Cl_2$, and wash with 20 mL of water. Dry the organics and concentrate to give 0.90 g (64%) of the title compound as a brown oil. MS (ES), m/z 217 (M+1).

B. 1-(5-tert-Butyl-isoxazol-3-yl)-3-{4-[7-(6-dimethylaminomethyl-pyridin-3-yl)-imidazo[1,2-a]pyridin-3-yl]-phenyl}-urea In a 100 mL round bottom short neck flask, stir a suspension of 4-(7-chloro-imidazo[1,2-a]pyridin-3-yl)-phenylamine (1 g, 4.1 mmol, 1 eq) in 30 mL of 1,4-dioxane with bis(pinacolato)diboron (1.56 g, 6.15 mmol, 1.5 eq), potassium acetate (1.2 g, 12 mmol, 3 eq) and 2-biphenyl-biscyclohexylphosphine (0.29 g. 0.82 mmol, 0.20 eq). Deoxygenate the resulting slurry with two cycles of evacuation and bubbling nitrogen through the slurry for 10 minutes each. Fit the flask with a reflux condenser, add palladium acetate (0.046 g, 0.21 mmol, 0.05 eq), and stir the mixture under nitrogen at 80° C. overnight. Filter the hot mixture over a 1 cm pad of Celite®, wash with 50 mL methanol, and concentrate the combined filtrate and wash to give an intermediate boronate ester as a brown pasty solid. Dissolve the solid in 60 mL of 1,4-dioxane/water (1:1) and treat with (5-bromo-pyridin-2-ylmethyl)-dimethyl-amine (0.90 g, 3.6 mmol), tetrakis(triphenyl-phosphine)palladium(0) (0.21 g, 0.18 mmol) and sodium carbonate (1.1 g, 0.011 mmol). Deoxygenate the resulting slurry with two cycles of evacuation and bubbling nitrogen through the slurry for 10 minutes each. Fit the flask with a reflux condenser and stir the mixture under nitrogen at 80° C. overnight. Cool the reaction to room temperature and bring to pH 5 with 1 N HCl. Apply the mixture to a 25 g SCX Mega Bond-Elut™ SCX cartridge (Varian) pre-washed with 200 mL 1:1 $CH_2Cl_2$:MeOH. After loading with vacuum assist, wash the cartridge with 300 mL 1:1 $CH_2Cl_2$:MeOH, then elute with 160 mL 2 M $NH_3$-MeOH. Concentrate the basic eluate in vacuo, and dissolve the intermediate phenylamine in 30 mL of DMSO. Add triethylamine (0.50 g, 4.9 mmol) and (5-tert-butyl-isoxazol-3-yl)-carbamic acid 2,2,2-trichloro-ethyl ester (1.3 g, 4.1 mmol), deoxygenate the mixture with $N_2$ for 5 min, and heat at 70° C. overnight. Cool the reaction to room temperature and bring to pH 5 with 1 N HCl. Apply the mixture to a 25 g SCX Mega Bond-Elut™cartridge (Varian) pre-washed with 200 mL 1:1 $CH_2Cl_2$:MeOH. After loading with vacuum assist, wash the cartridge with 300 mL 1:1 $CH_2Cl_2$:MeOH, then elute with 160 mL 2 M $NH_3$-MeOH. Concentrate the basic eluate in vacuo. Purify the resulting brown oil via reverse phase chromatography using a 25 cm by 50.8 mm (i.d.) column w/10 micron particles. Elute with MeCN/0.03% HCl $H_2O$ (5:95) to 65:35 over 30 minutes gives 0.35 g of the title compound (17% overall). MS (ES), m/z 510 (M+1).

Example 160

(3-Trifluoromethyl-phenyl)-carbamic acid, 4-[7-(4-methanesulfonyl-phenyl)-imidazo[1,2-a]pyridin-3-yl]-benzyl ester

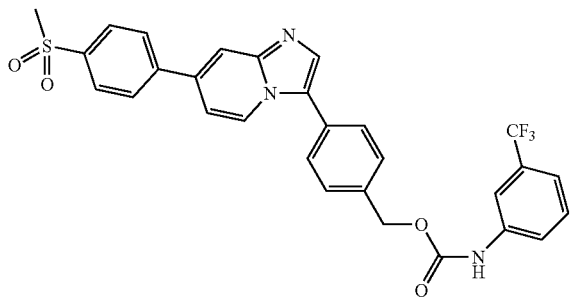

A. [4-(7-Chloro-imidazo[1,2-a]pyridin-3-yl)-phenyl]-methanol

Charge a 50 mL round bottom flask equipped with: a magnetic stirrer, temperature controlled heating mantle, $N_2$ atmosphere, condenser, with 7-chloro-3-iodo-imidazo[1,2-a]pyridine (1.0 g, 3.6 mmol), 4-(hydroxymethyl)phenyl boronic acid (570 mg, 3.75 mmol), 2 M $K_2CO_3$ (7 mL), dimethoxy ethane DME (25 mL). Deoxygenate with a nitrogen purge and add Pd(TPP)$_4$ (200 mg, 0.17 mmol 5 mol %) and heat the reaction to 65° C. for 48 hours. Cool the reaction and siphon off the lower aqueous phase (5 mL). Evaporate the reaction under vacuum at 42° C. to remove DME. Take up the residue in $CH_2Cl_2$ and wash with water (15 mL). Concentrate the $CH_2Cl_2$ and chromatograph giving an oil that solidified on standing to an ivory solid 670 mg (72%) MS (ES), m/z 259.1 (M+1).

B. {4-[7-(4-Methanesulfonyl-phenyl)-imidazo[1,2-a]pyridin-3-yl]-phenyl}-methanol Charge a 100 mL round bottom flask equipped with: a magnetic stirrer, temperature controlled heating mantle, $N_2$ atmosphere, condenser, with [4-(7-chloro-imidazo[1,2-a]pyridin-3-yl)-phenyl]-methanol (1.11 g, 4.3 mmol), 4-(methylsulfonyl)-phenyl boronic acid (1.27 g, 6.4 mmol), 2-Dicyclohexyl-phosphino-2',6'-dimethoxy-1,1'-biphenyl (236 mg), Pd(OAc)$_2$ (60 mg), $K_3PO_4$ (3.6 g, 16.9 mmol), dioxane: $H_2O$ 2:1 (50 mL), EtOH-(3A) (5 mL). Warm the reaction while purging with a $N_2$ needle, then heat to 65° C. for 18 hours. Cool the reaction to room temperature and siphon off the bottom layer (8 mL). Evaporate the reaction under vacuum and dissolve the residue into warm MeOH and filter to remove Pd (0) solids. Rinse the solids with warm MeOH and combine all the MeOHd. (total of 1 L). Evaporate the dissolved crude product under vacuum with 20 g of $SiO_2$ to dryness then chromatograph using $SiO_2$ eluting with a gradient of 0% to 10% of 2 M $NH_3$ in MeOH with the balance $CH_2Cl_2$. Dry the product in a vacuum oven at 40° C. for 24 hours to give a yellow solid 1.64 g (100. %) suspect trapped solvent. MS (ES), m/z 379 (M+1).

C. (3-Trifluoromethyl-phenyl)-carbamic acid 4-[7-(4-methanesulfonyl-phenyl)-imidazo[1,2-a]pyridin-3-yl]-benzyl ester In a ice bath cooled 12 mL septum capped vial purged with $N_2$ add {4-[7-(4-methanesulfonyl-phenyl)-imidazo[1,2-a]pyridin-3-yl]-phenyl}-methanol (32 mg, 0.084 mmol) in $CH_2Cl_2$ (4 mL). Charge the vial with (ααα)-trifluoro-m-tolyl-isocyanate (15.7 mg, 0.012 mL, 0.084 mmol). Remove the reaction from the ice bath and mix at room temperature. Give the reaction a second charge of (ααα)-trifluoro-m-tolyl-isocyanate (15.7 mg, 0.012 mL, 0.084 mmol) and heat to 35° C. for 6 hours. Chromatograph the crude reaction using $SiO_2$ eluting with a gradient of 0% to 8% of 2 M $NH_3$ in MeOH with the balance $CH_2Cl_2$. Dry the product in a vacuum oven at 40° C. for 24 hours to give the title compound 23.5 mg (49%). MS (ES), m/z 566 (M+1).

Example 161

1-[5-(7-Pyridin-4-yl-imidazo[1,2-a]pyridin-3-yl)-pyridin-2-yl]-3-(m-trifluoromethyl-phenyl)-urea

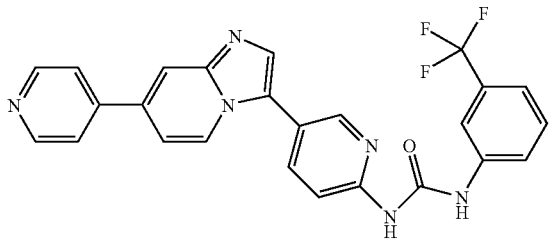

A. 1-(5-Bromopyridin-2-yl)-3-(m-trifluoromethylphenyl)-urea

To a solution of 5-bromopyridin-2-yl amine (1.190 g, 6.88 mmol, 1.0 eq.) in THF (20 mL), add 3-trifluoromethylphenyl isocyanate (0.96 mL, 6.88 mmol, 1.0 eq.) in a drop-wise manner at room temperature. Stir the reaction mixture at room temperature for 30 minutes. Filter the solid and wash with MeOH (2×10 mL). Dry the solid to afford 1.81 g (5.0 mmol, 73%) of the title compound. MS (ES), m/z 360, 362 (M+1).

B. 1-[5-(7-Pyridin-4-yl-imidazo[1,2-a]pyridin-3-yl)-pyridin-2-yl]-3-(m-trifluoromethyl-phenyl)-urea To a solution of 1-(5-bromopyridin-2-yl)-3-(m-trifluoromethylphenyl)-urea (0.520 g, 1.44 mmol, 1.0 eq.) in dioxane (12 mL), add bis(pinacolato)diboron (0.410 g, 1.59 mmol, 1.1 eq.), tricyclohexylphosphine (0.048 g, 12 mol %), potassium acetate (0.211 g, 1.5 eq.), and tris(dibenzylidineacetone)dipalladium (0) (0.066 g, 5 mmol %). Deoxygenate the reaction mixture and stir under nitrogen at 80° C. for approximately 16 h and cool to room temperature. Add 3-iodo-7-pyridin-4-yl-imidazo[1,2-a]pyridine (0.460 g, 1.44 mmol, 1.0 eq.), sodium carbonate solution (2 M, 3 mL) and tetralis(triphenylphosphine)palladium (0) (0.083 g, 5 mmol %). Deoxygenate the reaction mixture and stir at 80° C. for 6 hours, cool, then purify on a SCX cartridge (Varian) as in Example 115. Concentrate SCX-eluted materials and purify via silica gel flash chromatography employing a 0-4% gradient of methanol in dichloromethane to afford 0.450 g (0.99 mmol, 69%) of the title compound. MS (ES), m/z 475 (M+1).

Prepare the following according to procedures similar to Example 161:

| Ex. | Compound Name | Physical Data MS (ES) (m/z) |
|---|---|---|
| 162 | 1-[5-(7-Thiazol-2-yl-imidazo[1,2-a]pyridin-3-yl)-pyridin-2-yl]-3-(m-trifluoromethyl-phenyl)-urea | 481 (M + 1) |
| 163 | 1-(5-tert-butyl-isoxazol-3-yl)-3-[5-(7-pyridin-4-yl-imidazo[1,2-a]pyridin-3-yl)-pyridin-2-yl]-urea | 454 (M + 1) |
| 164 | 1-(5-tert-butyl-isoxazol-3-yl)-3-[5-(7-thiazol-2-yl-imidazo[1,2-a]pyridin-3-yl)-pyridin-2-yl]-urea | 460 (M + 1) |

Example 165

1-(4-{7-[2-(4-Methyl-piperazin-1-yl)-pyrimidin-5-yl]-imidazo[1,2-a]pyridin-3-yl}-phenyl)-3-(3-trifluoromethyl-phenyl)-urea

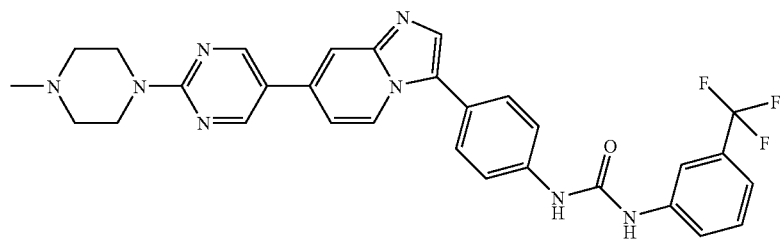

A. 3-(4-Nitro-phenyl)-7-(4,4,5,5-tetramethyl-[1,3,2]dioxaborolan-2-yl)-imidazo[1,2-a]pyridine Combine 7-chloro-3-(4-nitro-phenyl)-imidazo[1,2-a]pyridine (0.417 g, 1.52 mmol), bis(pinacolato)diboron (0.426 g, 1.68 mmol), tricyclohexylphosphine (0.051 g, 0.183 mmol) and potassium acetate (0.224 g, 2.29 mmol) in 1,4-dioxane (20 mL). Bubble nitrogen through the mixture for five minutes. Add tris(dibenzylideneacetone) dipalladium(0) (0.070 g, 0.076 mmol). Heat the mixture to 80° C., stir overnight (15 hr), and cool to room temperature. Filter the mixture through Celite® 521, and concentrate the resulting solution to an orange oil, which is used as is (crude). MS(ES), m/z 366 (M+1).

B. 7-[2-(4-Methyl-piperazin-1-yl)-pyrimidin-5-yl]-3-(4-nitro-phenyl)-imidazo[1,2-a]pyridine Combine 3-(4-nitro-phenyl)-7-(4,4,5,5-tetramethyl-[1,3,2]dioxaborolan-2-yl)-imidazo[1,2-a]pyridine (0.556 g, 1.52 mmol), 5-bromo-2-(4-methyl-piperazin-1-yl)-pyrimidine, HCl (0.447 g, 1.52 mmol) and potassium carbonate (0.842 g, 6.09 mmol) in 1,4-dioxane (20 mL) and water (10 mL). Bubble nitrogen through the mixture for five minutes. Add dichlorobis(triphenylphosphine) palladium(II) (0.032 g, 0.046 mmol). Attach a reflux condenser, and heat the mixture to 110° C., stir overnight (15 hours), and cool to room temperature. Concentrate the mixture to dryness in vacuo. Slurry the resulting solid into dichloromethane/methanol and filter through Celite® 521. Concentrate the solution in vacuo. Purify by column chromatography (ethyl acetate→10% methanol in dichloromethane) to afford product (0.372 g, 59%, two steps). MS(ES), m/z 416 (M+1).

C. 1-(4-{7-[2-(4-Methyl-piperazin-1-yl)-pyrimidin-5-yl]-imidazo[1,2-a]pyridin-3-yl}-phenyl)-3-(3-trifluoromethyl-phenyl)-urea Combine 7-[2-(4-Methyl-piperazin-1-yl)-pyrimidin-5-yl]-3-(4-nitro-phenyl)-imidazo[1,2-a]pyridine (0.318 g, 0.765 mmol), iron(III) chloride (0.006 g, 0.038 mmol), and 1,1-dimethylhydrazine (0.58 mL, 7.65 mmol) in methanol (10 mL). Attach a reflux condenser, and heat the mixture to 70° C., stir overnight (15 hours), and cool to room temperature. Slurry the mixture into additional methanol and filter through Celite® 521. Concentrate the solution in vacuo. Purify by column chromatography (ethyl acetate→5% methanol in dichloromethane→8% methanol in dichloromethane→10% methanol in dichloromethane) to afford a yellow solid intermediate amine, 4-{7-[2-(4-methyl-piperazin-1-yl)-pyrimidin-5-yl]-imidazo[1,2-a]pyridin-3-yl}-phenylamine. Use as is. MS(ES), m/z 386 (M+1).

Combine the amine (0.164 g, 0.425 mmol), 3-trifluoromethylphenyl isocyanate (0.060 mL, 0.425 mmol) and triethylamine (0.119 mL, 0.851 mmol) in DMSO (5 mL). Stir the mixture at room temperature for ninety minutes. Extract the mixture with ethyl acetate versus water. Wash the organic layer with saturated aqueous saturated sodium chloride. Dry the resulting organics over magnesium sulfate, filter, and concentrate. Purify by column chromatography (ethyl acetate→5% methanol in dichloromethane→10% methanol in dichloromethane) to afford product (0.056 g, 13%, two steps). MS(ES), m/z 573 (M+1).

Example 166

1-(5-tert-Butyl-isoxazol-3-yl)-3-(4-{7-[2-(4-methyl-piperazin-1-yl)-pyrimidin-5-yl]-imidazo[1,2-a]pyridin-3-yl}-phenyl)-urea

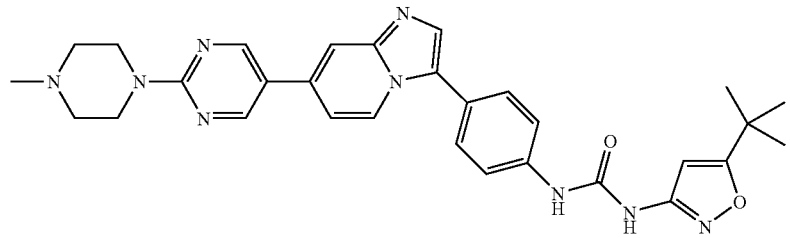

A. 7-[2-(4-Methyl-piperazin-1-yl)-pyrimidin-5-yl]-3-(4-nitro-phenyl)-imidazo[1,2-a]pyridine Combine 3-(4-nitro-phenyl)-7-(4,4,5,5-tetramethyl-[1,3,2]dioxaborolan-2-yl)-imidazo[1,2-a]pyridine (0.556 g, 1.52 mmol), 5-bromo-2-(4-methyl-piperazin-1-yl)-pyrimidine, HCl (0.447 g, 1.52 mmol) and potassium carbonate (0.842 g, 6.09 mmol) in 1,4-dioxane (20 mL) and water (10 mL). Bubble nitrogen through the mixture for five minutes. Add dichlorobis(triphenylphosphine) palladium(II) (0.0.32 g, 0.046 mmol). Attach a reflux condenser, and heat the mixture to 110° C., stir overnight (15 hours), and cool to room temperature. Concentrate the mixture to dryness in vacuo. Slurry the resulting solid into dichloromethane/methanol and filter through Celite® 521. Concentrate the solution in vacuo. Purify by column chromatography (ethyl acetate→10% methanol in dichloromethane) to afford product (0.372 g, 59%, two steps). MS(ES), m/z 416 (M+1).

B. 1-(5-tert-Butyl-isoxazol-3-yl)-3-(4-{7-[2-(4-methyl-piperazin-1-yl)-pyrimidin-5-yl]-imidazo[1,2-a]pyridin-3-yl}-phenyl)-urea Combine 7-[2-(4-methyl-piperazin-1-yl)-pyrimidin-5-yl]-3-(4-nitro-phenyl)-imidazo[1,2-a]pyridine (0.372 g, 0.895 mmol), iron(III) chloride (0.007 g, 0.045 mmol), and 1,1-dimethylhydrazine (0.68 mL, 8.95 mmol) in methanol (10 mL). Attach a reflux condenser, and heat the mixture to 70° C., stir overnight (15 hours), and cool to room temperature. Slurry the mixture into additional methanol and filter through Celite® 521. Concentrate the solution in vacuo to afford yellow solid intermediate amine, 4-{7-[2-(4-methyl-piperazin-1-yl)-pyrimidin-5-yl]-imidazo[1,2-a]pyridin-3-yl}-phenylamine. Use as is. MS(ES), m/z 386 (M+1)

Combine the amine (0.323 g, 0.838 mmol), (5-tert-butyl-isoxazol-3-yl)-carbamic acid 2,2,2-trichloro-ethyl ester (0.291 g, 0.922 mmol) and triethylamine (0.128 mL, 0.922 mmol) in DMSO (10 mL). Heat the mixture to 70° C., stir overnight, and cool to room temperature. Extract the mixture with ethyl acetate versus water. Wash the organic layer with saturated aqueous saturated sodium chloride. Dry the resulting organics over magnesium sulfate, filter, and concentrate. Purify by column chromatography (ethyl acetate→10% methanol in dichloromethane→10% 2 M NH₃ in MeOH in dichloromethane) to afford product (0.057 g, 11%, two steps). MS(ES), m/z 552 (M+1).

Example 167

N-(5-Methyl-thiazol-2-yl)-2-[4-(7-pyridin-4-yl-imidazo[1,2a]pyridine-3-yl)-phenyl]-acetamide

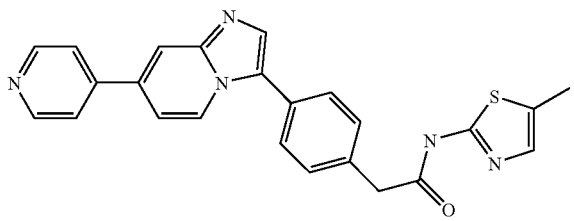

A. [4-(7-Pyridin-4-yl-imidazo[1,2a]pyridine-3-yl)-phenyl]-acetic acid tert-butyl ester Prepare using methods of example 219 (below) using 4-bromo-phenylacetic acid, tert-butyl ester and 7-pyridin-4-yl-imidazo[1,2a]pyridine as coupling partners. Purify the mixture with an SCX column using 1:1 CH₂Cl₂:MeOH/1:1 CH₂Cl₂:2N NH₃-MeOH. Concentrate the eluate to give a crusty yellow-orange solid and purify this solid on a 120 g silica cartridge with 100% CH₂Cl₂ for 5 minutes, followed by a gradient of 0→5% MeOH in CH₂Cl₂ over 35 minutes. Pool and concentrate appropriate fractions to afford the title compound as a yellow solid. MS (ES) m/z 386 (M+1).

B. [4-(7-Pyridin-4-yl-imidazo[1,2a]pyridine-3-yl)-phenyl]-acetic acid

Suspend [4-(7-pyridin-4-yl-imidazo[1,2a]pyridine-3-yl)-phenyl]-acetic acid tert-butyl ester (370 mg, 0.96 mmol) in 10 mL of 4 N HCl/dioxane solution, add 1 mL water and stir the resulting clear yellow solution overnight at room temperature. Concentrate to dryness, dissolve in CH₂Cl₂:MeOH and purify on 10 g SCX cartridge by loading and washing with 1:1 CH₂Cl₂:MeOH. Elute the free base with 1:1 CH₂Cl₂:2 N NH₃-MeOH and concentrate to dryness. LCMS (ES) m/z 330 (M+1).

C. N-(5-Methyl-thiazol-2-yl)-2-[4-(7-pyridin-4-yl-imidazo[1,2a]pyridine-3-yl)-phenyl]-acetamide Add [4-(7-pyridin-4-yl-imidazo[1,2a]pyridine-3-yl)-phenyl]-acetic acid (130 mg, 0.39 mmol) to 5 mL THF and 3 mL DMSO, warm briefly to 70° C., then cool to room temperature to give a slightly turbid yellow solution. Add 4-methyl morpholine (48 mg, 52 µL, 0.47 mmol, 1.2 eq), 2-amino-5-methyl thiazole (54 mg, 0.47 mmol, 1.2 eq) and stir for 10 minutes at room temperature. To this mixture, add DMTMM (131 mg, 0.47 mmol, 1.2 eq) and stir the heavy slurry at room temperature. Dilute the resulting orange solution with 30 mL water, filter off and retain the flocculent solids. Dissolve the solid in CH$_2$Cl$_2$ and minimal MeOH, purify on a 40 g silica cartridge 5 minutes at 100% CH$_2$Cl$_2$ followed by a gradient of 0→5% MeOH in CH$_2$Cl$_2$ over 35 minutes. Pool, concentrate and dry appropriate fractions to provide 75 mg of the title compound as a fluffy yellow powder. LCMS (ES) m/z 426 (M+1).

Example 168

2-[2-Fluoro-4-(7-pyridin-2-yl-imidazo[1,2-a]pyridin-3-yl)-phenyl]-N-[3-(piperazine-1-carbonyl)-5-trifluoromethyl-phenyl]-acetamide

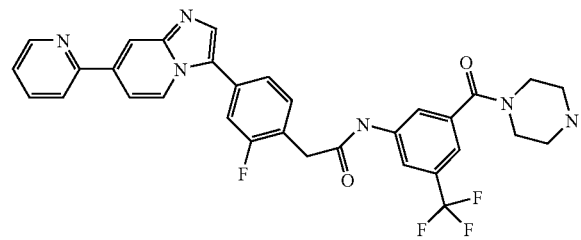

A. 4-(3-{2-[2-Fluoro-4-(7-pyridin-2-yl-imidazo[1,2-a]pyridin-3-yl)-phenyl]-acetylamino}-5-trifluoromethyl-benzoyl)-piperazine-1-carboxylic acid tert-butyl ester Prepare according to procedures similar to example 219 (below). MS (ES), m/z 703 (M+1).

B. 2-[2-Fluoro-4-(7-pyridin-2-yl-imidazo[1,2-a]pyridin-3-yl)-phenyl]-N-[3-(piperazine-1-carbonyl)-5-trifluoromethyl-phenyl]-acetamide Dissolve 4-(3-{2-[2-fluoro-4-(7-pyridin-2-yl-imidazo[1,2-a]pyridin-3-yl)-phenyl]-acetylamino}-5-trifluoromethyl-benzoyl)-piperazine-1-carboxylic acid tert-butyl ester (0.76 g, 0.108 mmol) in 1:1 CH$_2$Cl$_2$ MeOH (20 mL) and add 2M HCl in THF (2 mL), then stir 2 hours and concentrate in vacuo. Load onto a Varian MegaElut® SCX cartridge (10 gram cartridge prewashed with methanol), rinse with methanol to remove impurities then elute crude product with 2 M NH$_3$ in methanol. Concentrate this solution in vacuo then purify by silica gel chromatography (0%→10% 2 M NH$_3$ Methanol:DCM) to give a yellow residue (0.400 g, 49% over 2 steps). MS (ES), m/z 603 (M+1).

Example 169

4-[4-(7-Pyridin-4-yl-imidazo[1,2-a]pyridin-3-yl)-phenyl]-N-(3-trifluoromethyl-phenyl)-butyramide

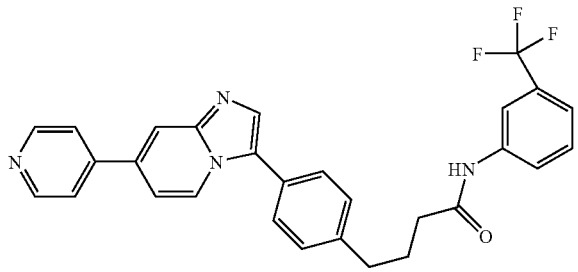

Combine 4-[4-(7-Chloro-imidazo[1,2-a]pyridin-3-yl)-phenyl]-N-(3-trifluoromethyl-phenyl)-butyramide (0.15 g, 0.32 mmol), 4-pyridine boronic acid (0.04 g, 0.35 mmol), S-Phos (0.02 g, 0.04 mmol) and K$_3$PO$_4$ (0.13 g, 0.63 mmol) with dioxane (3.5 mL) and water (1.5 mL) and stir at room temperature while the reaction contents are de-gassed with nitrogen for 5 minutes. Add palladium diacetate (0.01 g, 0.04 mmol). Heat to 100-105° C. for 20 hours. Cool and dilute with water (10 mL) and dichloromethane. The organic layer are then filtered onto a pre-equilibrated in methanol Varian SCX column (10 g), washed with 30 mL each of water, methanol, dichloromethane and methanol. Elute crude product with 2N methanolic ammonia (50 mL). Concentrate the ammonia solution in vacuo to dryness to yield a residue that is chromatographed on silica (0→3% methanol in ethyl acetate over 30 min) to yield 4-[4-(7-Pyridin-4-yl-imidazo[1,2-a]pyridin-3-yl)-phenyl]-N-(3-trifluoromethyl-phenyl)-butyramide (0.10 g, 0.19 mmol). MS(ESI), m/z 501 (M+1).

Prepare the following according to procedures similar to Example 169:

| Ex. | Compound Name | Physical Data MS (ES), (m/z) |
|---|---|---|
| 170 | 2-{4-[7-(2-Fluoro-pyridin-4-yl)-imidazo[1,2-a]pyridin-3-yl]-phenyl}-N-(3-trifluoromethyl-phenyl)-acetamide | 491 (M + 1) |
| 171 | N-(5-tert-Butyl-isoxazol-3-yl)-2-{4-[7-(2-fluoro-pyridin-4-yl)-imidazo[1,2-a]pyridin-3-yl]-phenyl}-acetamide | 471 (M + 1) |

Example 172

N-(4-Cyano-3-trifluoromethyl-phenyl)-2-[4-(7-pyridin-4-yl-imidazo[1,2a]pyridine-3-yl)-phenyl]-acetamide

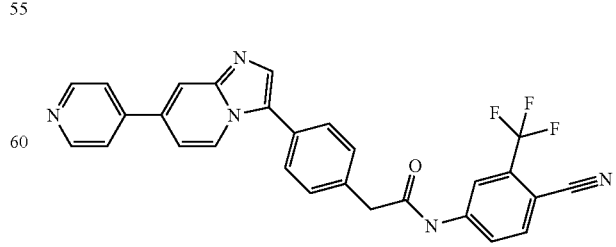

Suspend 3-iodo-7-pyridin-4-yl-imidazo[1,2-a]pyridine (321 mg, 1 mmol), N-(4-Cyano-3-trifluoromethyl-phenyl)-

2-[4-(4,4,5,5-tetramethyl-[1,3,2]dioxaborolan-2-yl)-phenyl]-acetamide (473 mg, 1.1 mmol) in 5 mL dioxane, add 2 M aqueous sodium carbonate solution (1.25 mL, 2.5 mmol), deoxygenate by bubbling nitrogen gas through the suspension for at least 15 minutes. Add tetrakis(triphenylphosphine) palladium(0) (58 mg, 0.05 mmol), fit flask with reflux condenser and heat at 70° C. for 16 hours under a nitrogen atmosphere. Cool reaction mixture to room temperature, dilute with EtOAc (70 mL), wash with 20 mL aqueous saturated sodium chloride, separate layers and back-extract the aqueous layer with 40 mL EtOAc. Combine organic layers, dry over MgSO4, filter directly onto a 10 g SCX cartridge pre-washed with 1:1 dichloromethane:MeOH. Wash and elute product from cartridge with 1:1 dichloromethane:MeOH and 1:1 dichloromethane:2 N NH$_3$-MeOH, respectively, then concentrate the eluate in vacuo to provide yellow oil. Purify the oil on a 40 g silica cartridge with 100% dichloromethane for 5 minutes followed by a gradient of 0→5% MeOH in dichloromethane over 35 minutes. Pool and concentrate clean fractions to afford 188 mg (37%) of the title compound as yellow crystals. LCMS (ES) m/z 498 (M+1).

Example 173

2-[4-(7-Pyridin-4-yl-imidazo[1,2-a]pyridin-3-yl)-phenyl]-N-(3-trifluoromethyl-phenyl)-acetamide

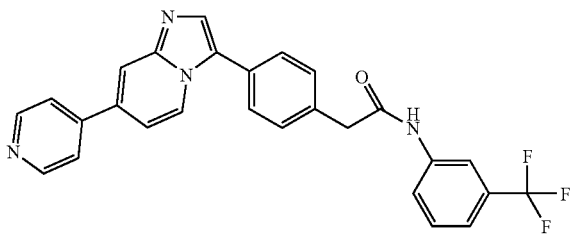

Free base Method A, Form III:

Charge 7-pyridin-4-yl-imidazo[1,2-a]pyridine (19.5 g, 100 mmol), 2-(4-bromo-phenyl)-N-(3-trifluoromethyl-phenyl)-acetamide (35.8 g, 100 mmol), potassium acetate (49.0 g, 500 mmol), tetrabutylammonium bromide (32.2 g, 100 mmol) and NMP (250 mL) into a 3 L flask, at ambient temperature. Flush the flask with nitrogen and add palladium acetate (1.1 g, 5 mol %) and tris-(2,4-di-t-butylphenyl)phosphite (3.2 g, 5 mol %) were added. Flush the flask with nitrogen and heat to 120° C. for 2 hours. Allow reaction to come to ambient temperature and add 250 mL water. Bring the solution to pH=1 with conc. HCl and add 200 mL ethyl acetate. Separate the layers and bring the aqueous layer to pH=10 with NaOH. Stir the slurry at ambient temperature overnight, filter, wash with water, collect and dry under vacuum at 60° C. to afford 35.78 g of a yellow solid. Purify the yellow solid on silica gel chromatography by eluting with dioxane (63.5%)/heptane (34%)/2M ammonia in MeOH (2.5%). Further purify by elution through a second silica gel column with THF (42%)/methylene chloride (55.5%)/2M ammonia in MeOH (2.5%) to afford 30 g of the title compound as a yellow solid (>99% purity by HPLC). Heat a portion of the title compound (5 g) at reflux in acetonitrile (15 mL) for 30 minutes, then cool to ambient temperature. Stir the yellow suspension at ambient temperature for 30 minutes, cool to 0° C., filter, and dry under vacuum at 60° C. to afford 4.77 g of a yellow solid having a melting point of 217° C.

$^1$H-NMR (300 MHz, DMSO-d$_6$) δ 8.7 (m, 3H), 8.25 (s, 1H), 8.15 (s, 1H), 7.9 (m, 3H), 7.7 (d, 1H), 7.65 (d, 2H), 7.55 (m, 3H), 7.4 (m, 2H), 3.8 (s, 2H).

Preparation of Free Base Form II Polymorph

Heat 2-[4-(7-pyridin-4-yl-imidazo[1,2-a]pyridin-3-yl)-phenyl]-N-(3-trifluoromethyl-phenyl)-acetamide (0.5 g) and methanol (5 mL) to reflux to give a solution. Add water (approx. 2 mL) dropwise until the cloud point is reached. Continue to heat and stir the gummy solid until the solid crystallizes. Cool the suspension to ambient temperature over 45 min, then filter and dry in a vacuum oven at 60° C. to afford 0.47 g of the form II polymorph. mp 202° C.

Preparation of Free Base Form I Polymorph

Heat 2-[4-(7-pyridin-4-yl-imidazo[1,2-a]pyridin-3-yl)-phenyl]-N-(3-trifluoromethyl-phenyl)-acetamide (190 g) and methanol (1530 mL) to 60° C. with stirring in a 5 L flask to give a solution. Add water (670 mL) slowly until the cloud point is reached. Cool the cloudy solution to 50° C., where an oil begins to separate from solution. Allow the mixture to cool to ambient temperature and stir overnight (18 h) to yield a suspension of crystals. Cool the suspension in an ice/water bath, filter, and dry in a vacuum oven at 60° C. to afford 163 g of the form I polymorph. mp 193° C.

Succinate Salt

Add 2-[4-(7-pyridin-4-yl-imidazo[1,2-a]pyridin-3-yl)-phenyl]-N-(3-trifluoromethyl-phenyl)-acetamide (4.5 g, 9.4 mmol) to isopropyl alcohol (120 mL) and heated to 80° C. to give a solution. Dissolve succinic acid (1.11 g, 9.4 mmol) in isopropyl alcohol (15 mL) by heating to 80° C. Combine the two solutions and concentrate to a volume of 70 mL to give a suspension. Cool the suspension to 0° C., filter and dry to afford 4.7 g of the succinate salt as a yellow solid. Recrystallize 4.4 g of the crude product from isopropyl alcohol (40 mL) to afford 3.66 g of a yellow solid. $^1$H-NMR (300 MHz, DMSO-d$_6$) δ 2.40 (s, 4H), 3.76 (s, 2H), 7.37-7.88 (m, 11H), 8.11 (s, 1H), 8.22 (s, 1H), 8.66 (m, 3H), 10.56 (s, 1H), 12.12 (s, 2H).

Mono-Hydrochloride Salt

Dissolve 2-[4-(7-pyridin-4-yl-imidazo[1,2-a]pyridin-3-yl)-phenyl]-N-(3-trifluoromethyl-phenyl)-acetamide (4.5 g, 9.4 mmol) in refluxing isopropyl alcohol (80 mL), then add 5N HCl (1.88 mL, 9.4 mmol) in one portion. Cool the mixture to 23° C. and evaporate off the solvent to afford a non-crystalline solid. Suspend this solid in water (100 mL) and heat with stirring to 90° C., then allow to cool to 23° C. and stir overnight. Filter the suspension and dry to afford 3.75 g of the mono-HCl salt as a light orange solid. $^1$H-NMR (300 MHz, DMSO-d$_6$) δ 3.81 (s, 2H), 7.36-8.14 (m, 12H), 8.34 (s, 1H), 8.74 (m, 3H), 10.84 (s, 1H).

Free Base Method B Amorphous:

Suspend 3-iodo-7-pyridin-4-yl-imidazo[1,2-a]pyridine (0.39 g, 1.21 mmol), 2-[4-(4,4,5,5-tetramethyl-[1,3,2]dioxaborolan-2-yl)-phenyl]-N-(3-trifluoromethyl-phenyl)-acetamide (0.73 g, 1.80 mmol) and potassium carbonate (0.50 g, 3.63 mmol) in a solution of dioxane (14 mL) and water (7 mL). Deoxygenate the reaction contents with nitrogen for 10 minutes at room temperature. Add trans-Dichlorobis(triphenylphosphine)-palladium (II) (22 mg, 0.03 mmol) to the reaction. Fit a reflux condenser and heat the reaction to 105° C. for 3 hours. Cool the reaction and dilute with ethyl acetate (75 mL) and separate the layers. Extract the aqueous layer with EtOAc (2×30 mL). Pool the organics, dry over MgSO₄ and filter onto a Varian SCX column (10 g) prewashed with methanol. Elute the column with dichloromethane, 1:1 methanol/dichloromethane and methanol (50 mL each). Elute the title compound with 2 N NH₃/methanol (100 mL). Concentrate the methanolic solution to dryness and chromatograph on silica using 8→10% methanol gradient in 1:1 ethyl acetate:dichloromethane over 45 minutes to give the title compound (0.32 g, 54%). MS(ES), m/z 473 (M+1).

Prepare the following according to procedures similar to Example 173 Free base Method B:

| Ex. | Compound Name | Physical Data MS (ES) (m/z) |
|---|---|---|
| 174 | 2-{4-[7-(4-Methanesulfonyl-phenyl)-imidazo[1,2-a]pyridin-3-yl]-phenyl}-N-(3-trifluoromethyl-phenyl)-acetamide | 550 (M + 1) |
| 175 | N-(5-tert-Butyl-isoxazol-3-yl)-2-[4-(7-pyridin-4-yl-imidazo[1,2-a]pyridin-3-yl)-phenyl]-acetamide | 452 (M + 1) |
| 176 | N-(5-tert-Butyl-2-methyl-2H-pyrazol-3-yl)-2-[4-(7-pyridin-4-yl-imidazo[1,2-a]pyridin-3-yl)-phenyl]-acetamide | 465 (M + 1) |
| 177 | N-(5-tert-Butyl-2-methyl-2H-pyrazol-3-yl)-2-[4-(7-thiazol-2-yl-imidazo[1,2-a]pyridin-3-yl)-phenyl]-acetamide | 471 (M + 1) |
| 178 | N-(5-tert-Butyl-[1,3,4]thiadiazol-2-yl)-2-[4-(7-pyridin-4-yl-imidazo[1,2-a]pyridin-3-yl)-phenyl]-acetamide | 469 (M + 1) |
| 179 | N-(5-tert-Butyl-[1,3,4]thiadiazol-2-yl)-2-[4-(7-thiazol-2-yl-imidazo[1,2-a]pyridin-3-yl)-phenyl]-acetamide | 475 (M + 1) |
| 180 | N-(5-tert-Butyl-[1,3,4]thiadiazol-2-yl)-2-{4-[7-(4-methanesulfonyl-phenyl)-imidazo[1,2-a]pyridin-3-yl]-phenyl}-acetamide | 547 (M + 1) |
| 181 | 2-[4-(7-Pyridin-4-yl-imidazo[1,2-a]pyridin-3-yl)-phenyl]-N-(4-trifluoromethyl-pyridin-2-yl)-acetamide | 474 (M + 1) |
| 182 | 2-{4-[7-(4-Methanesulfonyl-phenyl)-imidazo[1,2-a]pyridin-3-yl]-phenyl}-N-(4-trifluoromethyl-pyridin-2-yl)-acetamide | 551 (M + 1) |
| 183 | 2-{4-[7-(6-Methyl-pyridin-3-yl)-imidazo[1,2-a]pyridin-3-yl]-phenyl}-N-(3-trifluoromethyl-phenyl)-acetamide | 487 (M + 1) |
| 184 | 2-{4-[7-(2-Methyl-pyridin-4-yl)-imidazo[1,2-a]pyridin-3-yl]-phenyl}-N-(3-trifluoromethyl-phenyl)-acetamide | 487 (M + 1) |
| 185 | 2-[4-(7-Pyridin-2-yl-imidazo[1,2-a]pyridin-3-yl)-phenyl]-N-(3-trifluoromethyl-phenyl)-acetamide | 473 (M + 1) |
| 186 | 2-{2-Fluoro-4-[7-(2-methyl-pyridin-4-yl)-imidazo[1,2-a]pyridin-3-yl]-phenyl}-N-(3-trifluoromethyl-phenyl)-acetamide | 505 (M + 1) |
| 187 | 2-[2-Fluoro-4-(7-pyridin-4-yl-imidazo[1,2-a]pyridin-3-yl)-phenyl]-N-(3-trifluoromethyl-phenyl)-acetamide | 491 (M + 1) |
| 188 | 2-[2-Fluoro-4-(7-pyridin-2-yl-imidazo[1,2-a]pyridin-3-yl)-phenyl]-N-(3-trifluoromethyl-phenyl)-acetamide | 491 (M + 1) |
| 189 | N-(4-Chloro-3-trifluoromethyl-phenyl)-2-{4-[7-(4-methanesulfonyl-phenyl)-imidazo[1,2-a]pyridin-3-yl]-phenyl}-acetamide | 584 |
| 190 | N-(4-Chloro-3-trifluoromethyl-phenyl)-2-[4-(7-pyridin-4-yl-imidazo[1,2-a]pyridin-3-yl)-phenyl]-acetamide | 507 |
| 191 | 2-[2-Chloro-4-(7-pyridin-4-yl-imidazo[1,2-a]pyridin-3-yl)-phenyl]-N-(3-trifluoromethyl-phenyl)-acetamide | 507 |
| 192 | N-(5-tert-Butyl-isoxazol-3-yl)-2-[2-chloro-4-(7-pyridin-4-yl-imidazo[1,2-a]pyridin-3-yl)-phenyl]-acetamide | 486 |
| 193 | 2-[2-Chloro-4-(7-pyridin-4-yl-imidazo[1,2-a]pyridin-3-yl)-phenyl]-N-(4-trifluoromethyl-pyridin-2-yl)-acetamide | 508 |
| 194 | N-(2-Fluoro-5-trifluoromethyl-phenyl)-2-{4-[7-(4-methanesulfonyl-phenyl)-imidazo[1,2-a]pyridin-3-yl]-phenyl}-acetamide | 568 (M + 1) |
| 195 | N-(5-tert-Butyl-isoxazol-3-yl)-2-{4-[7-(4-methanesulfonyl-phenyl)-imidazo[1,2-a]pyridin-3-yl]-phenyl}-acetamide | 529 (M + 1) |
| 196 | N-(5-tert-Butyl-isoxazol-3-yl)-2-{2-fluoro-4-[7-(4-methanesulfonyl-phenyl)-imidazo[1,2-a]pyridin-3-yl]-phenyl}-acetamide | 547 (M + 1) |
| 197 | N-(5-tert-Butyl-isoxazol-3-yl)-2-[2-fluoro-4-(7-pyridin-4-yl-imidazo[1,2-a]pyridin-3-yl)-phenyl]-acetamide | 470 (M + 1) |
| 198 | N-(2-Fluoro-5-trifluoromethyl-phenyl)-2-[4-(7-pyridin-4-yl-imidazo[1,2-a]pyridin-3-yl)-phenyl]-acetamide | 491 (M + 1) |
| 199 | N-(5-tert-Butyl-isoxazol-3-yl)-2-[2-fluoro-4-(7-pyridin-2-yl-imidazo[1,2-a]pyridin-3-yl)-phenyl]-acetamide | 470 (M + 1) |
| 200 | 2-[2-Fluoro-4-(7-pyridin-4-yl-imidazo[1,2-a]pyridin-3-yl)-phenyl]-N-(4-trifluoromethyl-pyridin-2-yl)-acetamide | 492 (M + 1) |
| 201 | 2-[2-Fluoro-4-(7-pyridin-4-yl-imidazo[1,2-a]pyridin-3-yl)-phenyl]-N-(4-isopropyl-pyridin-2-yl)-acetamide | 466 (M + 1) |
| 202 | 2-[2-Fluoro-4-(7-pyridin-2-yl-imidazo[1,2-a]pyridin-3-yl)-phenyl]-N-(4-trifluoromethyl-pyridin-2-yl)-acetamide | 492 (M + 1) |

Example 203

Prepare the following according to procedures similar to Example 126:

| Compound Name | Physical Data MS (ES), (m/z) |
|---|---|
| N-(5-tert-Butyl-isoxazol-3-yl)-3-{4-[7-(4-methanesulfonyl-phenyl)-imidazo[1,2-a]pyridin-3-yl]-phenyl}-propionamide | 543 (M + 1) |

Example 204

2-[2-Amino-4-(7-pyridin-4-yl-imidazo[1,2-a]pyridin-3-yl)-phenyl]-N-(4-trifluoromethyl-pyridin-2-yl)-acetamide

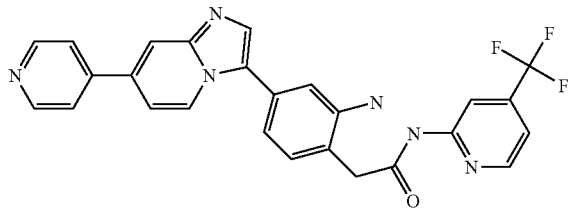

Suspend 2-[2-nitro-4-(7-pyridin-4-yl-imidazo[1,2-a]pyridin-3-yl)-phenyl]-N-(4-trifluoromethyl-pyridin-2-yl)-acetamide (0.18 g, 0.35 mmol) and ammonium formate (0.11 g, 1.82 mmol) in anhydrous methanol (5 mL) and bubble nitrogen through the solution for 5 minutes. Under a positive stream of nitrogen, add 10% Pd-on carbon (0.03, 0.03 mmol) to the solution and stir the reaction at ambient temperature for 18 hours. Filter the reaction contents through a pad of Celite® and wash the pad with methanol (40 mL). Concentrate the solution and then chromatograph the residue on silica using a gradient of (0→2→5%) methanol in dichloromethane to yield the title compound (0.03 g, 0.05 mmol). MS(ES), m/z 489 (M+1).

Example 205

N-[3-(1-Dimethylamino-1-methyl-ethyl)-phenyl]-2-[2-fluoro-4-(7-pyridin-4-yl-imidazo[1,2-a]pyridin-3-yl)-phenyl]-acetamide

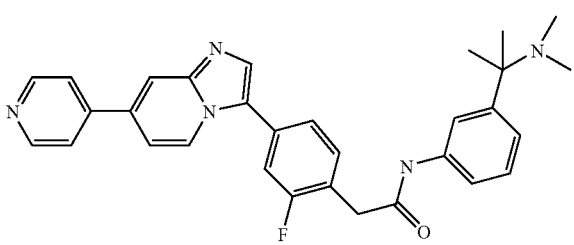

A. (1-{3-[2-(4-Bromo-2-fluoro-phenyl)-acetylamino]-phenyl}-1-methyl-ethyl)-carbamic acid tert-butyl ester Dissolve (4-bromo-2-fluoro-phenyl)acetic acid (1.49 g, 6.39 mmol) in 25 mL amylene-stabilized chloroform and add hydroxybenzotriazole hydrate (0.95 g, 7.03 mmol), to give a slurry. Add 1-[3-(dimethylamino)propyl]-3-ethylcarbodiimide hydrochloride (1.47 g, 7.67 mmol) and stir the resulting clear solution at room temperature for 15 minutes. Add [1-(3-amino-phenyl)-1-methyl-ethyl]-carbamic acid tert-butyl ester and stir for 90 minutes at room temperature. Dilute reaction with 20 mL dichloromethane and wash with saturated NaHCO$_3$, 1 N NaHSO$_4$, and dilute aqueous saturated sodium chloride, then dry over MgSO$_4$ and concentrate to give a brittle tan foam. Purify the foam on a 120 g silica cartridge with 100% CH$_2$Cl$_2$ for 5 minutes followed by a gradient of 0→10% EtOAc in CH$_2$Cl$_2$ over 40 minutes. Concentrate and dry clean fractions to provide 2.11 g (71%) of the title compound as a brittle white foam. LCMS (ES) m/z 463/465 (M−1).

B. [1-(3-{2-[2-Fluoro-4-(7-pyridin-4-yl-imidazo[1,2-a]pyridin-3-yl)-phenyl]-acetylamino}-phenyl)-1-methyl-ethyl]-carbamic acid tert-butyl ester Prepare with coupling methods as described in example 219 (below) with 1-{3-[2-(4-bromo-2-fluoro-phenyl)-acetylamino]-phenyl}-1-methyl-ethyl)-carbamic acid tert-butyl ester (0.465 g, 1 mmol) and 7-pyridin-4-yl-imidazo[1,2a]pyridine (0.195 g, 1 mmol) to give 450 mg (77%) of the title compound as a yellow-green foam after flash column chromatography. LCMS (ES) m/z 580 (M+1).

C. N-[3-(1-Amino-1-methyl-ethyl)-phenyl]-2-[2-fluoro-4-(7-pyridin-4-yl-imidazo[1,2-a]pyridin-3-yl)-phenyl]-acetamide Dissolve [1-(3-{2-[2-fluoro-4-(7-pyridin-4-yl-imidazo[1,2a]pyridin-3-yl)-phenyl]-acetylamino}-phenyl)-1-methyl-ethyl]-carbamic acid tert-butyl ester (450 mg, 0.77 mmol) in 2 mL dioxane and 1 mL water to give a clear yellow solution. Add 8 mL of 4N HCl-dioxane solution and stir at room temperature 1-2 hours. Remove volatiles in vacuo and make the free base as a crusty yellow solid with a 10 g SCX cartridge. Concentrate SCX eluates and purify by flash chromatography on a 40 g silica cartridge with 95:5 CH$_2$Cl$_2$:MeOH, then 95:5 CH$_2$Cl$_2$:2 N NH$_3$-MeOH. Concentrate pure fractions to yield 313 mg (84%) of the title compound as a pale yellow foam. LCMS (ES) m/z 480 (M+1).

D. N-[3-(1-Dimethylamino-1-methyl-ethyl)-phenyl]-2-[2-fluoro-4-(7-pyridin-4-yl-imidazo[1,2-a]pyridin-3-yl)-phenyl]-acetamide Dissolve N-[3-(1-amino-1-methyl-ethyl)-phenyl]-2-[2-fluoro-4-(7-pyridin-4-yl-imidazo[1,2a]pyridin-3-yl)-phenyl]-acetamide (185 mg, 0.385 mmol) in 3 mL absolute ethanol, add sodium acetate (190 mg, 2.31 mmol) and paraformaldehyde (129 mg, 1.43 mmol) and stir together under nitrogen for 15 minutes at room temperature. Add sodium cyanoborohydride (90 mg, 1.43 mmol) and stir under nitrogen for 16 hours at room temperature. Dilute reaction mixture with 10 mL 1 N aqueous HCl and stir the clear yellow solution at room temperature for 15 minutes. Adjust the solution to pH ~8 with 1 N aqueous NaOH, extract twice with 20 mL portions of dichloromethane. Combine organic layers, dry over MgSO$_4$ and concentrate to give a yellow film. Purify the film on a rotary chromatograph using a 1 mm thick disk and 93:7 CH$_2$Cl$_2$:2N NH$_3$-MeOH as eluent. Concentrate and dry pure fractions to provide 131 mg (67%) of the title compound as a yellow foam. LCMS (ES) m/z 508 (M+1).

Example 206

N-(5-tert-butyl-isoxazol-3-yl)-3-[3-(7-thiazol-2-yl-imidazo[1,2-a]pyridin-3-yl)-phenyl]-propionamide

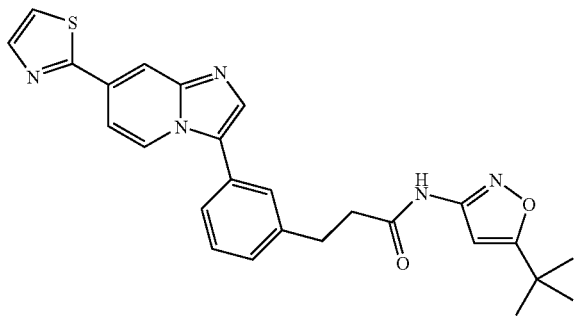

A. 3-(3-Bromo-phenyl)-N-(5-tert-butyl-isoxazol-3-yl)-propionamide

Stir a solution of 3-(3-bromo-phenyl)-propionic acid (1.930 g, 8.43 mmol, 1.0 eq.) 3-amino-5-tert-butylisoxazole (1.299 g, 9.27 mmol, 1.1 eq.) in THF (30 mL) at room temperature for 10 minutes. Add 4-(4,6-dimethoxy-1,3,5-triazin-2-yl)-4-methylmorpho-linium chloride (DMTMM, 2.56 g, 1.1 eq.) and N-methyl morpholine (0.1 mL) to the mixture. Stir the reaction mixture at room temperature for about 16 hours, concentrate in vacuo, then add DCM (100 mL), wash with saturated aqueous sodium chloride (2×20 mL) and water (2×20 mL), dry, filter and concentrate. Purify the concentrated material by silica gel flash chromatography employing dichloromethane to furnish 1.25 g (3.56 mmol, 42%) of the title amide as a white solid. MS (ES), m/z 351, 353 (M+1).

B. N-(5-tert-butyl-isoxazol-3-yl)-3-[3-(7-thiazol-2-yl-imidazo[1,2-a]pyridin-3-yl)-phenyl]-propionamide To a solution of 3-(3-bromo-phenyl)-N-(5-tert-butyl-isoxazol-3-yl)-propionamide (1.090 g, 3.1 mmol, 1.0 eq.) in DMSO (10 mL), add bis(pinacolato)diboron (0.794 g, 3.1 mmol, 1.0 eq.), potassium acetate (0.912 g, 3.0 eq.), and [1,1'-bis(diphenylphosphino)-ferrocene]dichloropalladium (II) (0.068 g, 3 mmol %). Deoxygenate the reaction mixture, stir under nitrogen at 80° C. for about 16 hours, and cool to room temperature. Add diethyl ether (160 mL), wash with saturated aqueous saturated sodium chloride (2×30 mL) and water (2×30 mL), dry, filter and concentrate to provide 1.30 g of a brown solid. Dissolve a portion (0.370 g, 0.93 mmol, 1.0 eq.) of the solid in dioxane (20 mL), then add 3-bromo-7-thiazol-2-yl-imidazo[1,2-a]-pyridine (0.260 g, 093 mmol, 1.0 eq.), sodium carbonate solution (2 M, 4 mL) and tetrakis (triphenylphosphine)palladium (0) (0.054, mmol %). Deoxygenate the reaction mixture with nitrogen and stir at 80° C. for 16 hours. The mixture is purified on a 5 g SCX column (Varian) as in Example 173. Concentrate the SCX eluates and purify via silica gel flash chromatography using a 0-4% methanol/dichloromethane gradient to supply 0.168 g (0.36 mmol, 40%) of the title compound as a slightly yellow solid. MS (ES), m/z 472 (M+1).

Prepare the following according to procedures similar to Example 206:

| Ex. | Compound Name | Physical Data MS (ES) (m/z) |
|---|---|---|
| 207 | N-(5-tert-butyl-isoxazol-3-yl)-3-[3-(7-pyridin-4-yl-imidazo[1,2-a]pyridin-3-yl)-phenyl]-propionamide | 466 (M + 1) |
| 208 | N-(4-tert-butyl-6-methyl-pyridin-2-yl)-2-[4-(7-pyridin-4-yl-imidazo[1,2-a]pyridin-3-yl)-phenyl]-acetamide | 476 (M + 1) |

Example 209

N-(5-tert-Butyl-isoxazol-3-yl)-2-(4-{7-[4-(2-diethylamino-ethanesulfonyl)-phenyl]-imidazo[1,2-a]pyridin-3-yl}-phenyl)-acetamide

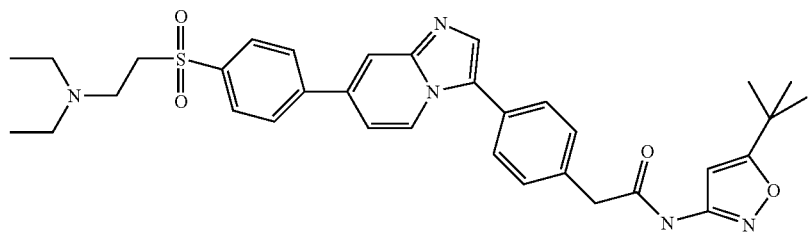

A. [2-(4-Bromo-benzenesulfonyl)-ethyl]-carbamic acid tert-butyl ester

Suspend (4-Bromobenzenesulfonyl)-acetonitrile (10.41 g, 40.02 mmol) in THF and cooled to 0° C., and add borane-dimethylsulfide complex (10 M, 12 mL, 120 mmol) to the suspension which is allowed to slowly warm to ambient temperature. The next day, quench the reaction with a slow addition of methanol until off-gassing ceases. Concentrate the reaction to dryness and add more methanol and bring to reflux for 3 hours. Concentrate the reaction to dryness, then dissolve in dichloromethane and extract with 1 N HCl (2×150 mL). Make the acidic aqueous extracts basic using 50% NaOH and Na₂CO₃. Treat the aqueous solution with dioxane (500 mL) and di-tertbutylcarbonate (10.91 g, 50.00 mmol) for 3 days. Dilute the reaction with dichloromethane, separate the layers and re-extract the aqueous with dichloromethane. Wash the organic extracts with aqueous saturated sodium chloride, dry over MgSO4, filter and concentrate to yield a crude oil. Chromatograph on silica utilizing (0→5→8%) ethyl acetate in dichloromethane to afford the title compound (4.20 g, 11.53 mmol). MS(ES), m/z 307/309 (M+1 minus t-butyl).

B. {2-[4-(4,4,5,5-Tetramethyl-[1,3,2]dioxaborolan-2-yl)-benzenesulfonyl]-ethyl}-carbamic acid tert-butyl ester Use a procedure similar to Preparation 84B, where [2-(4-bromo-benzenesulfonyl)-ethyl]-carbamic acid tert-butyl ester (4.10 g, 11.25 mmol) is converted to the boronate ester (3.03 g, 7.36 mmol). MS(ES), m/z 353 (M+1 minus t-butyl).

C. 2-(4-{7-[4-(2-Amino-ethanesulfonyl)-phenyl]-imidazo[1,2-a]pyridin-3-yl}-phenyl)-N-(5-tert-butyl-isoxazol-3-yl)-acetamide Couple N-(5-tert-Butyl-isoxazol-3-yl)-2-[4-(7-chloro-imidazo[1,2-a]pyridin-3-yl)-phenyl]-acetamide (0.700 g, 1.71 mmol) to {2-[4-(4,4,5,5-Tetramethyl-[1,3,2]dioxaboro-lan-2-yl)-benzenesulfonyl]-ethyl}-carbamic acid tert-butyl ester (0.775 g, 1.88 mmol) using procedure similar to Example 115. Treat the crude extracts to SCX ion exchange chromatography during which time some of the BOC-group is cleaved. Elute from the SCX column and treat with 2N HCl in dioxane (125 mL) and 10 mL of methanol for 2 hours. Evaporate in vacuo to provide the intermediate (0.87 g, 1.38 mmol). MS(ES), m/z 616 (M+1).

D. N-(5-tert-Butyl-isoxazol-3-yl)-2-(4-{7-[4-(2-di-ethylamino-ethanesulfonyl)-phenyl]-imidazo[1,2-a]pyridin-3-yl}-phenyl)-acetamide Combine 2-(4-{7-[4-(2-Amino-ethanesulfonyl)-phenyl]-imidazo[1,2-a]pyridin-3-yl}-phenyl)-N-(5-tert-butyl-isox-azol-3-yl)-acetamide (0.87 g, 1.38 mmol) with acetic acid (1 mL), methanol (20 mL) and acetaldehyde (0.152 g, 3.45 mmol) at ambient temperature under nitrogen for 10 minutes. Add sodium cyanoborohydride at ambient temperature. The reaction is complete within 3 hours. Evaporate under vacuum, re-dissolved in methanol and dichloromethane and load onto an SCX column. Wash the column with dichloromethane (50 mL) and methanol (50 mL) and elute with methanolic ammonia. Chromatography on silica (0→2→4→5%) methanol and dichloromethane gives the title compound (21.0 mg). MS(ES), m/z 614 (M+1).

Example 210

3-{4-[7-(4-Methanesulfonyl-phenyl)-imidazo[1,2-a]pyridin-3-yl]-phenyl}-N-(3-trifluoromethyl-phenyl)-propionamide

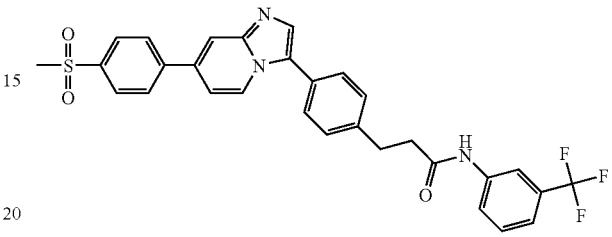

Combine 3-{4-[7-(4-methanesulfonyl-phenyl)-imidazo[1,2-a]pyridin-3-yl]-phenyl}-propionic acid (132 mg, 0.314 mmol, 1.0 equiv) with anhydrous dichloromethane (6.0 mL) in the presence of a catalytic amount of DMF (20 μL). Add 2.0 M oxalyl chloride in dichloromethane (235 μL, 1.5 equiv) via syringe over 30 seconds then stir for 18 hours at room temperature. Concentrate the reaction to dryness under reduced pressure using a rotary evaporator.

Dissolve the crude acid chloride intermediate in anhydrous dichloromethane (3.0 mL) in the presence of DMAP (26.6 mg, 0.218 mmol, 0.3 equiv), 3-trifluoromethyl-phenylamine (181 μL, 1.45 mmol, 2.0 equiv), and pyridine (235 μL, 2.90 mmol, 4.0 equiv) and allow to stir at room temperature for 24 hours. Apply the reaction mixture to SCX resin (10 g), which is eluted with dichloromethane, methanol, then 2.0 M ammonia in methanol. Concentrate the methanolic ammonia fraction to dryness under reduced pressure using a rotary evaporator. Subject the residue to HPLC purification to give 133.0 mg of the title compound. MS (ES) m/z 564 (M+1).

Prepare the following according to procedures similar to Example 210:

| Ex. | Compound Name | Physical Data MS (ES), (m/z) |
|---|---|---|
| 211 | N-(5-tert-butyl-2H-pyrazol-3-yl)-3-{4-[7-(4-methanesulfonyl-phenyl)-imidazo[1,2-a]pyridin-3-yl]-phenyl}-propionamide | 542 (M + 1) |
| 212 | N-(5-tert-butyl-2-methyl-2H-pyrazol-3-yl)-3-{4-[7-(4-methanesulfonyl-phenyl)-imidazo[1,2-a]pyridin-3-yl]-phenyl}-propionamide | 556 (M + 1) |
| 213 | 3-{4-[7-(4-methanesulfonyl-phenyl)-imidazo[1,2-a]pyridin-3-yl]-phenyl}-N-(4-trifluoromethyl-phenyl)-propionamide | 564 (M + 1) |
| 214 | 3-{3-[7-(4-methanesulfonyl-phenyl)-imidazo[1,2-a]pyridin-3-yl]-phenyl}-N-(3-trifluoromethyl-phenyl)-propionamide | 564 (M + 1) |
| 215 | N-(5-tert-butyl-2-p-tolyl-2H-pyrazol-3-yl)-3-{4-[7-(4-methanesulfonyl-phenyl)-imidazo[1,2-a]pyridin-3-yl]-phenyl}-propionamide | 632 (M + 1) |

Example 216

2-[4-(7-Pyridin-4-yl-imidazo[1,2-a]pyridin-3-yl)-phenyl]-N-(3-trifluoromethyl-phenyl)-thioacetamide

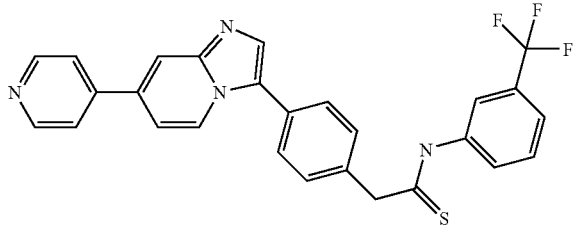

Add Lawesson's reagent (0.246 g, 0.61 mmol, 1.2 eq.) to the solution of 2-[4-(7-pyridin-4-yl-imidazo[1,2-a]pyridin-3-yl)-phenyl]-N-(3-trifluoromethyl-phenyl)-acetamide (0.240 g, 0.51 mmol, 1.0 eq.) in hexamethylphosphoramide (2.5 mL). Stir the reaction mixture at 80° C. overnight. Cool the mixture down to room temperature and load onto a Varian MegaElut® SCX cartridge (5 gram cartridge prewashed with methanol). Rinse with methanol to remove impurities then elute crude product with 2 M $NH_3$ in methanol. Concentrate this solution in vacuo then purify HPLC to give a yellow foam (0.078 g, 31%). MS (ES), m/z 489 (M+1).

Example 217

N-{4-[7-(4-Methanesulfonyl-phenyl)-imidazo[1,2-a]pyridin-3-yl]-benzyl}-2-(m-trifluoromethyl-phenyl)-acetamide

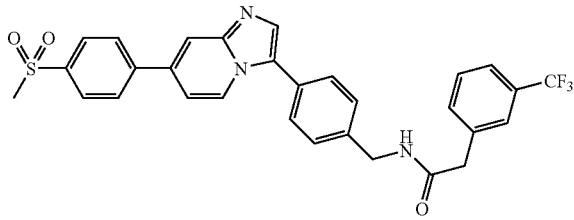

A. N-[4-(7-Chloro-imidazo[1,2-a]pyridin-3-yl)-benzyl]-2-(m-trifluoromethyl-phenyl)-acetamide In a 40 mL septum capped vial purged with $N_2$, add 4-(7-chloro-imidazo[1,2-a]pyridin-3-yl)-benzylamine (125 mg, 0.48 mmol), magnetic stir bar, $CH_2Cl_2$ (6 mL), cool the vial in an ice bath and slowly add 1 mL ($CH_2Cl_2$ solution of m-trifluoromethyl-phenylacetyl chloride, 0.48 mmol). Add isopropyl ethyl amine (0.8 mL) with THF (2 mL). Remove the vial from the ice bath and heat to 40° C. for 6 hours. Add a trace of MeOH and evaporate the solvents under vacuum and take up the oil into a minimal amount of $CH_2Cl_2$ and chromatograph using $SiO_2$ eluting with a gradient of 0.5% to 5% of 2 M $NH_3$ in MeOH with the balance $CH_2Cl_2$. Isolate the product, dry in a vacuum oven at 40° C. for 24 hours to give 144 mg (67%) MS (ES), m/z 444 (M+1).

B. N-{4-[7-(4-Methanesulfonyl-phenyl)-imidazo[1,2-a]pyridin-3-yl]-benzyl}-2-(m-trifluoromethyl-phenyl)-acetamide In a 12 mL septum capped vial purged with $N_2$ add N-[4-(7-chloro-imidazo[1,2-a]pyridin-3-yl)-benzyl]-2-(m-trifluoromethyl-phenyl)-acetamide (144 mg, 0.32 mmol), 4-(methylsulfonyl)phenyl boronic acid (89 mg, 0.44 mmols), 2-dicyclohexylphosphino-2',6'-dimethoxy-1,1'-biphenyl (23.6 mg) [X-Phos is alternatively used as the ligand in this reaction], Pd(OAc)$_2$ (6 mg), $K_3PO_4$ (218 mg, 1.02 mmol), 1,4-dioxane: $H_2O$ 2:1 (5 mL). Deoxygenate the vial again with $N_2$ then heat to 45° C. for 24 hours. Cool the reaction and transfer to a separatory funnel and discard the bottom aqueous layer. Evaporate the solvents under vacuum and take up the residue into $CH_2Cl_2$ with a trace of MeOH. Chromatograph the crude reaction on $SiO_2$ eluting with a gradient of 0% to 8% of 2 M $NH_3$ in MeOH with the balance $CH_2Cl_2$ Dry the product in a vacuum oven at 40° C. for 24 hours to give 38.6 mg (21%) MS (ES), m/z 564.3 (M+1).

Prepare the following according to procedures similar to Example 217:

| Ex. | Compound Name | Physical Data MS (ES), (m/z) |
|---|---|---|
| 218 | N-(5-tert-Butyl-thiazol-2-yl)-2-{2-fluoro-4-[7-(4-nitro-phenyl)-imidazo[1,2-a]pyridin-3-yl]-phenyl}-acetamide | 530 (M + 1) |

Example 219

N-(4-tert-Butyl-pyridin-2-yl)-2-{2-fluoro-4-[7-(6-methyl-pyridin-2-yl)-imidazo[1,2-a]pyridin-3-yl]-phenyl}-acetamide

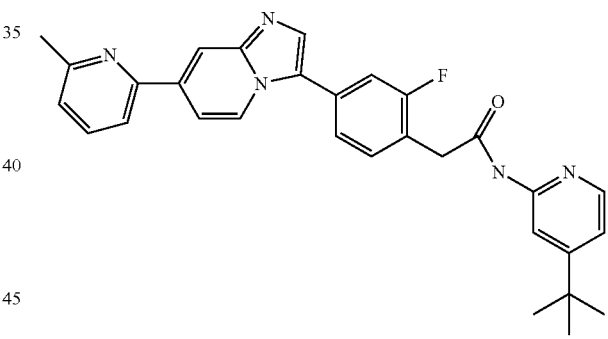

In a stirred septum capped vial, charge 2-(4-bromo-2-fluoro-phenyl)-N-(4-tert-butyl-pyridin-2-yl)-acetamide (400 mg, 1.09 mmol), 7-(6-methyl-pyridin-2-yl)-imidazo[1,2-a]pyridine (228 mg, 1.09 mmol), KOAc (213 mg, 2.18 mmol), $PdCl_2(PPh_3)_2$ and flushes with $N_2$ needle for 15 minutes then one adds DMSO (5 mL) and de-oxygenate with $N_2$ needle and places vial in oil bath at 80 to 90° C. for 24 hours. Cool the reaction then purify by passing through Varian SCX® (10 g) column that is pre-washed with water and methanol, the product being eluted with (20%) 2 N $NH_3$ in methanol/(80%) DCM. Evaporate solvent from the product containing fractions under reduced pressure. Chromatograph using (40 g ISCO®) $SiO_2$ eluting with a gradient of 0% to 10% 2 M $NH_3$ in MeOH with the balance DCM. Evaporate solvents and purify by reverse phase chromatography (C-18 acetonitrile/$H_2O$ with 0.1% TFA) Neutralize, extract, and strip off solvents. Dry in vacuum oven to afford 118.4 mg (21.9%) MS(ES), m/z 494 (M+1).

Prepare the following according to procedures similar to Example 219:

| Ex. | Name | Physical data MS (ES) m/z |
|---|---|---|
| 220 | N-(4-tert-Butyl-pyridin-2-yl)-2-{4-[7-(2-diethylaminomethyl-pyridin-4-yl)-imidazo[1,2-a]pyridin-3-yl]-2-fluoro-phenyl}-acetamide | 565 (M + 1) |
| 221 | N-(5-tert-Butyl-thiazol-2-yl)-2-{4-[7-(2-diethylaminomethyl-pyridin-4-yl)-imidazo[1,2-a]pyridin-3-yl]-2-fluoro-phenyl}-acetamide | 571 (M + 1) |
| 222 | 2-[2-Fluoro-4-(7-pyridin-4-yl-imidazo[1,2-a]pyridin-3-yl)-phenyl]-N-(5-isopropyl-thiazol-2-yl)-acetamide | 472 (M + 1) |
| 223 | N-(5-tert-Butyl-thiazol-2-yl)-2-{4-[7-(2-ethyl-pyridin-4-yl)-imidazo[1,2-a]pyridin-3-yl]-2-fluoro-phenyl}-acetamide | 514 (M + 1) |
| 224 | N-(5-tert-Butyl-thiazol-2-yl)-2-{2-fluoro-4-[7-(2-morpholin-4-ylmethyl-pyridin-4-yl)-imidazo[1,2-a]pyridin-3-yl]-phenyl}-acetamide | 585 (M + 1) |

Example 225

2-[2-Fluoro-4-(7-pyridin-4-yl-imidazo[1,2-a]pyridin-3-yl)-phenyl]-N-(5-isopropyl-4-methyl-thiazol-2-yl)-acetamide

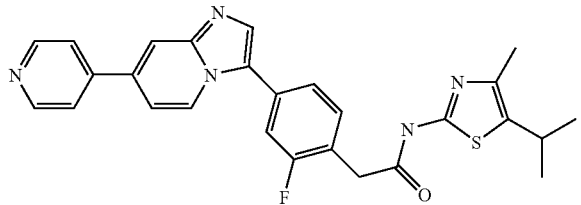

Combine 7-pyridin-4-yl-imidazo[1,2-a]pyridine (0.242 g, 1.24 mmol), 2-(4-Bromo-2-fluoro-phenyl)-N-(5-isopropyl-4-methyl-thiazol-2-yl)-acetamide (0.460 g, 1.24 mmol), and potassium acetate (0.243 g, 2.48 mmol) in DMSO (5 mL). De-gas the mixture with $N_2$ for 10 minutes, then add dichlorobis(triphenylphosphine) palladium(II) (0.087 g, 0.124 mmol). Stir the reaction at 100° C. under $N_2$ for 14 hours. Purify using an SCX cartridge (10 g VARIAN bond elut), eluting with 1:1 methanol:dichloromethane, then 1:1 2 M $NH_3$ in methanol:dichloromethane. The latter is purified via reverse phase chromatography using a 25 cm by 50.8 mm (i.d.) column w/10 micron particles (MeCN/0.03% HCl $H_2O$ (5:95) to 100% MeCN; 30 minutes). Compound obtained is extracted with ethyl acetate versus 1 N NaOH. The organic layer is washed with aqueous saturated sodium chloride. Dry the resulting organics over magnesium sulfate, filter, and concentrate to afford product (0.068 g, 11%). MS(ES), m/z 486 (M+1).

Prepare the following according to procedures similar to Example 219:

| Ex. | Name | Physical data MS (ES) m/z |
|---|---|---|
| 226 | N-(3-Acetyl-phenyl)-2-[2-fluoro-4-(7-pyridin-4-yl-imidazo[1,2-a]pyridin-3-yl)-phenyl]-acetamide | 465 (M + 1) |
| 227 | 2-[2-Fluoro-4-(7-pyridin-4-yl-imidazo[1,2-a]pyridin-3-yl)-phenyl]-N-[5-(1-methyl-cyclopropyl)-[1,3,4]thiadiazol-2-yl]-acetamide | 485 (M + 1) |
| 228 | N-(3-Dimethylaminomethyl-5-trifluoromethyl-phenyl)-2-[2-fluoro-4-(7-pyridin-2-yl-imidazo[1,2-a]pyridin-3-yl)-phenyl]-acetamide | 548 (M + 1) |
| 229 | N-(3-tert-Butyl-5-morpholin-4-ylmethyl-phenyl)-2-[2-fluoro-4-(7-pyridin-4-yl-imidazo[1,2-a]pyridin-3-yl)-phenyl]-acetamide | 578 (M + 1) |
| 230 | N-(3-tert-Butyl-5-dimethylaminomethyl-phenyl)-2-[2-fluoro-4-(7-pyridin-4-yl-imidazo[1,2-a]pyridin-3-yl)-phenyl]-acetamide | 536 (M + 1) |
| 231 | 2-(2-Fluoro-4-{7-[2-(2-morpholin-4-yl-propyl)-pyridin-4-yl]-imidazo[1,2-a]pyridin-3-yl}-phenyl)-N-[5-(1-hydroxy-cyclobutyl)-thiazol-2-yl]-acetamide | 627 (M + 1) |
| 232 | 2-{2-Fluoro-4-[7-(6-methyl-pyridin-2-yl)-imidazo[1,2-a]pyridin-3-yl]-phenyl}-N-(4-trifluoromethyl-pyridin-2-yl)-acetamide | 506 (M + 1) |
| 233 | N-(4-tert-Butyl-pyridin-2-yl)-2-{4-[7-(2,6-dimethyl-pyridin-4-yl)-imidazo[1,2-a]pyridin-3-yl]-2-fluoro-phenyl}-acetamide | 508 (M + 1) |
| 234 | N-(5-tert-Butyl-thiazol-2-yl)-2-(2-fluoro-4-{7-[2-(2-pyrrolidin-1-yl-propyl)-pyridin-4-yl]-imidazo[1,2-a]pyridin-3-yl}-phenyl)-acetamide | 597 (M + 1) |
| 235 | N-(4-tert-Butyl-pyridin-2-yl)-2-(2-fluoro-4-{7-[2-(2-pyrrolidin-1-yl-propyl)-pyridin-4-yl]-imidazo[1,2-a]pyridin-3-yl}-phenyl)-acetamide | 591 (M + 1) |

| Ex. | Name | Physical data MS (ES) m/z |
|---|---|---|
| 236 | N-(5-tert-Butyl-[1,3,4]thiadiazol-2-yl)-2-(2-fluoro-4-{7-[2-(2-pyrrolidin-1-yl-propyl)-pyridin-4-yl]-imidazo[1,2-a]pyridin-3-yl}-phenyl)-acetamide | 598 (M + 1) |
| 237 | 2-(2-Fluoro-4-{7-[6-(2-morpholin-4-yl-propyl)-pyridin-3-yl]-imidazo[1,2-a]pyridin-3-yl}-phenyl)-N-[(5-tert-Butyl)-[1,3,4]thiadiazol-2-yl]-acetamide | 614 (M + 1) |
| 238 | N-(4-tert-Butyl-pyridin-2-yl)-2-(2-fluoro-4-{7-[6-(2-morpholin-4-yl-propyl)-pyridin-3-yl]-imidazo[1,2-a]pyridin-3-yl}-phenyl)-acetamide | 607 (M + 1) |
| 239 | N-(4-tert-Butyl-pyridin-2-yl)-2-(2-fluoro-4-{7-[6-(2-morpholin-4-yl-propyl)-pyridin-2-yl]-imidazo[1,2-a]pyridin-3-yl}-phenyl)-acetamide | 607 (M + 1) |
| 240 | 2-(2-Fluoro-4-{7-[6-(2-morpholin-4-yl-propyl)-pyridin-2-yl]-imidazo[1,2-a]pyridin-3-yl}-phenyl)-N-[5-(1-hydroxy-cyclobutyl)-thiazol-2-yl]-acetamide | 627 (M + 1) |
| 241 | 3-(6-{2-[2-Fluoro-4-(7-pyridin-4-yl-imidazo[1,2-a]pyridin-3-yl)-phenyl]-acetylamino}-2-methyl-4-trifluoromethyl-pyridin-3-yl)-N,N-dimethyl-acrylamide | 603 (M + 1) |
| 242 | 3-(4-tert-Butyl-6-{2-[2-fluoro-4-(7-pyridin-4-yl-imidazo[1,2-a]pyridin-3-yl)-phenyl]-acetylamino}-pyridin-3-yl)-N,N-dimethyl-acrylamide | 577 (M + 1) |
| 243 | 2-[2-Fluoro-4-(7-pyridin-2-yl-imidazo[1,2-☐]pyridin-3-yl)-phenyl]-N-(4-isobutyl-pyridin-2-yl)-acetamide | 480 (M + 1) |
| 244 | N-(4-sec-Butyl-pyridin-2-yl)-2-[2-fluoro-4-(7-pyridin-4-yl-imidazo[1,2-a]pyridin-3-yl)-phenyl]-acetamide | 480 (M + 1) |
| 245 | 2-[2-Fluoro-4-(7-pyridin-4-yl-imidazo[1,2-a]pyridin-3-yl)-phenyl]-N-(4-isobutyl-pyridin-2-yl)-acetamide, hydrochloride salt | 480 (M + 1) |
| 246 | N-(4-Cyclopropyl-pyridin-2-yl)-2-[2-fluoro-4-(7-pyridin-4-yl-imidazo[1,2-a]pyridin-3-yl)-phenyl]-acetamide | 464 (M + 1) |
| 247 | N-(3-tert-Butyl-phenyl)-2-[2-fluoro-4-(7-pyridin-4-yl-imidazo[1,2-a]pyridin-3-yl)-phenyl]-acetamide | 479 (M + 1) |
| 248 | N-(4-Dimethylaminomethyl-pyridin-2-yl)-2-[2-fluoro-4-(7-pyridin-4-yl-imidazo[1,2-a]pyridin-3-yl)-phenyl]-acetamide | 481 (M + 1) |
| 249 | 2-[2-Fluoro-4-(7-pyridin-2-yl-imidazo[1,2-a]pyridin-3-yl)-phenyl]-N-(3-morpholin-4-ylmethyl-5-trifluoromethyl-phenyl)-acetamide | 590 (M + 1) |
| 250 | 2-[2-Fluoro-4-(7-pyridin-4-yl-imidazo[1,2-a]pyridin-3-yl)-phenyl]-N-(3-morpholin-4-ylmethyl-5-trifluoromethyl-phenyl)-acetamide | 590 (M + 1) |
| 251 | 3-{2-[2-Fluoro-4-(7-pyridin-4-yl-imidazo[1,2-a]pyridin-3-yl)-phenyl]-acetylamino}-N-(tetrahydro-pyran-4-yl)-5-trifluoromethyl-benzamide | 618 (M + 1) |
| 252 | 2-[2-Fluoro-4-(7-pyridin-4-yl-imidazo[1,2-a]pyridin-3-yl)-phenyl]-N-[3-(morpholine-4-carbonyl)-5-trifluoromethyl-phenyl]-acetamide, hydrochloride salt | 604 (M + 1) |
| 253 | N-[5-tert-Butyl-4-(2-dimethylamino-ethoxy)-2-methyl-phenyl]-2-[2-fluoro-4-(7-pyridin-4-yl-imidazo[1,2-a]pyridin-3-yl)-phenyl]-acetamide | 580 (M + 1) |
| 254 | N-(5-tert-Butyl-thiazol-2-yl)-2-[4-(7-pyridin-4-yl-imidazo[1,2-a]pyridin-3-yl)-phenyl]-acetamide | 468 (M + 1) |
| 255 | N-(5-tert-Butyl-[1,3,4]thiadiazol-2-yl)-2-[2-chloro-4-(7-pyridin-4-yl-imidazo[1,2-a]pyridin-3-yl)-phenyl]-acetamide | 503 (M + 1) |
| 256 | N-(5-tert-Butyl-thiazol-2-yl)-2-[2-chloro-4-(7-pyridin-4-yl-imidazo[1,2-a]pyridin-3-yl)-phenyl]-acetamide | 502 (M + 1) |
| 257 | N-(4-tert-Butyl-pyridin-2-yl)-2-[2-chloro-4-(7-pyridin-4-yl-imidazo[1,2-a]pyridin-3-yl)-phenyl]-acetamide | 496 (M + 1) |
| 258 | 2-[2-Nitro-4-(7-pyridin-4-yl-imidazo[1,2-a]pyridin-3-yl)-phenyl]-N-(4-trifluoromethyl-pyridin-2-yl)-acetamide | 519 (M + 1) |
| 259 | N-(4-tert-Butyl-pyridin-2-yl)-2-[4-(7-pyridin-4-yl-imidazo[1,2-a]pyridin-3-yl)-phenyl]-acetamide | 462 (M + 1) |
| 260 | N-(4-tert-Butyl-pyridin-2-yl)-2-[4-(7-pyridin-2-yl-imidazo[1,2-a]pyridin-3-yl)-phenyl]-acetamide | 462 (M + 1) |
| 261 | N-(4-tert-Butyl-6-dimethylaminomethyl-pyridin-2-yl)-2-[2-fluoro-4-(7-pyridin-4-yl-imidazo[1,2-a]pyridin-3-yl)-phenyl]-acetamide | 537 (M + 1) |
| 262 | N-(4-tert-Butyl-6-dimethylaminomethyl-pyridin-2-yl)-2-[2-fluoro-4-(7-pyridin-2-yl-imidazo[1,2-a]pyridin-3-yl)-phenyl]-acetamide | 537 (M + 1) |

Example 263

N-(4-tert-butyl-6-morpholin-4-ylmethyl-pyridin-2-yl)-2-[2-fluoro-4-(7-pyridin-4-yl-imidazo[1,2-a]pyridin-3-yl)-phenyl]-acetamide

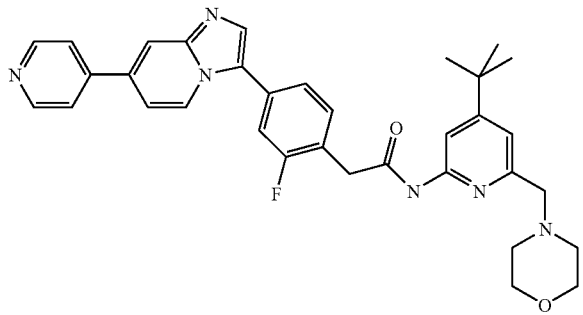

Dissolve [2-fluoro-4-(7-pyridin-4-yl-imidazo[1,2-a]pyridin-3-yl)-phenyl]-acetic acid dihydrochloride (6.24 g, 14.84 mmol) and 4-tert-butyl-6-morpholin-4-ylmethyl-pyridin-2-ylamine (3.70 g, 14.84 mmol) in anhydrous DMF (40 mL). Add diisopropyl-ethylamine (8.5 mL, 48.97 mmol) and HATU (6.21 g, 16.32 mmol). Stir the reaction mixture at room temperature for 40 minutes. Dilute with ethyl acetate (800 mL). Wash with aqueous saturated sodium chloride (3×100 mL), sodium bicarbonate (sat. 3×100 mL), water (3×100 mL). Dry the organic layer over magnesium sulfate, filter off the drying reagent, and concentrate to oil. Chromatograph the crude product on silica (0-4% 2 M ammonia methanol/dichloro-methane). Recrystallize from dichloromethane/ether/hexane to provide the title compound 5.50 g (9.5 mmol, 64%) white solid as product. MS (ES), m/z 579 (M+1).

Prepare the following according to procedures similar to Example 219:

Example 275

N-(5-tert-Butyl-[1,3,4]thiadiazol-2-yl-2-[2-fluoro-4-(7-pyridin-4-yl-imidazo[1,2-a]pyridin-3-yl)-phenyl]-acetamide

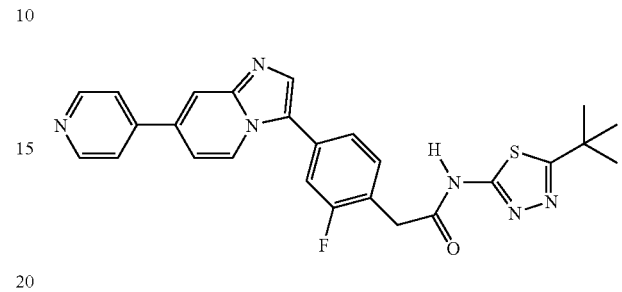

Dissolve 2-(4-bromo-2-fluoro-phenyl)-N-(5-tert-butyl-[1,3,4]thiadiazol-2-yl)-acetamide (0.86 g, 2.31 mmol) and 7-pyridin-4-yl-imidazo[1,2-a]pyridine (0.45 g, 2.31 mmol) in dimethyl sulfoxide (2.5 mL). Add potassium acetate (0.46 g, 4.62 mmol), and trans-dichloro bis(triphenylphosphine) palladium (II) (0.16 g, 0.23 mmol), deoxygenate and fill with nitrogen (2×). Stir the reaction mixture over night at 100° C. under nitrogen. Add ice water (16 mL), filter off the solid and purify via flash silica gel chromatography (0-5% methanol/dichloromethane) to afford 0.72 g (1.48 mmol, 64%) of yellow solid as the title compound. MS (ES), m/z 487.0 (M+1).

Prepare the following according to procedures similar to Example 219:

| Ex. | Name | Physical data MS (ES) m/z |
|---|---|---|
| 264 | N-(4-tert-Butyl-6-morpholin-4-ylmethyl-pyridin-2-yl)-2-[2-fluoro-4-(7-pyridin-2-yl-imidazo[1,2-a]pyridin-3-yl)-phenyl]-acetamide | 579 (M + 1) |
| 265 | N-(4-tert-Butyl-6-pyrrolidin-1-ylmethyl-pyridin-2-yl)-2-[2-fluoro-4-(7-pyridin-2-yl-imidazo[1,2-a]pyridin-3-yl)-phenyl]-acetamide | 563 (M + 1) |
| 266 | N-(4-tert-Butyl-pyridin-2-yl)-2-[2-methyl-4-(7-pyridin-4-yl-imidazo[1,2-a]pyridin-3-yl)-phenyl]-acetamide | 476 (M + 1) |
| 267 | N-(4-tert-Butyl-pyridin-2-yl)-2-[2-methyl-4-(7-pyridin-2-yl-imidazo[1,2-a]pyridin-3-yl)-phenyl]-acetamide | 476 (M + 1) |
| 268 | N-(4-tert-Butyl-6-morpholin-4-ylmethyl-pyridin-2-yl)-2-{2-fluoro-4-[7-(2-methyl-pyridin-4-yl)-imidazo[1,2-a]pyridin-3-yl]-phenyl}-acetamide | 593 (M + 1) |
| 269 | N-(5-Cyclobutyl-thiazol-2-yl)-2-(2-fluoro-4-{7-[2-(2-morpholin-4-yl-propyl)-pyridin-4-yl]-imidazo[1,2-a]pyridin-3-yl}-phenyl)-acetamide | 611 (M + 1) |
| 270 | N-(5-Cyclobutyl-thiazol-2-yl)-2-[2-fluoro-4-(7-pyridin-4-yl-imidazo[1,2-a]pyridin-3-yl)-phenyl]-acetamide | 484 (M + 1) |
| 271 | 2-[2-Fluoro-4-(7-pyridin-4-yl-imidazo[1,2-a]pyridin-3-yl)-phenyl]-N-(5-isopropyl-4-pyrrolidin-1-ylmethyl-thiazol-2-yl)-acetamide | 555 (M + 1) |
| 272 | N-(5-Cyclopropyl-[1,3,4]thiadiazol-2-yl)-2-[2-fluoro-4-(7-pyridin-4-yl-imidazo[1,2-a]pyridin-3-yl)-phenyl]-acetamide | 471 (M + 1) |
| 273 | N-(5-tert-Butyl-thiazol-2-yl)-2-[2-fluoro-4-(7-pyridin-4-yl-imidazo[1,2-a]pyridin-3-yl)-phenyl]-acetamide | 486 (M + 1) |
| 274 | N-(5-tert-Butyl-[1,3,4]thiadiazol-2-yl)-2-[2-fluoro-4-(7-pyridin-2-yl-imidazo[1,2-a]pyridin-3-yl)-phenyl]-acetamide | 487 (M + 1) |

| Ex. | Name | Physical data MS (ES) m/z |
|---|---|---|
| 276 | 2-[2-Fluoro-4-(7-pyridin-2-yl-imidazo[1,2-a]pyridin-3-yl)-phenyl]-N-(3-pyrrolidin-1-ylmethyl-5-trifluoromethyl-phenyl)-acetamide | 574 (M + 1) |
| 277 | 2-[2-Fluoro-4-(7-pyridin-4-yl-imidazo[1,2-a]pyridin-3-yl)-phenyl]-N-(3-pyrrolidin-1-ylmethyl-5-trifluoromethyl-phenyl)-acetamide | 574 (M + 1) |
| 278 | N-(4-tert-Butyl-pyridin-2-yl)-2-[2-fluoro-4-(7-pyridin-4-yl-imidazo[1,2-a]pyridin-3-yl)-phenyl]-acetamide | 480 (M + 1) |
| 279 | N-(4-tert-Butyl-pyridin-2-yl)-2-[2-fluoro-4-(7-pyridin-2-yl-imidazo[1,2-a]pyridin-3-yl)-phenyl]-acetamide | 480 (M + 1) |
| 280 | 2-[2-Fluoro-4-(7-pyridin-4-yl-imidazo[1,2-a]pyridin-3-yl)-phenyl]-N-[5-(1-hydroxy-1-methyl-ethyl)-thiazol-2-yl]-acetamide | 488 (M + 1) |
| 281 | N-(5-tert-Butyl-thiazol-2-yl)-2-{2-fluoro-4-[7-(2-methyl-pyridin-4-yl)-imidazo[1,2-a]pyridin-3-yl]-phenyl}-acetamide | 500 (M + 1) |
| 282 | 2-{2-Fluoro-4-[7-(2-methyl-pyridin-4-yl)-imidazo[1,2-a]pyridin-3-yl]-phenyl}-N-(4-trifluoromethyl-pyridin-2-yl)-acetamide | 506 (M + 1) |
| 283 | N-(4-tert-Butyl-pyridin-2-yl)-2-{2-fluoro-4-[7-(2-methyl-pyridin-4-yl)-imidazo[1,2-a]pyridin-3-yl]-phenyl}-acetamide | 494 (M + 1) |
| 284 | 2-{2-Fluoro-4-[7-(2-methyl-pyridin-4-yl)-imidazo[1,2-a]pyridin-3-yl]-phenyl}-N-[5-(1-hydroxy-1-methyl-ethyl)-thiazol-2-yl]-acetamide | 502 (M + 1) |
| 285 | 2-[2-Fluoro-4-(7-pyridin-2-yl-imidazo[1,2-a]pyridin-3-yl)-phenyl]-N-[5-(1-hydroxy-1-methyl-ethyl)-thiazol-2-yl]-acetamide | 488 (M + 1) |
| 286 | 2-[2-Fluoro-4-(7-pyridin-2-yl-imidazo[1,2-a]pyridin-3-yl)-phenyl]-N-[5-(1-hydroxy-cyclobutyl)-thiazol-2-yl]-acetamide | 500 (M + 1) |
| 287 | 2-[2-Fluoro-4-(7-pyridin-4-yl-imidazo[1,2-a]pyridin-3-yl)-phenyl]-N-[5-(1-hydroxy-cyclobutyl)-thiazol-2-yl]-acetamide | 500 (M + 1) |
| 288 | 2-{2-Fluoro-4-[7-(2-methyl-pyridin-4-yl)-imidazo[1,2-a]pyridin-3-yl]-phenyl}-N-[5-(1-hydroxy-cyclobutyl)-thiazol-2-yl]-acetamide | 514 (M + 1) |
| 289 | N-(6-tert-Butyl-pyrimidin-4-yl)-2-[4-(7-pyridin-4-yl-imidazo[1,2-a]pyridin-3-yl)-phenyl]-acetamide | 463 (M + 1) |
| 291 | N-(6-Methyl-4-trifluoromethyl-pyridin-2-yl)-2-[4-(7-pyridin-4-yl-imidazo[1,2a]pyridin-3-yl)-phenyl]-acetamide. | 488 (M + 1) |

Example 292

2-[2-Fluoro-4-(7-pyridin-4-yl-imidazo[1,2-a]pyridin-3-yl)-phenyl]-N-(5-isopropenyl-thiazol-2-yl)-acetamide

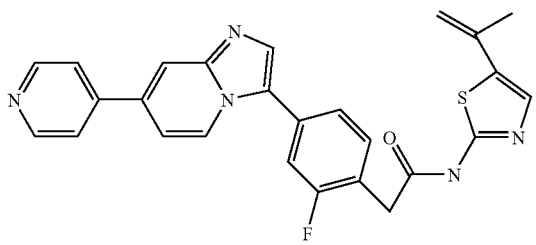

Isolate during the preparation of the Example 2-[2-Fluoro-4-(7-pyridin-4-yl-imidazo[1,2-a]pyridin-3-yl)-phenyl]-N-[5-(1-hydroxy-1-methyl-ethyl)-thiazol-2-yl]-acetamide. MS (ES), m/z 470 (M+1).

Isolate the following similarly from the corresponding carbinol syntheses:

| Ex. | Name | Physical Data MS (ES), (m/z) |
|---|---|---|
| 293 | 2-[2-Fluoro-4-(7-pyridin-2-yl-imidazo[1,2-a]pyridin-3-yl)-phenyl]-N-(5-isopropenyl-thiazol-2-yl)-acetamide | 470 (M + 1) |
| 294 | 2-{2-Fluoro-4-[7-(2-methyl-pyridin-4-yl)-imidazo[1,2-a]pyridin-3-yl]-phenyl}-N-(5-isopropenyl-thiazol-2-yl)-acetamide | 482 (M + 1) |

Example 295 and 296

(R)- and (S)-N-(4-tert-Butyl-pyridin-2-yl)-2-(2-fluoro-4-{7-[2-(2-morpholin-4-yl-propyl)-pyridin-4-yl]-imidazo[1,2-a]pyridin-3-yl}-phenyl)-acetamide

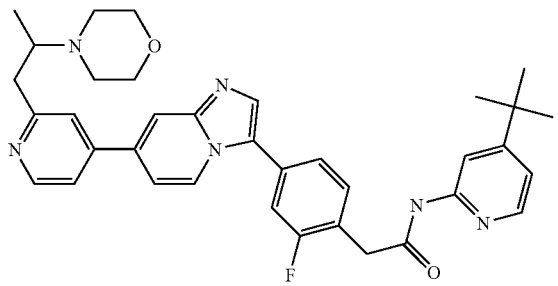

Prepare racemate with procedures similar to Example 219 and separate into enantiomers by chiral HPLC (Column: 0.46×15 cm Chiralcel OD-H, Eluent: 100% 3A ethanol w/0.2% DMEA, Flow: 0.6 mL/min, UV: 260 nm) both enantiomers at approximately 99% ee as characterized by chiral LC. Enantiomer A: MS(ES), m/z 607 (M+1); enantiomer B: MS(ES), m/z 607 (M+1).

Examples 297 and 298

(R)- and (S)-24561102-(2-Fluoro-4-{7-[2-(2-morpholin-4-yl-propyl)-pyridin-4-yl]-imidazo[1,2-a]pyridin-3-yl}-phenyl)-N-(4-trifluoromethyl-pyridin-2-yl)-acetamide

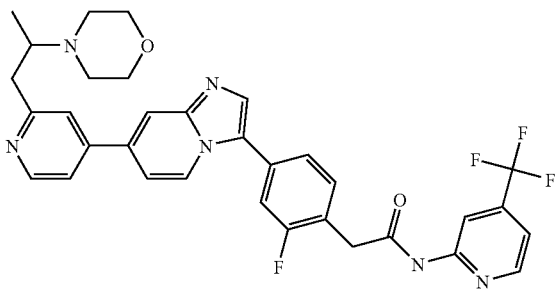

Combine 7-[2-(2-morpholin-4-yl-propyl)-pyridin-4-yl]-imidazo[1,2-a]pyridine (1.0 g, 3.1 mmol), 2-(4-bromo-2-fluoro-phenyl)-N-(4-trifluoromethyl-pyridin-2-yl)-acetamide (1.29 g, 1.1 equiv.), potassium acetate (0.61 g, 2 equiv.), and DMSO (5 mL) in a RBF. Degas thoroughly with nitrogen then add dichloro-bis(triphenylphosphine) palladium (II) (0.22 g, 10 mol %) and heat the reaction overnight at 90° C. Dilute with ethyl acetate and 1N NaOH (aq). Extract organics with water, 1 N NaOH (aq), and brine. Dry organics over magnesium sulfate, filter and concentrate to dryness. Purify by reverse phase (25% MeCN:0.03% HCl in water→100% MeCN, C18 column). Material impure after chromatography. Combine all fractions containing product. Dilute with ethyl acetate then wash with 1 N NaOH followed by brine. Dry organics over magnesium sulfate, filter and concentrate to give impure freebase (1.17 g). Purify on silica gel (3% MeOH:DCM→6% MeOH:DCM→10% MeOH: DCM→10% 2 M NH₃ in MeOH:DCM) to give a light yellow solid (0.977 g). Dry overnight at 60° C. in a vacuum oven. A second silica column (3% MeOH:DCM→6% MeOH:DCM→10% MeOH:DCM) provides clean product (0.656 g). Dry overnight at 60° C. in a vacuum oven to give 0.57 g product (30%). LCMS (ES), m/z 619 (M+1). Separation of enantiomers by chiral HPLC (Column: 0.46×15 cm Chiralcel OD-H, Eluent: 100% 3A ethanol w/0.2% DMEA, Flow: 0.6 ml/min, UV: 260 nm) provided both enantiomers at approximately 99% ee as characterized by chiral LC. Ex 297, Isomer 1—7.3 minutes. Ex 298, Isomer 2—8.8 minutes. Note: absolute stereochemistry not determined.

Example 299 and 300

(R)- and (S)-N-(5-tert-Butyl-thiazol-2-yl)-2-(2-fluoro-4-{7-[2-(2-morpholin-4-yl-propyl)-pyridin-4-yl]-imidazo[1,2-a]pyridin-3-yl}-phenyl)-acetamide

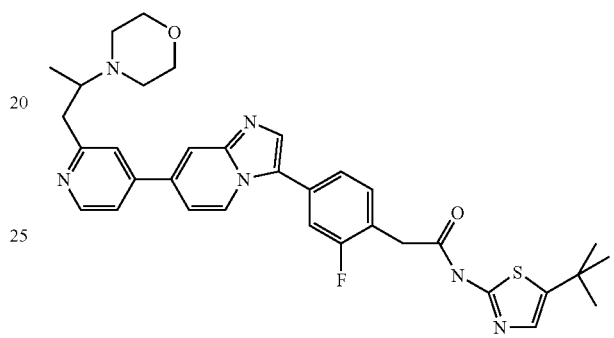

Prepare racemate with procedures similar to Example 219 and separate into enantiomers by chiral HPLC (Column: 0.46×15 cm Chiralcel OD-H, Eluent: 100% 3A ethanol w/0.2% DMEA, Flow: 0.6 mL/min, UV: 260 nm) both enantiomers at approximately 99% ee as characterized by chiral LC. MS(ES), m/z 613.3 (M+1).

Example 301 and 302

(R)- and (S)-2-(2-Fluoro-4-{7-[2-(2-morpholin-4-yl-propyl)-pyridin-4-yl]-imidazo[1,2-a]pyridin-3-yl}-phenyl)-N-[5-(1-methyl-cyclopropyl)-[1,3,4]thiadiazol-2-yl]-acetamide

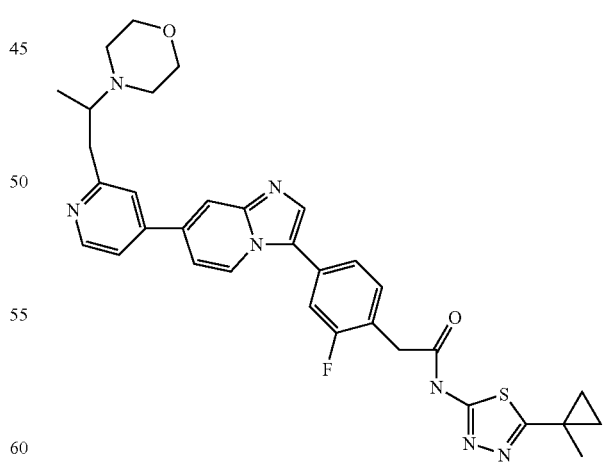

Prepare racemate with procedures similar to Example 219 and separate into enantiomers by chiral HPLC (Column: 0.46×15 cm Chiralcel OD-H, Eluent: 100% 3A ethanol w/0.2% DMEA, Flow: 0.6 mL/min, UV: 260 nm) both enantiomers at approximately 99% ee as characterized by chiral LC. MS(ES), m/z 612.0 (M+1).

Example 303

N-(5-tert-Butyl-isoxazol-3-yl)-2-{4-[7-(1H-pyrazol-4-yl)-imidazo[1,2-a]pyridin-3-yl]-phenyl}-acetamide

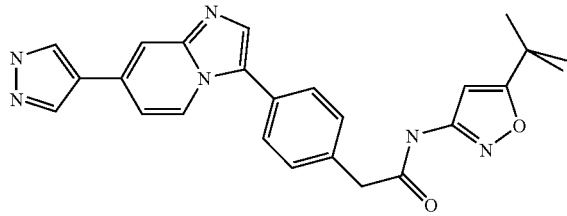

A. N-(5-tert-Butyl-isoxazol-3-yl)-2-{4-[7-(1-dimethylsulfamoyl-1H-pyrazol-4-yl)-imidazo[1,2-a]pyridin-3-yl]-phenyl}-acetamide Prepare with procedures similar to Example 219. MS (ES), m/z 548 (M+1).

B. N-(5-tert-Butyl-isoxazol-3-yl)-2-{4-[7-(1H-pyrazol-4-yl)-imidazo[1,2-a]pyridin-3-yl]-phenyl}-acetamide Dissolve N-(5-tert-Butyl-isoxazol-3-yl)-2-{4-[7-(1-dimethylsulfamoyl-1H-pyrazol-4-yl)-imidazo[1,2-a]pyridin-3-yl]-phenyl}-acetamide in CH$_2$Cl$_2$, methanol and 1 N HCl in ether in equal volumes and then concentrate to give a solid. Dissolve the solid in HOAc and stir for 1 hour. Concentrate and purify by silica gel chromatography with 0-5% MeOH in CH$_2$Cl$_2$. MS(ES), m/z 441 (M+1).

The following example is prepared with a procedure similar to Example 303:

| Ex. | Name | Physical Data MS (ES), (m/z) |
|---|---|---|
| 304 | N-(5-tert-Butyl-thiazol-2-yl)-2-{4-[7-(1H-pyrazol-4-yl)-imidazo[1,2-a]pyridin-3-yl]-phenyl}-acetamide | 457 (M + 1) |

Example 305

2-[2-Fluoro-4-(7-pyridin-4-yl-imidazo[1,2-a]pyridin-3-yl)-phenyl]-N-[5-(tetrahydro-pyran-4-yl)-thiazol-2-yl]-acetamide

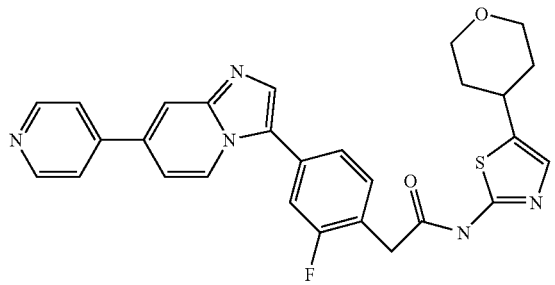

A. 2-[2-fluoro-4-yl-imidazo[1,2-a]pyridine-3-yl)-phenyl]-N-[5-(4-hydroxy-tetrahydro-pyran-4-yl)-thiazol-2-yl]-acetamide The title compound is prepared with procedures similar to Example 219. MS (ES), m/z 530 (M+1).

B. 2-[2-Fluoro-4-(7-pyridin-4-yl-imidazo[1,2-a]pyridin-3-yl)-phenyl]-N-[5-(tetrahydro-pyran-4-yl)-thiazol-2-yl]-acetamide Dissolve compound 2-[2-fluoro-4-yl-imidazo[1,2-a]pyridine-3-yl)-phenyl]-N-[5-(4-hydroxy-tetrahydro-pyran-4-yl)-thiazol-2-yl]-acetamide (0.186 g, 0.35 mmol, 1.0 eq.) in trifluoroacetic acid (8 mL). Add Pearlman's catalyst (0.12 g) to the mixture. Stir the reaction mixture in hydrogen atmosphere (50 psi) for over night. Concentrate in vacuo. Purify by column chromatography (0%→5% 2 M ammonia methanol in dichloromethane) to afford the title product (1.38 g, 46%). MS (ES), m/z 514 (M+1). The following example is prepared with procedures similar to Example 305:

| Ex. | Name | Physical Data MS (ES), (m/z) |
|---|---|---|
| 306 | 2-[2-Fluoro-4-(7-pyridin-2-yl-imidazo[1,2-a]pyridin-3-yl)-phenyl]-N-[5-(tetrahydro-pyran-4-yl)-thiazol-2-yl]-acetamide | 514 (M + 1) |

Example 307

N-[4-Dimethylaminomethyl-5-(1-methyl-cyclopropyl)-thiazol-2-yl]-2-[2-fluoro-4-(7-pyridin-4-yl-imidazo[1,2-a]pyridin-3-yl)-phenyl]-acetamide

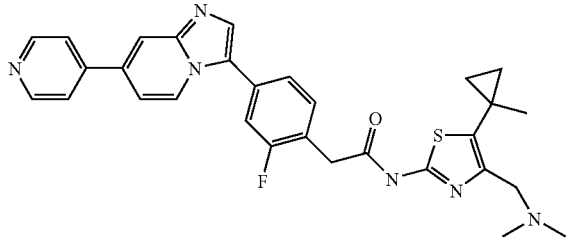

Combine 2-(4-bromo-2-fluoro-phenyl)-N-[4-dimethylaminomethyl-5-(1-methyl-cyclopropyl)-thiazol-2-yl]-acetamide (0.45 g, 1.06 mmol), 7-pyridin-4-yl-imidazo[1,2-a]pyridine (0.206 g, 1 equiv.), potassium acetate (0.52 g, 5 equiv.), tetrabutylammonium bromide (0.34 g, 1 equiv.), tris (2,4-di-t-butylphenyl)phosphite (0.034 g, 5 mol %) and NMP (10 mL). De-gas with nitrogen then add palladium (II) acetate (0.012 g, 5 mol %) and place under nitrogen. Heat at 120° C. for 24 hours then let stir at room temperature for an additional day. Dilute with ethyl acetate then wash with water, 1 N NaOH (aq), and aqueous saturated sodium chloride. Dry organics over MgSO$_4$, then filter and concentrate. Purify by reverse phase C$_{18}$ column HPLC employing a gradient of 5 to 65% to 100% acetonitrile versus 0.03% aqueous HCl then freebase by extraction with ethyl acetate versus 1 N NaOH (aq). Dry the organics over MgSO$_4$, then filter, and concentrate to give product (118 mg tan solid, 21%). MS (ES), m/z 541 (M+1).

The following compound is prepared with procedures similar to Example 307:

| Ex. | Name | Physical data MS (ES) m/z |
|---|---|---|
| 308 | N-[3-(2,2-Dimethyl-propionyl)-phenyl]-2-[2-fluoro-4-(7-pyridin-4-yl-imidazo[1,2-a]pyridin-3-yl)-phenyl]-acetamide | 507 (M + 1) |

Example 309

N-[4-Dimethylaminomethyl-5-(1-methyl-cyclopropyl)-thiazol-2-yl]-2-[2-fluoro-4-(7-pyridin-2-yl-imidazo[1,2-a]pyridin-3-yl)-phenyl]-acetamide

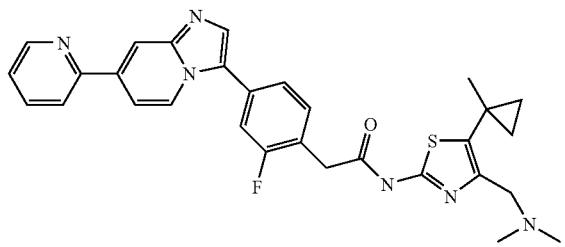

Combine [2-fluoro-4-(7-pyridin-2-yl-imidazo[1,2-a]pyridin-3-yl)-phenyl]-acetic acid, dihydrochloride (0.190 g, 0.452 mmol) and 4-Dimethylaminomethyl-5-(1-methyl-cyclopropyl)-thiazol-2-ylamine (0.105 g, 0.497 mmol) in DMF (4 mL). Add N,N-diisopropylethylamine (0.26 mL, 1.49 mmol), then O-(7-azabenzotriazol-1-yl)-N,N,N',N'-tetramethyluronium hexafluorophosphate (0.190 g, 0.500 mmol). The reaction mixture is stirred for 14 hours under $N_2$. Purify using an SCX cartridge (10 g VARIAN BondElut®), eluting with 1:1 methanol:dichloromethane, then 1:1 2 M $NH_3$ in methanol:dichloromethane. Purify via reverse phase chromatography using a 25 cm by 50.8 mm (i.d.) column w/10 micron particles (MeCN/0.03% HCl $H_2O$ (5:95) to 100% MeCN; 30 min). Partition between ethyl acetate and 1 N NaOH. Wash the organic layer with aqueous saturated sodium chloride, dry over magnesium sulfate, filter, and concentrate to the title compound (0.054 g, 22%). MS (ES), n/z 541 (M+1).

Prepare the following according to procedures similar to Example 309:

| Ex. | Name | Physical datat MS (ES) m/z |
|---|---|---|
| 310 | 2-[2-Fluoro-4-(7-pyridin-4-yl-imidazo[1,2-a]pyridin-3-yl)-phenyl]-N-(4,5,6,7-tetrahydro-benzothiazol-2-yl)-acetamide | 484 (M + 1) |
| 311 | 2-[2-Fluoro-4-(7-pyridin-2-yl-imidazo[1,2-a]pyridin-3-yl)-phenyl]-N-[5-(1-methyl-cyclopropyl)-4-morpholin-4-ylmethyl-thiazol-2-yl]-acetamide | 583 (M + 1) |
| 312 | 2-[2-Fluoro-4-(7-pyridin-4-yl-imidazo[1,2-a]pyridin-3-yl)-phenyl]-N-[5-(1-methyl-cyclopropyl)-4-morpholin-4-ylmethyl-thiazol-2-yl]-acetamide | 583 (M + 1) |
| 313 | 2-[2-Fluoro-4-(7-pyridin-4-yl-imidazo[1,2-a]pyridin-3-yl)-phenyl]-N-[4-(dimethylamino-methyl)-5-tert-butyl-thiazol-2-yl]-acetamide | 543 (M + 1) |
| 314 | 2-[2-Fluoro-4-(7-pyridin-2-yl-imidazo[1,2-a]pyridin-3-yl)-phenyl]-N-[4-(dimethylamino-methyl)-5-tert-butyl-thiazol-2-yl]-acetamide | 543 (M + 1) |

Example 315

2-[2-Fluoro-4-(7-pyridin-4-yl-imidazo[1,2-a]pyridin-3-yl)-phenyl]-N-[5-tert-butyl-4-morpholin-4-ylmethyl-thiazol-2-yl]-acetamide

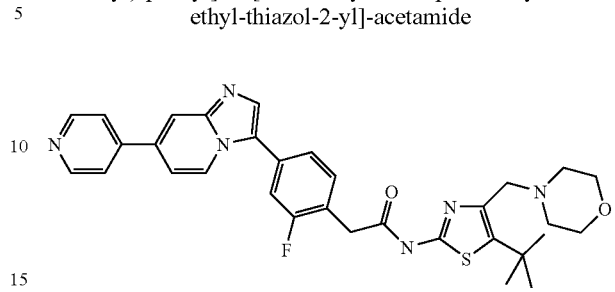

Combine [2-fluoro-4-(7-pyridin-2-yl-imidazo[1,2-a]pyridin-3-yl)-phenyl]-acetic acid, dihydrochloride (0.500 g, 1.19 mmol) and 5-tert-Butyl-4-morpholin-4-ylmethyl-thiazol-2-ylamine (0.334 g, 1.31 mmol) in DMF (6 mL). Add N,N-diisopropyl-ethylamine (0.54 mL, 3.93 mmol), then O-(7-azabenzotriazol-1-yl)-N,N,N',N'-tetra-methyluronium hexafluorophosphate (0.498 g, 1.31 mmol). The reaction mixture is stirred over the weekend under $N_2$. Purify using an SCX cartridge (10 g VARIAN BondElut®), eluting with 1:1 methanol:dichloromethane, then 1:1 2 M $NH_3$ in methanol:dichloromethane. Concentrate the latter and purify via reverse phase chromatography using a 25 cm by 50.8 mm (i.d.) column w/10 micron particles (MeCN/0.03% HCl $H_2O$ (5:95) to 100% MeCN; 30 min). Partition between ethyl acetate and 1 N NaOH. Dry the organic layer over magnesium sulfate, filter, and concentrate to the title compound (0.190 g, 27%). MS(ES), m/z 585 (M+1).

Prepare the following according to procedures similar to Example 309:

| Ex. | Name | Physical datat MS (ES) m/z |
|---|---|---|
| 316 | 2-[2-Fluoro-4-(7-pyridin-2-yl-imidazo[1,2-a]pyridin-3-yl)-phenyl]-N-[5-tert-butyl-4-morpholin-4-ylmethyl-thiazol-2-yl]-acetamide | 585 (M + 1) |

Example 317

2-{4-[7-(1-Oxy-pyridin-4-yl)-imidazo[1,2-a]pyridin-3-yl]-phenyl}-N-(3-trifluoromethyl-phenyl)-acetamide

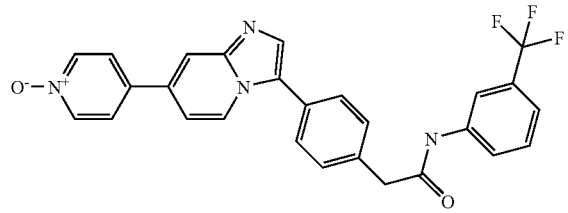

Dissolve 2-[4-(7-pyridin-4-yl-imidazo[1,2-a]pyridin-3-yl)-phenyl]-N-(3-trifluoromethyl-phenyl)-acetamide (0.80 g, 1.69 mmol) in 6 mL dichloromethane, add MTO (about 2 mg, 8.5 micromol, 0.005 eq), stir to dissolve, then add 2 mL water and 0.245 mL of 30% aqueous hydrogen peroxide to give a heavy yellow slurry. Stir 16-24 houtd at room temperature, add additional MTO (about 2 mg) and hydrogen peroxide (0.245 mL), stir 24 hours at room temperature. Finally, add another 2 mg MTO and 0.50 mL of hydrogen peroxide solution, stir 16 hours at room temperature. Remove solvents using a rotoraevaporator to afford a yellow solid. Dissolve the solid in dichloromethane-methanol, apply to a 120 g silica cartridge and elute with a gradient of 0→10% methanol in dichloromethane over 5 minutes. When unreacted starting acetamide has eluted, re-equilibrate the cartridge with 500 mL dichloromethane and elute with a gradient of 0→10% 1 N $NH_3$-methanol in dichloromethane over 30 minutes. Pool and concentrate clean fractions to give a yellow brittle foam and yellow glass. Resuspend the glass and foam in diethyl ether, remove solvents in vacuo, then dry at 50° C. under high vacuum to afford 330 mg (40%) of the title compound as a crystalline yellow solid. LCMS (ES) m/z 489 (M+1), 487 (M−).

Example 318

1-(4-{7-[4-(4-Methyl-piperazine-1-carbonyl)-phenyl]-imidazo[1,2-a]pyridin-3-yl}-benzyl)-3-(3-trifluoromethyl-phenyl)-urea

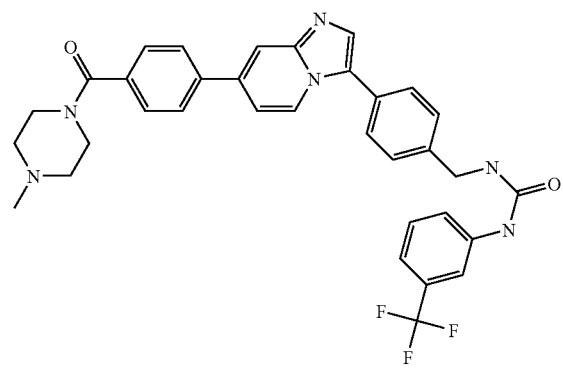

Combine {4-[3-(4-aminomethyl-phenyl)-imidazo[1,2-a]pyridin-7-yl]-phenyl}-(4-methyl-piperazin-1-yl)-methanone, bis hydrochloride (0.30 g, 0.56 mmol), 3-trifluoromethylphenyl isocyanate (0.1 mL, 0.73 mmol) and triethylamine (0.4 mL, 2.9 mmol) in DMSO (10 mL). Filter the solution through 10 g SCX column eluting with methanol→2 N ammonia in methanol. Concentrate fractions containing product to give a residue. Purify by chromatography (5% methanol in dichloromethane→10% methanol in dichloromethane→10% 2 N ammonia methanol in dichloromethane) to afford product (0.18 g, 52%). MS(ES), m/z 613 (M+1).

Example 319

1-(5-tert-Butyl-isoxazol-3-yl)-3-(4-{7-[4-(4-methyl-piperazine-1-carbonyl)-phenyl]-imidazo[1,2-a]pyridin-3-yl}-benzyl)-urea

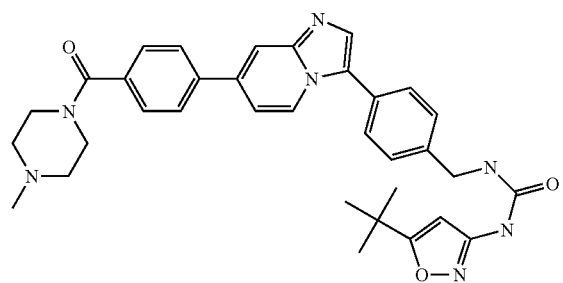

Combine {4-[3-(4-aminomethyl-phenyl)-imidazo[1,2-a]pyridin-7-yl]-phenyl}-(4-methyl-piperazin-1-yl)-methanone, bis hydrochloride (0.30 g, 0.56 mmol), (5-tert-butyl-isoxazol-3-yl)-carbamic acid 2,2,2-trichloro-ethyl ester (0.2 g, 0.63 mmol) and triethylamine (0.4 mL, 2.9 mmol) in DMSO (10 mL). Heat the mixture to 70° C., stir five hours, and cool to room temperature. Filter the solution through 10 g SCX column eluting with methanol→2 N ammonia in methanol. Concentrate fractions containing product to give a residue. Purify by chromatography (5% methanol in dichloromethane→10% methanol in dichloromethane→10% 2 N ammonia methanol in dichloromethane) to afford product (0.048 g, 15%). MS(ES), m/z 592 (M+1).

Example 320

1-(5-tert-Butyl-isoxazol-3-yl)-3-(2-fluoro-4-{7-[4-(piperazine-1-carbonyl)-phenyl]-imidazo[1,2-a]pyridin-3-yl}-phenyl)-urea hydrochloride

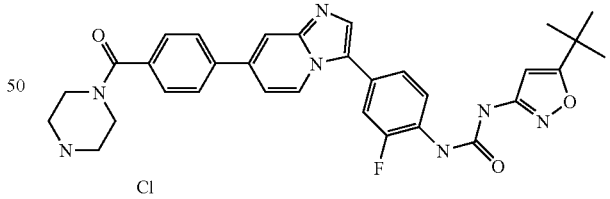

Dissolve 4-[4-(3-{4-[3-(5-tert-Butyl-isoxazol-3-yl)-ureido]-3-fluoro-phenyl}-imidazo[1,2-a]pyridin-7-yl)-benzoyl]-piperazine-1-carboxylic acid tert-butyl ester (1.53 g, 2.24 mmol) in $CH_2Cl_2$ (25 mL), to which is added HCl (5.6 mL, 4 M in dioxane). Stir at room temperature for three hours, then concentrate in vacuo to give light brown solid as product (1.60 g, 115%). MS (ES), m/z 582 (M+1, free base).

The compounds of the present invention are preferable formulated as pharmaceutical compositions administered by a variety of routes. Most preferably, such compositions are for oral administration. Such pharmaceutical compositions and processes for preparing same are well known in the art. See, e.g., REMINGTON: THE SCIENCE AND PRACTICE OF PHARMACY (A. Gennaro, et al., eds., 19$^{th}$ ed., Mack Publishing Co., 1995).

The compounds of Formula I are generally effective over a wide dosage range. For example, dosages per day normally fall within the range of about 0.1 to about 500 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

The following assay is performed to measure the $IC_{50}$ values of inhibition of phosphorylation of VEGF-R2 with compounds of the present invention.

Autophosphorylation Enzyme Assay

A. VEGFR2 (KDR) cloning and purification.

The isolated catalytic domain (Amino Acids 807-1356) of VEGFR2 (KDR-CD, cloned from a human heart cDNA library) is cloned by standard PCR procedures (pCR-Script to make plasmid P340) as a BamHI/HindIII fragment using the following primers: Upper: 5'-CCATGGATCCAGAT-GAACTCCC-3' and Lower: 5'-GAAGCTTAAACAGGAG-GAGAGCTCAG-3', its nucleotide sequence is verified and it is subcloned into the pFASTBac-HIS™ vector system (Gibco-BRL) (to give plasmid B344) for baculovirus expression. (Carroll, et al., J. Biol. Chem, 268, 12837-42 (1993). KDR-CD is expressed as an N-terminal 6×HIS fusion protein in Sf9 cells (Gibco-BRL) and purified according to standard affinity chromatography protocols (For example, Amersham Pharmacia Biotech: Affinity Chromatography Principles and Methods #18-1022-29). Briefly, 15-25 g pellets are lysed in lysis buffer (50 mM Tris pH 7.5, 150 mM NaCl, 0.5% NP40 (CalbioChem) with freshly added 20 mM -mercaptoethanol, 10 mM imidazole, 1 mM PMSF(protease inhibitor (phenylmethanesulfonyl fluoride) from Sigma), 1×EDTA-free complete protease inhibitor (Boehringer Mannheim)) on ice for 30 minutes. The cell lysates are cleared by centrifugation at 30,000 g for 20 minutes at 4° C., filtered through a 0.2 M filter and applied to a NiNTA™ column (Qiagen). Unbound protein is removed with successive RIPA buffer washes (50 mM Tris pH 7.5, 150 mM NaCl, 1% NP40, 1 mM EDTA, 0.25% sodium deoxycholate, 20 mM -mercaptoethanol), lysis buffer washes and finally 1× kinase buffer (KB) washes (100 mM HEPES pH 7.5, 10 mM $MnCl_2$, 5 mM -mercaptoethanol). KDR protein is eluted in 1× KB containing a linear gradient of 200 mM imidazole over 10 column volumes. The peak fractions (based on a SDS-PAGE gel analysis) are combined, concentrated by Centricon™ to ~1 mg/mL and desalted over an HR26/10 desalting column (Amersham Pharmacia) in 1× KB. This KDR prep is estimated to be ~40% pure with only KDR tyrosine kinase activity detectable by anti-phosphotyrosine western analysis following the in vitro autophosphorylation reaction.

B. KDR-CD In Vitro Autophosphorylation Kinase Assay

Kinase reactions contain 1 μg total protein in 40 μL reaction volume containing 4% (v/v) DMSO final concentration, 1 μM ATP, 1 uCi/rxn $^{33}$P-ATP (from NEN) in 1×KB. A compound dilution series of 20 μM to 1.0 nM is added to the above reaction to determine compound activity; test compound may be pre-incubated with KDR enzyme for up to 30 minutes at 30° C. prior to addition of the radiolabel. The radiolabeling reaction is carried out at 30° C. for 20 minutes before adding 100 μL 25% TCA with 3 mM ATP to stop the reaction, then precipitated with 50 μL 1 mg/mL BSA. The quenched reactions are transferred to MultiScreen™-FC plates (Millipore) and incubated for 1 hour at room temperature. The plates are filtered, washed 3× with 250 μL 10% TCA and blotted dry. MicroScint™20 (Packard) is added and the plate is counted on a Wallac Microbeta™. Dougher-Vermazen, M. et al., Biochem Biophys Res Commun 205(1): 728-738 (1994). The $IC_{50}$ values are calculated from a logistic 4-parameter curve fit. For all examples included herein, the $IC_{50}$ values are less than $1.0×10^{-6}$ M.

All values are determined using a 30 minute preincubation of compound and enzyme prior to initiating the labeling reaction and represent the average of at least two separate determinations:

| Example | $IC_{50}$ (nM) |
|---|---|
| 39 | 28 |
| 130 | 42 |
| 173 | 26 |
| 196 | 106 |
| 289 | 41 |
| 303 | 46 |

In Vivo Efficacy in PC-3 Prostate Tumor Xenografts

Male SCID mice (Fox Chase, Taconic laboratories) are implanted s.c. in the rear flank with 0.2 mL of a cell suspension prepared in serum-free media containing $5×10^6$ PC-3 human prostate adenocarcinoma cells (obtained from ATCC). Example 130 is prepared as a suspension in 1% CMC/0.25% Tween 80 and administered by oral gavage for 21 days beginning after tumors reach approximately 150-200 mg (volume calculated by l×w$^2$×0.536 where l is the larger and w is the smaller of perpendicular diameters determined by caliper measurement). Example 130 is administered twice daily (12 hours apart) for the 15, 7.5, and 3.75 mg/kg doses while the 30 mg/kg dose is given once daily. Groups consists of 8 mice each and one group receives 0.2 mL of the CMC/Tween vehicle twice daily as a control. Statistical analysis is performed by two-way ANOVA and all treatment groups are statistically different from the control group (p<0.001) at study termination:

| Day | n | Mean | SE | Signif. | n | Mean | SE | Signif. |
|---|---|---|---|---|---|---|---|---|
| | 1% CMC/.25% PS80, 0.2 mL | | | | Ex 130, 3.75 mg/kg | | | |
| 55 | 8 | 715.3 | 123.3 | Ctrl | 8 | 268.1 | 36.5 | ** |
| 57 | 8 | 880.6 | 153.4 | Ctrl | 8 | 310.1 | 36.8 | *** |
| | Ex 130, 7.5 mg/kg | | | | Ex 130, 15 mg/kg | | | |
| 55 | 8 | 100.8 | 21.1 | *** | 6 | 67.7 | 16.9 | *** |
| 57 | 8 | 86.3 | 19 | *** | 6 | 62.2 | 17.4 | *** |
| | Ex 130, 30 mg/kg | | | | | | | |
| 55 | 8 | 95.7 | 16.6 | *** | | | | |
| 57 | 8 | 86.8 | 17 | *** | | | | |

Mean Tumor Volumes and Std Errors

SE = Std Error
***: p <= 0.001
**: 0.001 < p <= 0.01

We claim:
1. A compound of Formula (I):

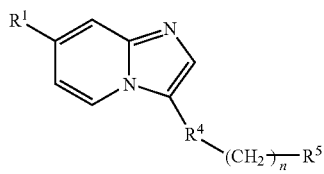

wherein:
- $R^1$: is (a) 2-pyridonyl optionally substituted with —$(CH_2)_{1-4}NR^2R^3$; or
  (b) phenyl, thienyl, thiazolyl, imidazolyl, pyrazolyl, triazolyl, oxazolyl, pyridinyl, N-oxo-pyridinyl, or pyrimidinyl, all of which are optionally substituted with —$(CH_2)_{0-4}NR^2R^3$, $C_1$-$C_6$ alkyl optionally substituted with amino, pyrrolidinyl, or morpholinyl, or 1-2 substituents independently selected from the group consisting of $C_1$-$C_4$ alkoxy, halo, ($C_1$-$C_6$ alkyl)sulfonyl, nitro, -sulfonyl$(CH_2)_{0-4}NR^2R^3$, and -carbonyl$(CH_2)_{0-4}NR^2R^3$;
- $R^2$ is hydrogen or $C_1$-$C_6$ alkyl optionally substituted with hydroxy;
- $R^3$ is hydrogen or $C_1$-$C_6$ alkyl optionally substituted with hydroxy, trifluoromethyl, or pyrrolidinyl; or $R^2$, $R^3$, and the nitrogen to which they are attached form piperidinyl, piperazinyl optionally substituted with $C_1$-$C_6$ alkyl, or morpholinyl;
- $R^4$ is thiazolyl, pyridinyl, or phenyl optionally substituted with 1-3 substituents selected from the group consisting of halo, amino, methyl, trifluoromethyl, and nitro;
- $R^5$ is $C(O)NHR^6$, $OC(O)NHR^6$, $NHC(O)CH_2R^6$, $NHC(O)NHR^6$ or $C(S)NHR^6$;
- n is 0-4 for $OC(O)NHR^6$, $NHC(O)CH_2R^6$, $NHC(O)NHR^6$ and n is 1-4 for $C(O)NHR^6$ and $C(S)NHR^6$; and
- $R^6$ is (a) unsubstituted tetrahydrobenzothiazolyl; or
  (b) phenyl, pyridinyl, pyrimidinyl, pyrazolyl, thiazolyl, isothiazolyl, thiadiazolyl, isoxazolyl, all of which are optionally substituted with 1-3 substituents independently selected from the group consisting of $C_1$-$C_6$ alkyl optionally substituted with hydroxy, dimethylamino, pyrrolidinyl, piperidinyl, or morpholinyl, $C_2$-$C_6$ alkenyl optionally substituted with dimethylaminocarbonyl, $C_1$-$C_6$ alkoxy, trifluoromethyl, difluoromethoxy, trifluoromethoxy, dimethylaminoethoxy, phenoxy, tolyl, halo, methylsulfonyl, dimethylamino, diethylamino, cyano, $C_3$-$C_6$ cycloalkyl optionally substituted with hydroxy, methoxy, methoxyethoxy, or methyl, 3,4-dimethylisoxazol-5-yl-aminosulfonyl, tetrahydropyranyl, tetrahydropyranylaminocarbonyl, $C_2$-$C_6$ alkylcarbonyl, morpholinylcarbonyl, and piperazinylcarbonyl; or pharmaceutically acceptable salts thereof.

2. A compound according to claim 1 wherein $R^5$ is $C(O)NHR^6$.

3. A compound according to claim 1 or 2 wherein $R^1$ is phenyl, thienyl, thiazolyl, or pyridinyl all of which are optionally substituted with —$(CH_2)_{0-4}NR^2R^3$, $C_1$-$C_6$ alkyl optionally substituted with amino, pyrrolidinyl, or morpholinyl, or 1-2 substituents independently selected from the group consisting of $C_1$-$C_4$ alkoxy, halo, ($C_1$-$C_6$ alkyl)sulfonyl, nitro, -sulfonyl$(CH_2)_{0-4}NR^2R^3$, and -carbonyl$(CH_2)_{0-4}NR^2R^3$.

4. A pharmaceutical formulation comprising a compound according to any one of claims 1-3 in combination with a pharmaceutically acceptable carrier, diluent, or solvent.

5. The compound of claim 1 which is 2-{2-Fluoro-4-[7-(2-methyl-pyridin-4-yl)-imidazo[1,2-a]pyridin-3-yl]-phenyl}-N-(3-trifluoromethyl-phenyl)-acetamide or a pharmaceutically acceptable salt thereof.

6. The compound of claim 1 which is N-(5-tert-Butylisoxazol-3-yl)-2-[2-fluoro-4-(7-pyridin-2-yl-imidazo [1,2-a]pyridin-3-yl)-phenyl]-acetamide or a pharmaceutically acceptable salt thereof.

7. The compound of claim 1 which is 2-[4-(7-pyridin-4-yl-imidazo[1,2-a]pyridin-3-yl)-phenyl]-N-(3-trifluoromethyl-phenyl)-acetamide or a pharmaceutically acceptable salt thereof.

* * * * *

UNITED STATES PATENT AND TRADEMARK OFFICE
CERTIFICATE OF CORRECTION

PATENT NO. : 7,666,879 B2  Page 1 of 1
APPLICATION NO. : 11/816416
DATED : February 23, 2010
INVENTOR(S) : David Anthony Barda It is certified that error appears in the above-identified patent and that said Letters Patent is hereby corrected as shown below:

Page 1, column 1 (Inventors)
Delete "Zionsvillc"
Insert --Zionsville--

Signed and Sealed this

Twenty-seventh Day of April, 2010

David J. Kappos
*Director of the United States Patent and Trademark Office*